US006579854B1

(12) United States Patent
Mitchell et al.

(10) Patent No.: US 6,579,854 B1
(45) Date of Patent: Jun. 17, 2003

(54) DIAGNOSIS AND MANAGEMENT OF INFECTION CAUSED BY CHLAMYDIA

(75) Inventors: William M. Mitchell, Nashville, TN (US); Charles W. Stratton, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/073,661

(22) Filed: May 6, 1998

Related U.S. Application Data

(63) Continuation-in-part of application No. 09/025,174, filed on Feb. 18, 1998, which is a continuation-in-part of application No. 09/025,521, filed on Feb. 18, 1998, now abandoned, which is a continuation-in-part of application No. 09/025,176, filed on Feb. 18, 1998, now Pat. No. 6,258,532, which is a continuation-in-part of application No. 08/911,593, filed on Aug. 14, 1997, now abandoned.

(60) Provisional application No. 60/045,689, filed on May 6, 1997, provisional application No. 60/045,739, filed on May 6, 1997, provisional application No. 60/045,779, filed on May 6, 1997, provisional application No. 60/045,780, filed on May 6, 1997, provisional application No. 60/045,787, filed on May 6, 1997, and provisional application No. 60/023,921, filed on Aug. 14, 1996.

(51) Int. Cl.$^7$ .................... A61K 31/70; A61K 31/65; A61K 31/43; A61K 31/47; A61K 31/18

(52) U.S. Cl. .................... 514/31; 514/152; 514/192; 514/198; 514/311; 514/601; 514/631

(58) Field of Search ................ 424/114, 263.1; 436/518, 6; 435/7.2, 300; 530/389.5, 350; 536/16.8, 23.1, 24.3, 24.32; 514/31, 631, 152, 192, 198, 601, 311

(56) References Cited

U.S. PATENT DOCUMENTS

| | | | |
|---|---|---|---|
| 4,952,594 A | 8/1990 | Mercer | 514/398 |
| 5,217,493 A | 6/1993 | Raad et al. | 623/11.11 |
| 5,424,187 A | 6/1995 | Shor et al. | 435/6 |
| 5,650,405 A | 7/1997 | Remington et al. | 514/183 |
| 5,795,563 A | 8/1998 | Kallick | 424/9.361 |
| 5,880,101 A | 3/1999 | Stankov | 514/29 |
| 6,258,532 B1 * | 7/2001 | Stratton et al. | 435/6 |

FOREIGN PATENT DOCUMENTS

| | | |
|---|---|---|
| EP | 0 337 733 A2 | 10/1989 |
| EP | 0 546 761 A1 | 6/1993 |
| EP | 0 699 688 A2 | 3/1996 |
| EP | 0 192 033 A2 | 8/1996 |
| WO | WO 98/06435 | 2/1998 |
| WO | 98/50074 | * 11/1998 |
| WO | WO9220352 | * 11/1999 |

OTHER PUBLICATIONS

Windholz et al., The Merck Index, Tenth Edition (1983), pp. 531, 532, 1017 and 1187.*

Budavari et al., the Merck Index, Twelfth Edition (1996), pp 157.*

Wang et al., Effects of Ascorbic Acid on Chlamydia Trachomatis Infection and on Erythromycin Treatment in Primary Cultures of Human Amniotic Cells. J.Clin.Microbiol, 30. 2551–2554, 1992.*

Bertrand et al., "L'Ofloxacine (RU 43280) Etude Clinique," Path. Biol., 35: 629–633, 1987.

Drancourt et al., "Oral Rifampin plus Ofloxacin for Treatment of Staphylococcus –Infected Orthopedic Implants," Antimicrobial Agents and Chemotherapy, 37: 1214–1218, 1993.

Freidank et al., "In Vitro Susceptibilities of *Chlamydia pneumoniae* Isolates from German Patients and Synergistic Activity of Antibiotic Combinations," Antimicrobial Agents and Chemotheraphy, 43: 1808–1810, 1999.

Jones et al., "In Vitro Activity of Rifamycins Alone and in Combination with Other Antibiotics Against *Chlamydia trachomatis*," Reviews of the Infectious Diseases, 5: S556–S564, 1983.

Miettinen, A., et al., "The Effect of Ciprofloxacin and Doxycycline Plus Metronidazole on Lower Genital Tract Flora in Patients with Proven Pelvic Inflammatory Disease", Arch. Gynecol. Obstet., 249: 95–101 (1991).

Judlin, P., et al., "Etude Comparative Des Associations Ofloxacine + Amoxicilline–Acide Clavulanique Versus Doxycycline + Amoxicilline–Acid Clavulanique Dans Le Traitement Des Infections Génitales Hautes A *Chlamydia trachomatis*", J. Gynecol. Obstet. Biol. Reprod., 24: 253–259 (1995).

Henry–Suchet, J., "Traitement Des Infections Utéro–Annexielles Sexuellement Transmises (IUAST) Sauf Syphilis Et Herpès", Méd. Mal. Infect., 24: 379–387 (1994).

Joly–Guillou, M.L., et al., "Bactéries Isolées En 1994–1995 Au Cours Des Infections Gynécologiques Hautes Et Des Uréthrites Masculines", La Presse Mèdicale 2–9 Mars. 25, (8): 342–348.

(List continued on next page.)

Primary Examiner—Kevin E. Weddington
(74) Attorney, Agent, or Firm—Clark & Elbing LLP

(57) ABSTRACT

The present invention provides a unique approach for the diagnosis and management of infections by Chlamydia species, particularly *C. pneumoniae*. The invention is based, in part, upon the discovery that a combination of agents directed toward the various stages of the chlamydial life cycle is effective in substantially reducing infection. Products comprising combination of antichlamydial agents, novel compositions and pharmaceutical packs are also described.

9 Claims, 4 Drawing Sheets

OTHER PUBLICATIONS

Orfila, J. and Haider, F., "Comparative Study Of The In Vitro Activity Of Lomefloxacin Versus Lomefloxacin Combined With Metronidazole Versus Lomefloxacin In Combination With Amoxicilli/Clavulanic Acid Against *Chlamydia trachomatis*", *Intern. J. Antimicro. Agents,* 2: 11–14 (1992).

Witte, E.H., et al., "A Comparison Of Pefloxacin/Metronidazole And Doxycycline/Metronidazole in the Treatment of Laparoscopically Confirmed Acute Pelvic Inflammatory Disease", *Eur. J. Obstet. Gynec. and Repro. Bio.,* 50:153–158 (1993).

Heinonen, Pentti K., et al., "A Comparison of Ciprofloxacin with Doxycycline plus Metronidazole in the Treatment of Acute Pelvic Inflammatory Disease", *Scand. J. Infect. Dis. Suppl.,* 60: 66–73 (1989).

Burchell, H.J., et al., "Efficacy of Different Antibiotics in the Treatment of Pelvic Inflammatory Disease", *SAMJ.,* 72: 248–249 (Aug. 15, 1987).

Paavonen, J., et al., "Factors Predicting Abnormal Hysterosal–pingographic Findings in Patients Treated for Acute Pelvic Inflammatory Disease", *Int. J. Gynaecol. Obstet.,* 23: 171–175 (1985).

The Merck Manual of Diagnosis and Therapy, 16th Ed., pp. 181–182, 257–258 and 691–694 (1992).

Schachter, "Rifampin in Chlamydial Infections,"Reviews of Infectious Diseases, 5;S 562–S564, 1983.

* cited by examiner

```
MS...113aa...MHHHHHHS...35aa...KAMAKK...363aa...FRF
   │                │             │               │
 THIOREDOXIN    POLYHISTIDINE  SOLUBILITY        MOMP
   DOMAIN        DOMAIN        SEQUENCE         DOMAIN
                                DOMAIN
                                        ↑
                               ENTEROKINASE
                               CLEAVAGE SITE
```

|  |  |  | SEQ ID NO. |
|---|---|---|---|
| CPN90-105 | C.pneumoniae | CTGSAA_ANYTTAVD-RPN | 93 |
| CTP89-105 | C.trachomatis (MOUSE) | CTGDADLTTAPTPAS-REN | 94 |
| CTL91-106 | C.trachomatis (L2) | CTTATGNAAAPSTCTAREN | 95 |
| CPS92-106 | C.psitacci | CASGTA-SNTTVAAD-RSN | 96 |

| | | | SEQ ID NO. |
|---|---|---|---|
| CPN158-171 | *C.pneumoniae* | CFGVKGTTVNANE---LP | 97 |
| CTP158-171 | *C.trachomatis* (MOUSE) | CFGRDETAVAADD---IP | 98 |
| CTL159-175 | *C.trachomatis* (L2) | CFGDNENHATVSDSKLVP | 99 |
| CPS160-172 | *C.psitacci* | CIGLAGTDF-ANQ---RP | 100 |

Fig. 4

| | | | SEQ ID NO. |
|---|---|---|---|
| CPN342-354 | *C.pneumoniae* | CQINKFKSRKACG | 101 |
| CTP342-354 | *C.trachomatis* (MOUSE) | CQINKMKSRFACG | 102 |
| CTL342-354 | *C.trachomatis* (L2) | CQLNKMKSRKACG | 103 |
| CPS342-354 | *C.psitacci* | CQINKFKSRFACG | 104 |

Fig. 5

SEQUENCE LISTING (1) GENERAL INFORMATION:

(iii) NUMBER OF SEQUENCES: 114

(2) INFORMATION FOR SEQ ID NO:1:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:1:

ATGAAAAAAC TCTTAAAGTC GGCGTTATTA TCCGCCGCAT TTGCTGGTTC          50

(2) INFORMATION FOR SEQ ID NO:2:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:2:

ATGAAAAAAC TCTTAAAGTC GGCGTTATTA TCCGCCGCAT TTGCTGGTTC          50

(2) INFORMATION FOR SEQ ID NO:3:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:3:

ATGAAAAAAC TCTTGAAGTC GGCATTATTG TTTGCCGCTA CGGGTTCCGC          50

(2) INFORMATION FOR SEQ ID NO:4:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:4:

ATGAAAAAAC TCTTAAAGTC GGCGTTATTA TCCGCCGCAT TTGCTGGTTC          50

(2) INFORMATION FOR SEQ ID NO:5:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:5:

ATGAAAAAAC TCTTGAAATC GGCATTATTG TTTGCCGCTA CGGGTTCCGC          50

(2) INFORMATION FOR SEQ ID NO:6:

(i) SEQUENCE CHARACTERISTICS:
       (A) LENGTH: 50 base pairs
       (B) TYPE: nucleic acid
       (C) STRANDEDNESS: single (D) TOPOLOGY: linear (xi) SEQUENCE DESCRIPTION: SEQ ID NO:6:

ATGAAAAAAC TCTTGAAATC GGCATTATTG TTTGCCGCTA CGGGTTCCGC      50

(2) INFORMATION FOR SEQ ID NO:7:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:7:

ATGAAAAAAC TCTTGAAATC GGCATTATTG TTTGCCGCTA CGGGTTCCGC      50

(2) INFORMATION FOR SEQ ID NO:8:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:8:

ATGAAAAAAC TCTTGAAATC GGCATTATTA TTTGCCGCTA CGGGTTCCGC      50

(2) INFORMATION FOR SEQ ID NO:9:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:9:

ATGAAAAAAC TCTTAAAATC GGCATTATTA TTTGCCGCTG CGGGTTCCGC      50

(2) INFORMATION FOR SEQ ID NO:10:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:10:

ATGAAAAAAC TCTTGAAATC GGTATTAGTA TTTGCCGCTT TGAGTTCTGC      50

(2) INFORMATION FOR SEQ ID NO:11:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:11:

ATGAAAAAAC TCTTGAAATC GGTATTAGTA TTTGCCGCTT TGAGTTCTGC      50

(2) INFORMATION FOR SEQ ID NO:12:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:12:

ATGAAAAAAC TCTTGAAATC GGTATTAGTA TTTGCCGCTT TGAGTTCTGC           50

(2) INFORMATION FOR SEQ ID NO:13:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:13:

ATGAAAAAAC TCTTGAAATC GGTATTAGTA TTTGCCGCTT TGAGTTCTGC           50

(2) INFORMATION FOR SEQ ID NO:14:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:14:

ATGAAAAAAC TCTTGAAATC GGTATTAGTA TTTGCCGCTT TGAGTTCTGC           50

(2) INFORMATION FOR SEQ ID NO:15:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:15:

ATGAAAAAAC TCTTGAAATC GGTATTAGTA TTTGCCGCTT TGAGTTCTGC           50

(2) INFORMATION FOR SEQ ID NO:16:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:16:

ATGAAAAAAC TCTTGAAATC GGTATTAGTG TTTGCCGCTT TGAGTTCTGC           50

(2) INFORMATION FOR SEQ ID NO:17:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:17:

ATGAAAAAAC TCTTGAAATC GGTATTAGTG TTTGCCGCTT TGAGTTCTGC           50

(2) INFORMATION FOR SEQ ID NO:18:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:18:

ATGAAAAAAC TCTTGAAATC GGTATTAGTG TTTGCCGCTT TGAGTTCTGC           50

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:19:

ATGAAAAAAC TCTTGAAATC GGTATTAGCA TTTGCCGTTT TGGGTTCTGC           50

(2) INFORMATION FOR SEQ ID NO:20:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:20:

GTTTAATTAA CGAGAGAGCT GCTCACGTAT CTGGTCAGTT CAGATTCTAA           50

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:21:

GTTTAATTAA CGAGAGAGCT GCTCACGTAT CTGGTCAGTT CAGATTCTAA           50

(2) INFORMATION FOR SEQ ID NO:22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:22:

CAACGTTAAT CGACGCTGAC AAATGGTCAA TCACTGGTGA AGCACGCTTA           50

(2) INFORMATION FOR SEQ ID NO:23:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:23:

GTTTAATTAA CGAGAGAGCT GCTCACATAT CTGGTCAGTT CAGATTCTAA           50

(2) INFORMATION FOR SEQ ID NO:24:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:24:

AACGTTAATC GACGCTGACA AATGGTCAAT CACTGGTGAA GCACGCTTAA         50

(2) INFORMATION FOR SEQ ID NO:25:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:25:

AACGTTAATC GACGCTGACA AATGGTCAAT CACTGGTGAA GCACGCTTAA         50

(2) INFORMATION FOR SEQ ID NO:26:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:26:

GCTTAATCAA TGAAAGAGCC GCTCACATGA ATGCTCAATT CAGATTCTAA         50

(2) INFORMATION FOR SEQ ID NO:27:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:27:

GCTTAATCAA TGAAAGAGCT GCTCACATGA ATGCTCAATT CAGATTCTAA         50

(2) INFORMATION FOR SEQ ID NO:28:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:28:

GCTTAATCGA CGAAAGAGCT GCTCACATTA ATGCTCAATT CAGATTCTAA         50

(2) INFORMATION FOR SEQ ID NO:29:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:29:

CGCAGTTACA GTTGAGACTC GCTTGATCGA TGAGAGAGCA GCTCACGTAA         50

(2) INFORMATION FOR SEQ ID NO:30:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:30:

GCTTGATCGA TGAGAGAGCA GGTCACGTAA ATGCACAATT CCGGTTCTAA          50

(2) INFORMATION FOR SEQ ID NO:31:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:31:

GCTTGATCGA TGAGAGAGCA GCTCACGTAA ATGCACAATT CCGCTTCTAA          50

(2) INFORMATION FOR SEQ ID NO:32:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:32:

CGCTTGATCG ATGAGAGACT GCTCACGTAA ATGCACAATT CCGCTTCTAA          50

(2) INFORMATION FOR SEQ ID NO:33:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:33:

GCTTGATCGA TGAGAGAGCT GCTCACGTAA ATGCACAATT CCGCTTCTAA          50

(2) INFORMATION FOR SEQ ID NO:34:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:34:

GCTTGATCGA TGAGAGAGCA GCTCACGTAA ATGCACAATT CCGCTTCTAA          50

(2) INFORMATION FOR SEQ ID NO:35:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:35:

GCTTGATCGA TGAGAGAGCT GCTCACGTAA ATGCACAATT CCGCTTCTAA          50

(2) INFORMATION FOR SEQ ID NO:36:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:36:

CTTGATCGAT GAGAGAGCTG CTCACGTAAA TGCACAATTC CGCTTCTAA           49

(2) INFORMATION FOR SEQ ID NO:37:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:37:

```
GCTTGATCGA TGAGAGAGCA GCTCACGTAA ATGCACAATT CCGCTTCTAA        50
```

(2) INFORMATION FOR SEQ ID NO:38:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:38:

```
GCTTGATCGA TGAAAGAGCA GCTCACGTAA ATGCTCAGTT CCGTTTCTAA        50
```

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:39:

```
CAGATACGTG AGCAGCTCTC TC                                      22
```

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:40:

```
CTCTTAAAGT CGGCGTTATT ATCCG                                   25
```

(2) INFORMATION FOR SEQ ID NO:41:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:41:

```
ATGAAAAAAC TCTTAAAGTC GGCGTTATTA TCCGCCGC                     38
```

(2) INFORMATION FOR SEQ ID NO:42:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:42:

```
TTAGAATCTG AACTGACCAG ATACGTGAGC AGCTCTCTCG                   40
```

(2) INFORMATION FOR SEQ ID NO:43:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (xi) SEQUENCE DESCRIPTION: SEQ ID NO:43:

AGCTTACCAT GGCTAAAAAA CTCTTAAAGT CGGCGTTATT ATCCG                45

(2) INFORMATION FOR SEQ ID NO:44:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:44:

ATATGCGGCC GCTCATAGAA TCTGAACTGA CCAGATACG                       39

(2) INFORMATION FOR SEQ ID NO:45:

(i) SEQUENCE CHARACTERISTICS:
       (A) LENGTH: 100 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:45:

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Gln Thr Asp Val Asn Lys
65                  70                  75                  80

Glu Phe Gln Met Gly Ala Lys Pro Thr Thr Ala Thr Gly Asn Ala Ala
                85                  90                  95

Ala Pro Ser Thr
            100

(2) INFORMATION FOR SEQ ID NO:46:

(i) SEQUENCE CHARACTERISTICS:
       (A) LENGTH: 100 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:46:

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser

-continued

```
                20                  25                  30
Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Ile Met Gly Tyr
     50                  55                  60

Tyr Gly Asp Phe Val Phe Asp Arg Val Leu Lys Thr Asp Val Asn Lys
 65                 70                  75                  80

Glu Phe Gln Met Gly Ala Lys Pro Thr Thr Thr Gly Asn Ala Ala
                85                  90                  95

Ala Pro Ser Thr
            100

(2) INFORMATION FOR SEQ ID NO:47:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Tyr
     50                  55                  60

Tyr Gly Asp Phe Val Phe Asp Arg Val Leu Glu Thr Asp Val Asn Lys
 65                 70                  75                  80

Glu Phe His Met Gly Ala Lys Pro Thr Thr Asp Thr Gly Asn Ser Ala
                85                  90                  95

Ala Pro Leu Thr
            100

(2) INFORMATION FOR SEQ ID NO:48:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Ile Met Gly Tyr
     50                  55                  60

Tyr Gly Asp Phe Val Phe Asp Arg Val Leu Lys Thr Asp Val Asn Lys
 65                 70                  75                  80
```

```
Glu Phe His Met Gly Asp Lys Pro Thr Ser Thr Thr Gly Asn Ala Thr
                85                  90                  95
Ala Pro Thr Thr
            100
```

(2) INFORMATION FOR SEQ ID NO:49:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Met Lys Lys Leu Leu Lys Ser Val Leu Val Phe Ala Ala Leu Ser Ser
  1               5                  10                  15
Ala Ser Ser Leu Gln Ala Leu Pro Val Gly Asn Pro Ala Glu Pro Ser
                20                  25                  30
Leu Met Ile Asp Gly Ile Leu Trp Glu Gly Phe Gly Gly Asp Pro Cys
                35                  40                  45
Asp Pro Cys Thr Thr Trp Cys Asp Ala Ile Ser Met Ile Met Gly Tyr
            50                  55                  60
Tyr Gly Asp Phe Val Phe Asp Arg Val Leu Lys Thr Asp Val Asn Lys
 65                  70                  75                  80
Glu Phe His Met Gly Asp Lys Pro Thr Ala Thr Thr Gly Asn Ala Ala
                85                  90                  95
Ala Pro Ser Thr
            100
```

(2) INFORMATION FOR SEQ ID NO:50:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Met Lys Lys Leu Leu Lys Ser Val Leu Val Phe Ala Ala Leu Ser Ser
  1               5                  10                  15
Ala Ser Ser Leu Gln Ala Leu Pro Val Gly Asn Pro Ala Glu Pro Ser
                20                  25                  30
Leu Met Ile Asp Gly Ile Leu Trp Glu Gly Phe Gly Gly Asp Pro Cys
                35                  40                  45
Asp Pro Cys Thr Thr Trp Cys Asp Ala Ile Ser Met Ile Met Gly Tyr
            50                  55                  60
Tyr Gly Asp Phe Val Phe Asp Arg Val Leu Lys Thr Asp Val Asn Lys
 65                  70                  75                  80
Glu Phe Lys Met Gly Glu Ala Leu Ala Gly Ser Thr Gly Asn Thr Thr
                85                  90                  95
Ser Thr Leu Ser Lys
            100
```

(2) INFORMATION FOR SEQ ID NO:51:

(i) SEQUENCE CHARACTERISTICS:
        (A) LENGTH: 103 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:51:

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Val Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Ala Gly
                85                  90                  95

Leu Gln Asn Asp Pro Thr Ile
                100

(2) INFORMATION FOR SEQ ID NO:52:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Arg Asp Val Ala Gly Leu
                85                  90                  95

Glu Lys Asp Pro Val Val
                100

(2) INFORMATION FOR SEQ ID NO:53:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
            35                  40                  45

Ala Pro Cys Thr Thr Trp Cys Asp Ala Ile Ser Met Val Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Asn Asp Ala Ala Pro Lys
                85                  90                  95

Thr (2) INFORMATION FOR SEQ ID NO:54:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Val Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Glu Pro Thr Thr Ser Asp Thr Ala Gly Leu
                85                  90                  95

Ser Asn Asp Pro Thr Thr
            100

(2) INFORMATION FOR SEQ ID NO:55:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

Met Lys Lys Leu Leu Lys Ser Val Ala Val Phe Val Ala Gly Ser Ser
1               5                   10                  15

Ala Ser Ser Leu His Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Leu
    50                  55                  60

Tyr Leu Asp Phe Val Phe Asp Arg Val Leu Lys Thr Asp Val Asn Lys
65                  70                  75                  80

Gln Phe Glu Met Gly Ala Ala Pro Thr Gly Asp Ala Asp Leu Thr Thr
                85                  90                  95

Ala Pro Thr Pro
        100

(2) INFORMATION FOR SEQ ID NO:56:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Met Lys Lys Leu Leu Lys Ala Val Leu Ala Phe Ala Phe Ala Gly Ser
1               5                   10                  15

Val Gly Ser Leu Gln Ala Leu Pro Val Gly Asn Pro Ala Ser Asp Ser
            20                  25                  30

Leu Leu Ile Asp Gly Thr Ile Trp Glu Gly Ala Ala Gly Asp Pro Cys
        35                  40                  45

Asp Pro Ala Thr Thr Trp Cys Asp Ala Ile Ser Leu Arg Ala Gly Phe
    50                  55                  60

Tyr Gly Asp Phe Val Tyr Asp Ile Val Leu Lys Val Asp Ala Pro Lys
65                  70                  75                  80

Thr Phe Ser Met Gly Ala Lys Pro Thr Thr Gly Asn Gly Ser Ala
                85                  90                  95

Ala Ala Asn (2) INFORMATION FOR SEQ ID NO:57:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Cys Thr Ala Arg Glu Asn Pro Ala Tyr Gly Arg His Met Gln Asp Ala
1               5                   10                  15

Glu Met Phe Thr Asn Ala Ala Tyr Met Ala Leu Ile Asn Trp Asp Arg
            20                  25                  30

Phe Asp Val Phe Cys Thr Leu Gly Ala Thr Ser Gly Tyr Leu Lys Gly
        35                  40                  45

Asn Ser Ala Ser Phe Asn Leu Val Gly Leu Phe Gly Asp Asn Glu Asn
    50                  55                  60

His Ala Thr Val Ser Asp Ser Lys Leu Val Pro Asn Met Ser Leu Asp
65                  70                  75                  80

Gln Ser Val Val Glu Leu Tyr Thr Asp Thr Thr Phe Ala Trp Ser Ala
                85                  90                  95

Gly Ala Arg Ala
        100

(2) INFORMATION FOR SEQ ID NO:58:

(i) SEQUENCE CHARACTERISTICS:
        (A) LENGTH: 65 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO:58:

Leu Thr Ala Arg Glu Asn Pro Ala Tyr Gly Arg His Met Gln Asp Ala
 1               5                  10                  15

Glu Met Phe Thr Asn Cys Ala Tyr Met Ala Leu Ile Asn Trp Asp Arg
             20                  25                  30

Phe Asp Val Phe Cys Thr Leu Gly Ala Ser Ser Gly Tyr Leu Lys Gly
         35                  40                  45

Asn Ser Ala Ser Phe Asn Leu Val Gly Leu Phe Gly Asn Asn Glu Asn
     50                  55                  60

Gln
 65

(2) INFORMATION FOR SEQ ID NO:59:

(i) SEQUENCE CHARACTERISTICS:
       (A) LENGTH: 134 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:59:

Cys Thr Ala Arg Glu Asn Pro Ala Tyr Gly Arg His Met Gln Asp Ala
 1               5                  10                  15

Glu Met Phe Thr Asn Cys Ala Tyr Met Ala Leu Ile Asn Trp Asp Arg
             20                  25                  30

Phe Asp Val Phe Cys Thr Leu Gly Ala Thr Ser Gly Tyr Leu Lys Gly
         35                  40                  45

Asn Ser Ala Ser Phe Asn Leu Val Gly Leu Phe Gly Asp Asn Glu Asn
     50                  55                  60

Gln Lys Thr Val Lys Ala Glu Ser Val Pro Asn Met Ser Phe Asp Gln
 65              70                  75                  80

Ser Val Val Glu Leu Tyr Thr Asp Thr Phe Ala Trp Ser Val Gly
                 85                  90                  95

Ala Arg Ala Thr Lys Val Ser Asn Gly Thr Phe Val Pro Asn Met Ser
             100                 105                 110

Leu Asp Gln Ser Val Val Glu Leu Tyr Thr Asp Thr Ala Phe Ala Trp
             115                 120                 125

Ser Val Gly Ala Arg Ala
             130

(2) INFORMATION FOR SEQ ID NO:60:

(i) SEQUENCE CHARACTERISTICS:
       (A) LENGTH: 99 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:60:

Leu Thr Ala Arg Glu Asn Pro Ala Tyr Gly Arg His Met Gln Asp Ala
 1               5                  10                  15

Glu Met Phe Thr Asn Cys Ala Tyr Met Ala Leu Ile Asn Trp Asp Arg

```
                    20                  25                  30
Phe Asp Val Phe Cys Thr Leu Gly Ala Ser Ser Gly Tyr Leu Lys Gly
            35                  40                  45

Asn Ser Ala Ser Phe Asn Leu Val Gly Leu Phe Gly Asp Asn Glu Asn
        50                  55                  60

Gln Ser Thr Val Lys Thr Asn Ser Val Pro Asn Met Ser Leu Asp Gln
 65                  70                  75                  80

Ser Val Val Glu Leu Tyr Thr Asp Thr Ala Phe Ser Trp Ser Val Gly
                85                  90                  95

Ala Arg Ala
```

(2) INFORMATION FOR SEQ ID NO:61:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Cys Thr Ala Arg Glu Asn Pro Ala Tyr Gly Arg His Met Gln Asp Ala
 1                   5                  10                  15

Glu Met Phe Thr Asn Ala Ala Tyr Met Ala Leu Ile Asn Trp Asp Arg
                20                  25                  30

Phe Asp Val Phe Cys Thr Leu Gly Ala Thr Ser Gly Tyr Leu Lys Gly
            35                  40                  45

Asn Ser Ala Ser Phe Asn Leu Val Gly Leu Phe Gly Asp Asn Glu Asn
        50                  55                  60

Gln Ser Thr Val Lys Lys Asp Ala Val Pro Asn Met Ser Phe Asp Gln
 65                  70                  75                  80

Ser Val Val Glu Leu Tyr Thr Asp Thr Thr Phe Ala Trp Ser Val Gly
                85                  90                  95

Ala Arg Ala
```

(2) INFORMATION FOR SEQ ID NO:62:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

```
Leu Val Glu Arg Thr Asn Pro Ala Tyr Gly Lys His Met Gln Asp Ala
 1                   5                  10                  15

Glu Met Phe Thr Asn Cys Ala Tyr Thr Ala Leu Ile Asn Trp Asp Arg
                20                  25                  30

Phe Asp Val Phe Cys Thr Leu Gly Ala Thr Ser Gly Tyr Leu Lys Gly
            35                  40                  45

Asn Ser Ala Ser Phe Asn Leu Val Gly Leu Phe Gly Asp Gly Val Asn
        50                  55                  60

Ala Thr Lys Pro Ala Ala Asp Ser Ile Pro Asn Val Gln Leu Asn Gln
 65                  70                  75                  80

Ser Val Val Glu Leu Tyr Thr Asp Thr Thr Phe Ala Trp Ser Val Gly
                85                  90                  95
```

```
Ala Arg Ala (2) INFORMATION FOR SEQ ID NO:63:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Asn Val Ala Arg Pro Asn Pro Ala Tyr Gly Lys His Met Gln Asp Ala
  1               5                  10                  15

Glu Met Phe Thr Asn Ala Ala Tyr Met Ala Leu Ile Asn Trp Asp Arg
             20                  25                  30

Phe Asp Val Phe Cys Thr Leu Gly Ala Thr Thr Gly Tyr Leu Lys Gly
         35                  40                  45

Asn Ser Ala Ser Phe Asn Leu Val Gly Leu Phe Gly Thr Lys Thr Gln
     50                  55                  60

Ser Ser Ser Phe Asn Thr Ala Lys Leu Ile Pro Asn Thr Ala Leu Asp
 65                  70                  75                  80

Gln Ser Val Val Glu Leu Tyr Ile Asn Thr Thr Phe Ala Trp Ser Val
                 85                  90                  95

Gly Ala Arg Ala
            100

(2) INFORMATION FOR SEQ ID NO:64:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Asn Val Ala Arg Pro Asn Pro Ala Tyr Gly Lys His Met Gln Asp Ala
  1               5                  10                  15

Glu Met Phe Thr Asn Ala Ala Tyr Met Ala Leu Ile Asn Trp Asp Arg
             20                  25                  30

Phe Asp Val Phe Cys Thr Leu Gly Ala Thr Thr Gly Tyr Leu Lys Gly
         35                  40                  45

Asn Ser Ala Ser Phe Asn Leu Val Gly Leu Phe Gly Thr Lys Thr Gln
     50                  55                  60

Ser Ser Gly Phe Asp Thr Ala Asn Ile Val Pro Asn Thr Ala Leu Asn
 65                  70                  75                  80

Gln Ala Val Val Glu Leu Tyr Thr Asp Thr Thr Phe Ala Trp Ser Val
                 85                  90                  95

Gly Ala Arg Ala
            100

(2) INFORMATION FOR SEQ ID NO:65:

(i) SEQUENCE CHARACTERISTICS:
        (A) LENGTH: 100 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:65:

Asn Val Ala Arg Pro Asn Pro Ala Tyr Gly Lys His Met Gln Asp Ala
1               5                   10                  15

Glu Met Phe Thr Asn Ala Ala Tyr Met Ala Leu Ile Asn Trp Asp Arg
                20                  25                  30

Phe Asp Val Phe Cys Thr Leu Gly Ala Thr Thr Gly Tyr Leu Lys Gly
            35                  40                  45

Asn Ser Ala Ser Phe Asn Leu Val Gly Leu Phe Gly Thr Lys Thr Lys
        50                  55                  60

Ser Ser Asp Phe Asn Thr Ala Lys Leu Val Pro Asn Ile Ala Leu Asn
65                  70                  75                  80

Arg Ala Val Val Glu Leu Tyr Thr Asp Thr Thr Phe Ala Trp Ser Val
                85                  90                  95

Gly Ala Arg Ala
            100

(2) INFORMATION FOR SEQ ID NO:66:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Asn Val Ala Arg Pro Asn Pro Ala Tyr Gly Lys His Met Gln Asp Ala
1               5                   10                  15

Glu Met Phe Thr Asn Ala Ala Tyr Met Ala Leu Ile Asn Trp Asp Arg
                20                  25                  30

Phe Asp Val Phe Cys Thr Leu Gly Ala Thr Thr Gly Tyr Leu Lys Gly
            35                  40                  45

Asn Ser Ala Ser Phe Asn Leu Val Gly Leu Phe Gly Thr Lys Thr Gln
        50                  55                  60

Ser Thr Asn Phe Asn Thr Ala Lys Leu Val Pro Asn Thr Ala Leu Asn
65                  70                  75                  80

Gln Ala Val Val Glu Leu Tyr Thr Asp Thr Thr Phe Ala Trp Ser Val
                85                  90                  95

Gly Ala Arg Ala
            100

(2) INFORMATION FOR SEQ ID NO:67:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Ala Ser Arg Glu Asn Pro Ala Tyr Gly Lys His Met Gln Asp Ala Glu
1               5                   10                  15

Met Phe Thr Asn Ala Ala Tyr Met Ala Leu Ile Asn Trp Asp Arg Phe
                20                  25                  30

```
Asp Val Phe Cys Thr Leu Gly Ala Thr Ser Gly Tyr Leu Lys Gly Asn
        35                  40                  45

Ser Ala Ala Phe Asn Leu Val Gly Leu Phe Gly Arg Asp Glu Thr Ala
    50                  55                  60

Val Ala Ala Asp Asp Ile Pro Asn Val Ser Leu Ser Gln Ala Val Val
65              70                  75                      80

Glu Leu Tyr Thr Asp Thr Ala Phe Ala Trp Ser Val Gly Ala Arg Ala
                85                  90                  95
```

(2) INFORMATION FOR SEQ ID NO:68:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

```
Tyr Thr Thr Ala Val Asp Arg Pro Asn Pro Ala Tyr Asn Lys His Leu
 1               5                  10                  15

His Asp Ala Glu Trp Phe Thr Asn Ala Gly Ile Phe Ala Leu Ile Asn
            20                  25                  30

Trp Asp Arg Phe Asp Val Phe Cys Thr Leu Gly Ala Ser Asn Gly Ile
        35                  40                  45

Arg Lys Gly Asn Ser Thr Ala Phe Asn Leu Val Gly Leu Phe Gly Val
    50                  55                  60

Lys Gly Thr Thr Val Asn Ala Asn Glu Leu Pro Asn Val Ser Leu Ser
65              70                  75                      80

Asn Gly Val Val Glu Leu Tyr Thr Asp Thr Ser Phe Ser Trp Ser Val
                85                  90                  95

Gly Ala Arg Ala
        100
```

(2) INFORMATION FOR SEQ ID NO:69:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

```
Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Gln Glu Phe
        35                  40                  45

Pro Leu Asp Leu Lys Ala Gly Thr Asp Gly Val Thr Gly Thr Lys Asp
    50                  55                  60

Ala Ser Ile Asp Tyr His Glu Trp Gln Ala Ser Leu Ala Leu Ser Tyr
65              70                  75                      80

Arg Leu Asn Met Phe Thr Pro Tyr Ile Gly Val Lys Trp Ser Arg Ala
                85                  90                  95

Ser Phe Asp Ala
        100
```

(2) INFORMATION FOR SEQ ID NO:70:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

```
Ala Leu Trp Glu Cys Gly Cys Ala Thr Leu Gly Ala Ser Phe Gln Tyr
 1               5                  10                  15
Ala Gln Ser Lys Pro Lys Val Glu Glu Leu Asn Val Leu Cys Asn Ala
            20                  25                  30
Ala Glu Phe Thr Ile Asn Lys Pro Lys Gly Tyr Val Gly Lys Glu Leu
        35                  40                  45
Pro Leu Asp Leu Thr Ala Gly Thr Asp Ala Ala Thr Gly Thr Lys Asp
50                  55                  60
Ala Ser Ile Asp Tyr His Glu Trp Gln Ala Ser Leu Ala Leu Ser Tyr
65                  70                  75                  80
Arg Leu Asn Met Phe Thr Pro Tyr Ile Gly Val Lys Trp Ser Arg Ala
                85                  90                  95
Ser Phe Asp Ala
            100
```

(2) INFORMATION FOR SEQ ID NO:71:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

```
Ala Leu Trp Glu Cys Gly Cys Ala Thr Leu Gly Ala Ser Phe Gln Tyr
 1               5                  10                  15
Ala Gln Ser Lys Pro Lys Val Glu Leu Asn Val Leu Cys Asn Ala
            20                  25                  30
Ala Glu Phe Thr Ile Asn Lys Pro Lys Gly Tyr Val Gly Lys Glu Phe
        35                  40                  45
Pro Leu Asp Leu Thr Ala Gly Thr Asp Ala Ala Thr Gly Thr Lys Asp
50                  55                  60
Ala Ser Ile Asp Tyr His Glu Trp Gln Ala Ser Leu Ala Leu Ser Tyr
65                  70                  75                  80
Arg Leu Asn Met Phe Thr Pro Tyr Ile Gly Val Lys Trp Ser Arg Ala
                85                  90                  95
Ser Phe Asp Ala
            100
```

(2) INFORMATION FOR SEQ ID NO:72:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Gln Glu Phe
        35                  40                  45

Pro Leu Ala Leu Ile Ala Gly Thr Asp Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

(2) INFORMATION FOR SEQ ID NO:73:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Lys Glu Phe
        35                  40                  45

Pro Leu Asp Leu Thr Ala Gly Thr Asp Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

(2) INFORMATION FOR SEQ ID NO:74:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

Ala Leu Trp Glu Cys Gly Cys Ala Thr Leu Gly Ala Ser Phe Gln Tyr
1               5                   10                  15

Ala Gln Ser Lys Pro Lys Ile Glu Glu Leu Asn Val Leu Cys Asn Ala
            20                  25                  30

Ala Glu Phe Thr Ile Asn Lys Pro Lys Gly Tyr Val Gly Lys Glu Phe
        35                  40                  45

```
Pro Leu Asp Leu Thr Ala Gly Thr Asp Ala Ala Thr Gly Thr Lys Asp
    50                  55                  60

Ala Ser Ile Asp Tyr His Glu Trp Gln Ala Ser Leu Ser Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ser
            100
```

(2) INFORMATION FOR SEQ ID NO:75:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

```
Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
                20                  25                  30

Ser Glu Phe Thr Ile Asn Lys Pro Lys Gly Tyr Val Gly Ala Glu Phe
            35                  40                  45

Pro Leu Asn Ile Thr Ala Gly Thr Glu Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Val
                85                  90                  95

Ser Phe Asp Ala
            100
```

(2) INFORMATION FOR SEQ ID NO:76:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
                20                  25                  30

Ser Glu Phe Thr Ile Asn Lys Pro Lys Gly Tyr Val Gly Ala Glu Phe
            35                  40                  45

Pro Leu Asp Ile Thr Ala Gly Thr Glu Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Val
                85                  90                  95

Ser Phe Asp Ala
```

(2) INFORMATION FOR SEQ ID NO:77:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
            20                  25                  30

Ser Glu Phe Thr Ile Asn Lys Pro Lys Gly Tyr Val Gly Ala Glu Phe
        35                  40                  45

Pro Leu Asp Ile Thr Ala Gly Thr Glu Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Val
                85                  90                  95

Ser Phe Asp Ala
            100
```

(2) INFORMATION FOR SEQ ID NO:78:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

```
Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asp Ala
            20                  25                  30

Ser Glu Phe Thr Ile Asn Lys Pro Lys Gly Tyr Val Gly Ala Glu Phe
        35                  40                  45

Pro Leu Asp Ile Thr Ala Gly Thr Glu Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Val
                85                  90                  95

Ser Phe Asp Ala
            100
```

(2) INFORMATION FOR SEQ ID NO:79:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Gln Glu Phe
        35                  40                  45

Pro Leu Asn Ile Lys Ala Gly Thr Val Ser Ala Thr Asp Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

(2) INFORMATION FOR SEQ ID NO:80:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

Gly Leu Trp Glu Cys Gly Cys Ala Thr Leu Gly Glu Ser Phe Gln Tyr
1               5                   10                  15

Ala Gln Ser Lys Pro Lys Val Glu Glu Leu Asn Val Ile Cys Asn Val
            20                  25                  30

Ser Gln Phe Ser Val Asn Lys Pro Lys Gly Tyr Lys Gly Val Ala Phe
        35                  40                  45

Pro Leu Pro Thr Asp Ala Gly Val Ala Thr Ala Thr Gly Thr Lys Ser
    50                  55                  60

Ala Thr Ile Asn Tyr His Glu Trp Gln Val Gly Ala Ser Leu Ser Tyr
65                  70                  75                  80

Arg Leu Asn Ser Leu Val Pro Tyr Ile Gly Val Gln Trp Ser Arg Ala
                85                  90                  95

Thr Phe Asp Ala
            100

(2) INFORMATION FOR SEQ ID NO:81:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Asp Thr Ile Arg Ile Ala Gln Pro Lys Ser Ala Thr Val Phe Asp
1               5                   10                  15

Val Thr Thr Leu Asn Pro Thr Ile Ala Gly Ala Gly Asp Val Lys Ala
            20                  25                  30

Ser Ala Glu Gly Gln Leu Gly Asp Thr Met Gln Ile Val Ser Leu Gln

```
                35                  40                  45
Leu Asn Lys Met Lys Ser Arg Lys Ser Cys Gly Ile Ala Val Gly Thr
     50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                 85                  90
```

(2) INFORMATION FOR SEQ ID NO:82:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

```
Asp Thr Ile Arg Ile Ala Gln Pro Lys Ser Ala Glu Thr Ile Phe Asp
 1               5                  10                  15

Val Thr Thr Leu Asn Pro Thr Ile Ala Gly Ala Gly Asp Val Lys Thr
                 20                  25                  30

Ser Ala Glu Gly Gln Leu Gly Asp Thr Met Gln Ile Val Ser Leu Gln
                 35                  40                  45

Leu Asn Met Lys Ser Arg Lys Cys Gly Ile Ala Val Gly Thr Thr Ile
     50                  55                  60

Val Asp Ala Asp Lys Tyr Ala Ile Thr Val Glu Thr Arg Leu Ile Asp
 65                  70                  75                  80

Glu Arg Ala Ala His Val Asn Ala Gln Phe Arg Phe
                 85                  90
```

(2) INFORMATION FOR SEQ ID NO:83:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

```
Asp Thr Ile Arg Ile Ala Gln Pro Lys Ser Ala Thr Ala Ile Phe Asp
 1               5                  10                  15

Thr Thr Thr Leu Asn Pro Thr Ile Ala Gly Ala Gly Asp Val Lys Thr
                 20                  25                  30

Gly Thr Glu Gly Gln Leu Gly Asp Thr Met Gln Ile Val Ser Leu Gln
                 35                  40                  45

Leu Asn Lys Met Lys Ser Arg Lys Ser Cys Gly Ile Ala Val Gly Thr
     50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                 85                  90
```

(2) INFORMATION FOR SEQ ID NO:84:

(i) SEQUENCE CHARACTERISTICS:
        (A) LENGTH: 94 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:84:

Asp Thr Ile Arg Ile Ala Gln Pro Lys Ser Ala Thr Ala Ile Phe Asp
1               5                   10                  15

Thr Thr Thr Leu Asn Pro Thr Ile Ala Gly Ala Gly Asp Val Lys Ala
            20                  25                  30

Ser Ala Glu Gly Gln Leu Gly Asp Thr Met Gln Ile Val Ser Leu Gln
        35                  40                  45

Leu Asn Lys Met Lys Ser Arg Lys Ser Cys Gly Ile Ala Val Gly Thr
    50                  55                  60

Thr Ile Val Asp Ala Asp Lys Tyr Ala Val Thr Val Glu Thr Arg Leu
65                  70                  75                  80

Ile Asp Glu Arg Ala Ala His Val Asn Ala Gln Phe Arg Phe
                85                  90

(2) INFORMATION FOR SEQ ID NO:85:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:85:

Asp Thr Ile Arg Ile Ala Gln Pro Lys Leu Ala Thr Ala Ile Phe Asp
1               5                   10                  15

Thr Thr Thr Leu Asn Pro Thr Ile Ala Gly Ala Gly Asp Glu Lys Ala
            20                  25                  30

Asn Ala Glu Gly Gln Leu Gly Asp Thr Met Gln Ile Val Ser Leu Gln
        35                  40                  45

Leu Asn Lys Met Lys Ser Arg Lys Ser Cys Gly Ile Ala Val Gly Thr
    50                  55                  60

Thr Ile Val Asp Ala Asp Lys Tyr Ala Val Thr Val Glu Thr Arg Leu
65                  70                  75                  80

Ile Asp Glu Arg Ala Ala His Val Asn Ala Gln Phe Arg Phe
                85                  90

(2) INFORMATION FOR SEQ ID NO:86:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:86:

Asp Thr Ile Arg Ile Ala Gln Pro Arg Leu Val Thr Pro Val Val Asp
1               5                   10                  15

Ile Thr Thr Leu Asn Pro Thr Ile Ala Gly Ala Cys Asp Ser Lys Ala
            20                  25                  30

Gly Asn Thr Glu Gly Gln Ile Ser Asp Thr Met Gln Ile Val Ser Leu
        35                  40                  45

Gln Leu Asn Lys Met Lys Ser Arg Lys Ser Cys Gly Ile Ala Val Gly

```
                   50                  55                  60
Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg Phe
                     85                  90                  95
```

(2) INFORMATION FOR SEQ ID NO:87:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

```
Asp Thr Ile Arg Ile Ala Gln Pro Lys Leu Ala Glu Ala Ile Leu Asp
 1                   5                  10                  15

Val Thr Thr Leu Asn Arg Thr Thr Ala Gly Lys Gly Ser Val Val Ser
                    20                  25                  30

Ala Gly Thr Asp Asn Glu Leu Ala Asp Thr Met Gln Ile Val Ser Leu
                    35                  40                  45

Gln Leu Asn Lys Met Lys Ser Arg Lys Ser Cys Gly Ile Ala Val Gly
 50                  55                  60

Thr Thr Ile Val Asp Ala Asp Lys Tyr Ala Val Thr Val Glu Ala Arg
 65                  70                  75                  80

Leu Ile Asp Glu Arg Ala Ala His Val Asn Ala Gln Phe Arg Phe
                    85                  90                  95
```

(2) INFORMATION FOR SEQ ID NO:88:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:88:

```
Asp Thr Ile Arg Ile Ala Gln Pro Lys Leu Ala Lys Pro Val Leu Asp
 1                   5                  10                  15

Thr Thr Thr Leu Asn Pro Thr Ile Ala Gly Lys Gly Thr Val Val Ser
                    20                  25                  30

Ser Ala Glu Asn Glu Leu Ala Asp Thr Met Gln Ile Val Ser Leu Gln
                    35                  40                  45

Leu Asn Lys Met Lys Ser Arg Lys Ser Cys Gly Ile Ala Val Gly Thr
 50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                    85                  90
```

(2) INFORMATION FOR SEQ ID NO:89:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

Asp Thr Ile Arg Ile Ala Gln Pro Lys Leu Ala Glu Ala Ile Leu Asp
  1               5                  10                  15

Val Thr Thr Leu Asn Pro Thr Ile Ala Gly Lys Gly Thr Val Val Ala
                 20                  25                  30

Ser Gly Ser Asp Asn Asp Leu Ala Asp Thr Met Gln Ile Val Ser Leu
            35                  40                  45

Gln Leu Asn Lys Met Lys Ser Arg Lys Ser Cys Gly Ile Ala Val Gly
 50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg
                 85                  90

(2) INFORMATION FOR SEQ ID NO:90:

(i) SEQUENCE CHARACTERISTICS:
          (A) LENGTH: 95 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:90:

Asp Thr Ile Arg Ile Ala Gln Pro Lys Leu Ala Glu Ala Val Leu Asp
  1               5                  10                  15

Val Thr Thr Leu Asn Pro Thr Ile Ala Gly Lys Gly Ser Val Val Ala
                 20                  25                  30

Ser Gly Ser Glu Asn Glu Leu Ala Asp Thr Met Gln Ile Val Ser Leu
            35                  40                  45

Gln Leu Asn Lys Met Lys Ser Arg Lys Ser Cys Gly Ile Ala Val Gly
 50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg Phe
                 85                  90                  95

(2) INFORMATION FOR SEQ ID NO:91:

(i) SEQUENCE CHARACTERISTICS:
          (A) LENGTH: 91 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:91:

Asp Thr Ile Arg Ile Ala Gln Pro Lys Leu Glu Thr Ser Ile Leu Lys
  1               5                  10                  15

Met Thr Thr Trp Asn Pro Thr Ile Ser Gly Ser Gly Ile Asp Val Asp
                 20                  25                  30

Thr Lys Ile Thr Asp Thr Leu Gln Ile Val Ser Leu Gln Leu Asn Lys
            35                  40                  45

Met Lys Ser Arg Lys Ser Cys Leu Ile Ala Ile Gly Thr Thr Ile Val
 50                  55                  60

Asp Ala Asp Lys Tyr Ala Val Thr Val Glu Thr Arg Leu Ile Asp Glu

```
                65                  70                  75                  80
Arg Ala Ala His Val Asn Ala Gln Phe Arg Phe
                    85                  90
```

(2) INFORMATION FOR SEQ ID NO:92:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:92:

```
Asp Asn Ile Arg Ile Ala Gln Pro Lys Leu Pro Thr Ala Val Leu Asn
1               5                   10                  15
Leu Thr Ala Trp Asn Pro Ser Leu Leu Gly Asn Ala Thr Ala Leu Ser
                20                  25                  30
Thr Thr Asp Ser Phe Ser Asp Phe Met Gln Ile Val Ser Cys Gln Ile
                35                  40                  45
Asn Lys Phe Lys Ser Arg Lys Ala Cys Val Thr Ala Val Ala Thr Leu
    50                  55                  60
Ile Val Asp Ala Asp Lys Trp Ser Leu Thr Ala Glu Ala Arg Leu Asn
65              70                  75                  80
Asp Glu Arg Ala Ala His Ser Gly Ala Gln Phe Arg Phe
                85                  90
```

(2) INFORMATION FOR SEQ ID NO:93:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

```
Cys Thr Gly Ser Ala Ala Ala Asn Tyr Thr Thr Ala Val Asp Arg Pro
1               5                   10                  15
Asn
```

(2) INFORMATION FOR SEQ ID NO:94:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:94:

```
Cys Thr Gly Asp Ala Asp Leu Thr Thr Ala Pro Thr Pro Ala Ser Arg
1               5                   10                  15
Glu Asn
```

(2) INFORMATION FOR SEQ ID NO:95:

(i) SEQUENCE CHARACTERISTICS:
        (A) LENGTH: 19 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:95:

Cys Thr Thr Ala Thr Gly Asn Ala Ala Ala Pro Ser Thr Cys Thr Ala
1               5                   10                  15

Arg Glu Asn (2) INFORMATION FOR SEQ ID NO:96:

(i) SEQUENCE CHARACTERISTICS:
          (A) LENGTH: 17 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:96:

Cys Ala Ser Gly Thr Ala Ser Asn Thr Thr Val Ala Ala Asp Arg Ser
1               5                   10                  15

Asn (2) INFORMATION FOR SEQ ID NO:97:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:97:

Cys Phe Gly Val Lys Gly Thr Thr Val Asn Ala Asn Glu Leu Pro
1               5                   10                  15

(2) INFORMATION FOR SEQ ID NO:98:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:98:

Cys Phe Gly Arg Asp Glu Thr Ala Val Ala Ala Asp Asp Ile Pro
1               5                   10                  15

(2) INFORMATION FOR SEQ ID NO:99:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:99:

Cys Phe Gly Asp Asn Glu Asn His Ala Thr Val Ser Asp Ser Lys Leu
1               5                   10                  15

Val Pro (2) INFORMATION FOR SEQ ID NO:100:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:100:

```
Cys Ile Gly Leu Ala Gly Thr Asp Phe Ala Asn Gln Arg Pro
1               5                   10
```

(2) INFORMATION FOR SEQ ID NO:101:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

```
Cys Gln Ile Asn Lys Phe Lys Ser Arg Lys Ala Cys Gly
1               5                   10
```

(2) INFORMATION FOR SEQ ID NO:102:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

```
Cys Gln Ile Asn Lys Met Lys Ser Arg Phe Ala Cys Gly
1               5                   10
```

(2) INFORMATION FOR SEQ ID NO:103:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

```
Cys Gln Leu Asn Lys Met Lys Ser Arg Lys Ala Cys Gly
1               5                   10
```

(2) INFORMATION FOR SEQ ID NO:104:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

```
Cys Gln Ile Asn Lys Phe Lys Ser Arg Phe Ala Cys Gly
1               5                   10
```

(2) INFORMATION FOR SEQ ID NO:105:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:105:

ATGAAAAAAC TCTTAAAGTC GGCGTTATTA TCCGCCGC                           38

(2) INFORMATION FOR SEQ ID NO:106:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (xi) SEQUENCE DESCRIPTION: SEQ ID NO:106:

ATGAAAAAAC TCTTGAAATC GGTATTAGTG TTTGCCGCTT TGAG                    44

(2) INFORMATION FOR SEQ ID NO:107:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (xi) SEQUENCE DESCRIPTION: SEQ ID NO:107:

ATGAAAAAAC TCTTAAAATC GGCATTATTA TTTGCCGCTG CGGG                    44

(2) INFORMATION FOR SEQ ID NO:108:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (xi) SEQUENCE DESCRIPTION: SEQ ID NO:108:

ATGAAAAAAC TCTTGAAATC GGCATTATTG TTTGCCGCTA CGGG                    44

(2) INFORMATION FOR SEQ ID NO:109:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:109:

ATGAAAAAAC TCTTGAAATC GGTATTAGCA TTTGCCGTTT TGGGTTCTGC              50

(2) INFORMATION FOR SEQ ID NO:110:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (xi) SEQUENCE DESCRIPTION: SEQ ID NO:110:

TTAGAATCTG AACTGACCAG ATACGTGAGC AGCTCTCTCG                         40

```
(2) INFORMATION FOR SEQ ID NO:111:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:111:

TTAGAAGCGG AATTGTGCAT TTACGTGAGC AGCTC                                  35

(2) INFORMATION FOR SEQ ID NO:112:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:112:

TTAGAATCTG AATTGAGCAT TAATGTGAGC AGCTCTTTCG TCG                         43

(2) INFORMATION FOR SEQ ID NO:113:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:113:

TTAGAATCTG AATTGACCAT TCATGTGAGC AGCTCTTTCA TTGATTAAGC G                51

(2) INFORMATION FOR SEQ ID NO:114:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:114:

TTAGAAACGG AACTGAGCAT TTACGTGAGC TGCTCTTTCA TC                          42
```

DIAGNOSIS AND MANAGEMENT OF INFECTION CAUSED BY CHLAMYDIA

RELATED APPLICATIONS

This application claims benefit of U.S. Ser. No. 60/045,689, U.S. Ser. No. 60/045,739, U.S. Ser. No. 60/045,779, U.S. Ser. No. 60/045,780, and U.S. Ser. No. 60/045,787, each of which was filed May 6, 1997 and is now abandoned. This application is also a continuation-in-part of U.S. Ser. No. 09/025,174 (now pending), U.S. Ser. No. 09/025,176 (now U.S. Pat. No. 6,258,532), and U.S. Ser. No. 09/025,521 (now abandoned), each of which was filed Feb. 18, 1998. U.S. Ser. No. 09/025,176 is a continuation-in-part of U.S. Ser. No. 08/911,593, filed Aug. 14, 1997 (now abandoned), which claims benefit of U.S. Ser. No. 60/023,921, filed Aug. 14, 1996 (now abandoned). The entire teachings of all of the foregoing applications are hereby incorporated by reference.

BACKGROUND OF THE INVENTION

Chlamydiae are obligate intracellular microorganisms which parasitize eukaryotic cells and are ubiquitous throughout the animal kingdom. Members of the chlamydial genus are considered bacteria with a unique biphasic developmental cycle having distinct morphological and functional forms. This developmental growth cycle alternates between 1) intracellular life forms, of which two are currently recognized, a metabolically-active, replicating organism known as the reticulate body (RB) and a persistent, non-replicating organism known as the cryptic phase; and 2) an extracellular life form that is an infectious, metabolically-inactive form known as the elementary body (EB)

EBs are small (300–400 nm) infectious, spore-like forms which are metabolically inactive, non-replicating, and found most often in the acellular milieu. EBs are resistant to a variety of physical insults such as enzyme degradation, sonication and osmotic pressure. This physical stability is thought to be a result of extensive disulfide cross-linking of the cysteine-rich major outer membrane protein (MOMP) (Bavoil et al., *Infection and Immunity*, 44:479–485 (1984); Hackstadt et al., *Journal of Bacteriology*, 161:25–31 (1985); Hatch et al., *Journal of Bacteriology*, 165:379–385 (1986); Peeling et al., *Infection and Immunity*, 57:3338–3344 (1989); J. C. A. Bardwell, *Molecular Microbiology*, 14:199–205 (1994); and T. P. Hatch, *Journal of Bacteriology*, 178:1–5 (1993)). Under oxidizing conditions in the acellular milieu of the host, the outer membrane of EBs is relatively impermeable as well as resistant to inactivation. EBs are thus well suited to survive long enough outside of their hosts to be transmitted to a new host in the form of a droplet nuclei (Theunissen et al., *Applied Environmental Microbiology*, 59:2589–2593 (1993)) or a fomite (Fasley et al., *The Journal of Infectious Diseases*, 168:493–496 (1993)).

Infection by members of the genus Chlamydiae induces a significant inflammatory response at the cellular level. For example, genital lesions produced by *Chlamydia trachomatis* frequently elicit a vigorous influx of lymphocytes, macrophages, and plasma cells, suggesting the development of humoral and cellular immunity. Yet, clinically, the initial infection is frequently varied in symptomatology and may even be asymptomatic. Once fully established, the Chlamydia are difficult to eradicate, with frequent relapse following antibiotic therapy. Evidence also indicates that the Chlamydia may become dormant and are then shed in quantities too few to reliably detect by culture.

*Chlamydia pneumoniae* (hereinafter "*C. pneumoniae*") is the most recent addition to the genus Chlamydiae and is isolated from humans and currently is recognized as causing approximately 10 percent of community acquired cases of pneumonia (Grayston et al., *J. Inf. Dis.* 161:618–625 (1990)). This newly recognized pathogen commonly infects the upper and lower respiratory tract and is now recognized as ubiquitous in humans. *C. pneumoniae* is well-accepted as a human pathogen that may be difficult to eradicate by standard antibiotic therapy (Hammerschlag et al., *Clin. Infect. Dis.* 14:178–182 (1992)). *C. pneumoniae* is known to persist as a silent or mildly symptomatic pathogen, resulting in a chronic, persistent infection (J. Schacter, In: *Baun AL*, eg. *Microbiology of Chlamydia*, Boca Raton, Fla., CRC Press, 1988, pp. 153–165).

The current therapy for suspected/confirmed *C. pneumoniae* infection is with a short course (e.g., 2–3 weeks) of a single antibiotic. *C. pneumoniae* is susceptible in vitro to tetracyline, erythromycin, clarithromycin, and fluoroquinolones such as ofloxacin and sparfloxacin (Kuo et al., *Antimicrob Agents Chemother* 32:257–258 (1988); Welsh et al., *Antimicrob Agents Chemother* 36:291–294 (1992); Chirgwin et al., *Antimicrob Agents Chemother* 33:1634–1635 (1989); Hammerschlag et al., *Antimicrob Agents Chemother* 36:682–683 (1992); Hammerschlag et al., *Antimicrob Agents Chemother* 36:1573–1574); M. R. Hammerschlag, *Antimicrob Agents Chemother* 38:1873–1878 (1994); M. R. Hammerschlag, *Infect. Med.* pp. 64–71 (1994)). Despite this demonstration of in vitro susceptibility, *C. pneumoniae* infections may relapse following antibiotic therapy with these agents. In vitro studies on the persistence of Chlamydiae despite specific and appropriate antibiotic therapy have suggested that the presence of antibiotics promotes the formation of an intracellular, non-replicative state (Beatty et al., *Microbiol Rev.* 58:686–699 (1994)), typically referred to as the latent or cryptic phase. This change can be thought of as a stringent response and is seen also with nutrient starvation and exposure to γ-interferon. Removal of the stressful influence allows the organism to resume replication. Thus, in this way, the organism can escape current antibiotic therapy used in clinical practice.

In view of the chronic and persistent nature of chlamydial infections, there is a need for reliable, accurate methods for diagnosis of pathogenic infection as well as therapeutic approaches to manage the infection. Due to the highly infective nature of Chlamydia EBs and their ability to reinfect cells, there is also a need for antichlamydial therapy which totally eradicates this pathogen, thereby preventing the long term sequelae of such chronic infections.

SUMMARY OF THE INVENTION

The present invention provides a unique approach for the diagnosis and management of infection by Chlamydia species, particularly *C. pneumoniae*. The invention is based upon the discovery that a combination of agents directed toward many of the various stages of the chlamydial life cycle can successfully manage infection and ultimately prevent reinfection/reactivation of the pathogen. Accordingly, one embodiment of the invention pertains to methods of treating infection by a Chlamydia species, comprising administering to an individual in need thereof a combination of antichlamydial agents, comprising at least two agents, each of which is targeted against a different phase of the chlamydial life cycle. For example, the method can be carried out using agents chosen from among the following groups: a) at least one agent targeted against the elementary body phase of the chlamydial life cycle; b) at least one agent targeted against the replicating phase of the chlamydial life cycle; arid c) at least one agent targeted against a cryptic phase of the chlamydial life cycle. The chlamydial pathogen can be eliminated more rapidly when a combination comprising agents targeted against each phase of the chlamydial life cycle is administered.

The invention also pertains to novel combinations of antichlamydial agents and to novel pharmaceutical compositions including at least two antichlamydial agents, each of which is targeted against a different phase of the chlamydial life cycle. For example, the agents can be selected from the group consisting of: a) at least one agent targeted against the elementary body phase of the chlamydial life cycle; b) at least one agent targeted against the replicating phase of the chlamydial life cycle; and c) at least one agent targeted against a cryptic phase of the chlamydial life cycle. These compositions and combinations of agents can further comprise one or a combination of adjunct compounds, including anti-inflammatory agents, immunosuppressive agents and anti-porphyrial agents. Use of the combination of antichlamydial agents or compositions thereof for the manufacture of a medicament for the management of Chlamydia infection is also described. In a particular embodiment, the agents can be assembled individually, admixed or instructionally assembled.

The invention also pertains to a novel therapy comprising a specific agent targeted against the elementary body phase of the chlamydial life cycle which, if used for a sufficient period of time, allows active infection to be completed without the creation of infectious EBs.

In order to facilitate patient compliance during a course of therapy, the invention provides a means for packaging therapeutic agents, described herein, for the management of Chlamydia infection. For example, a pack can comprise at least two different agents, each of which is targeted against a different phase of the chlamydial life cycle. These agents can be selected from the group consisting of: a) at least one agent targeted against the elementary body phase of the chlamydial life cycle; b) at least one agent targeted against the replicating phase of the chlamydial life cycle; and c) at least one agent targeted against a cryptic phase of the chlamydial life cycle. Optional adjunct compounds, as mentioned previously, can likewise be present in the pack. A preferred pack will comprise a plurality of agents that are targeted at two, but preferably to all, of the stages of the chlamydial life cycle. The pack can provide a unit dosage of the agents or can comprise a plurality of unit dosages, and may be labeled with information, such as the mode and order of administration (e.g., separate, simultaneous or sequential) of each component contained therein.

The invention also encompasses a method for evaluating the infection status of an individual and/or the progress of therapy in an individual undergoing therapy for infection caused by Chlamydia. The method comprises quantifying antibody titer or other measure to the pathogen and comparing the measure to antibody measure quantified at a time earlier in the therapy, whereby the difference between the measures is indicative of the progress of the therapy. The invention also pertains to a method for monitoring the course of therapy for treating infection by Chlamydia, comprising determining presence or absence of Chlamydia in an infected individual at time intervals during course of therapy. In a particular embodiment, this is determined by PCR assay for pathgen DNA or antigen capture assay for pathogen.

Detection of the presence of Chlamydia in a sample of biological material taken from an individual thought to be infected therewith is important in determining the course of therapy and the agents to be used. This can be achieved by detecting the presence of DNA encoding MOMP of Chlamydia or other chlamydial genes in the individual. In one aspect of the invention, diseases associated with Chlamydia infection, such as inflammatory diseases, autoimmune diseases and diseases in which the individual is immunocompromised, can be treated by managing (i.e., significantly reducing infection or eradicating) the Chlamydia infection using the novel approach described herein. Both clinical and serological improvements/resolutions in patient status have been demonstrated.

The invention also pertains to a susceptibility test for identifying agent(s) capable of significantly reducing/eliminating chlamydial infection. The method comprises preparing tissue culture from cell lines; inoculating these cells with Chlamydia in the absence of cycloheximide; allowing the Chlamydia to infect these cells for several days; adding agent(s) to be tested, which agent(s) is/are replaced as needed for the duration of incubation; isolating chlamydial nucleic acid from the cells; and assessing the presence or absence of chlamydial DNA using a suitable nucleotide amplification assay, such as PCR. Preferably the presence or absence of signal for amplified DNA encoding MOMP of Chlamydia or other chlamydial protein is determined. Absence of a signal indicates a reduction in the degree of infection below that which is detectable by nucleic acid amplification techniques and strongly suggests eradication of the microorganism. The susceptibility tests described herein are particularly useful as a drug screening tool for assessing the activity of single agents or combinations of agents against Chlamydia infection.

The unique and novel aspect of the susceptabilty test described herewithin is that it measures the presence or absence of chlamydial DNA and thus can detect cryptic forms and/or elementary bodies both of which are viable, yet are not replicating.

In one embodiment, a suitable nucleotide assay for identifying agents effective against a cryptic form of chlamydia comprises, in the presence of agent(s) to be tested, is performed by subjecting cultured cells to protease/reducing agent (e.g., dithiotreitol (DTT)) and protease digestion or guanidine isothiocyanate (also known as guanidine thiocyanate) for a prescribed period of time; extracting DNA from the treated solution; exposing DNA to appropriate polymerase, dNTPs and primers for DNA amplification of MOMP or other protein of the Chlamydia species; and determining the presence or absence of amplified DNA by visualizing the ethidium bromide treated DNA product by gel electrophoresis, for example. In particular embodiments, the Chlamydia species is *C. pneumoniae* and the appropriate primers are CHLMOMPDB2 and CHLMOMPCB2.

The invention further relates to a method of identifying cells containing a cryptic form of a Chlamydia species by a nucleic acid amplification technique (e.g., PCR) comprising subjecting cultured cells to protease digestion; stopping protease activity; exposing cells to appropriate heat-stable DNA polymerase, dNTPs and labeled primers (e.g., 3'-biotin labeled, 5'-biotin labeled) for amplification of DNA encoding MOMP of the Chlamydia species; washing the cells; exposing the cells to a reporter molecule (e.g., strepavidin-conjugated signal enzyme); exposing the cells to an appropriate substrate for the reporter molecule (e.g., conjugated enzyme); and visualizing the amplified DNA encoding MOMP by visualizing the product of the reaction.

A method of identifying cells containing a cryptic form of Chlamydia comprises treating cultured cells, thought to be infected with Chlamydia, with a disulfide reducing agent; subjecting cultured cells to protease digestion; exposing cells to appropriate polymerase, dNTPs and primers for DNA amplification of nucleic acid encoding a chlamydial protein; exposing the cells to a reporter molecule enzyme; exposing the cells to an appropriate substrate for the reporter enzyme; and determining the presence of a cryptic form of Chlamydia by visualizing the amplified DNA encoding a chlamydial protein. Preferably the amplification technique is PCR and the primers are CHLMOMPDB2 and CHLMOMPCB2 of *Chlamydia pneumoniae*.

A similar method can be used as an assay for identifying an agent which is effective against a cryptic form of Chlaniydia. Accordingly, the method comprises treating cultured cells grown in the absence of cycloheximide, thought to be infected with Chlamydia, with a disulfide reducing agent; allowing the chlamydia to replicate; adding a test agent; subjecting cultured cells to protease digestion; exposing cells to appropriate polymerase, dNTPs and primers for DNA amplification of a chlamydial protein; exposing the cells to a reporter molecule enzyme; exposing the cells to an appropriate substrate for the reporter enzyme; and determining the presence of a cryptic form of Chlamydia by visualizing the amplified DNA encoding a chlamydial protein, such as MOMP.

Also described is a method of detecting chlamydial elementary bodies in a sample comprising contacting the sample with a disulfide reducing agent before using a DNA amplification technique to detect chlamydial DNA in the sample.

The present invention pertains to methods for clearing biological material infected with Chlamydia to produce Chlamydia-free cell lines and animals, and to methods of maintaining biological material, e.g, cell lines and animals, such that they remain Chlamydia-free. According to the method, a biological material is cleared from Chlamydia infection by contacting the biological material with at least two agents but preferably three agents, each of which is targeted against a different phase of the chlamydial life cycle, until the biological material no longer tests positive for Chlamydia. The agents can be selected from the group consisting of a) agents targeted against a cryptic phase of the chamydial life cycle; b) agents targeted against the elementary body phase of the chlamydial life cycle; and c) agents targeted against the replicating phase of the chlamydial life cycle. In one embodiment, the agent targeted against the elementary body phase is a disulfide reducing agent. In another embodiment, the agent targeted against a cryptic phase is a nitroaromatic compound, such as nitroimidazoles, nitrofluans, analogs, derivatives and combinations thereof.

Biological material that has been cleared of Chlamydia infection, according to the methods of this invention, are also described. The biological material can be a continuous cell line such as HeLa-CF, HL-CF, H-292-CF, HuEVEC-CF and McCoy-CF; wherein "CF" is a shorthand annotation for "Chlamydia-free"). Alternatively, the biological material can be an animal, such as a mouse, rabbit or other animal model, which is negative for Chlamydia.

The invention also pertains to methods of maintaining a Chlamydia-free status in animals and cell lines which have been cleared of Chlamydia infection by the methods of this invention, or have never been infected, such as their Chlamydia-free offspring or progeny. Cells or animals can be maintained as Chlamydia-free by maintaining them on antibiotics and/or treating their nutrients and environment to ensure that they are Chlamydia-free. Particularly, a source of nutrients to be administered to Chlamydia-free cells or animals can be treated to inactivate or remove any chlamydial elementary bodies therefrom. This can be accomplished.by exposing the nutrients to gamma irradiation for a period of time and level of exposure adequate to inactivate the elementary bodies. In addition to, or alternatively, a source of nutrients can be passed through a filtration system to physically remove the chlamydial elementary bodies therefrom. Optionally, the source of nutrients can be first treated with a disulfide reducing agent, such as dithiothreitol, before the filtration step is performed. The filter should be of adequate size such that objects larger than 0.5 microns are prevented from passing through.

The invention further pertains to a diagnostic kit or pack comprising an assembly of materials selected from the group consisting of antibiotics, reagents, Chlamydia-free cell lines, and combinations thereof, or other materials that would be necessary to perform any of the methods described herein.

The invention further relates to a method of detecting viable Chlamydia in a biological material suspected of being contaminated therewith, comprising culturing Chlamydia-free cells or animals in the presence of biological material and then determining the presence or absence of viable Chlamydia in the culture.

The invention also pertains to a method for differentiating porphyria caused by Chlamydia species from porphyria caused by a genetic disorder. The method comprises measuring peripheral red blood cell enzymes and/or performing a fecal and/or urinary porphyrin screen, wherein if the peripheral red blood cell enzymes are normal or elevated and fecal/urinary screen are elevated in one or more components of the heme pathway, the porphyria is not caused by a genetic disorder and may be caused by Chlamydia. The invention relates to a method for diagnosing secondary porphyria caused by Chlamydia in an individual having symptoms associated therewith, comprising determining the presence or amount of obligatory enzymes in heme biosynthesis in red blood cells of the individual and determining the presence of Chlamydia in the individual. The invention further relates to a method for differentiating secondary porphyria caused by Chlamydia from that caused by a genetic disorder in an individual, comprising treating infection by Chlamydia at many stages of its life cycle and then assessing whether porphyrins have been reduced, wherein a decrease in the porphyrin levels is indicative that the porphyria is secondary and caused by Chlamydia.

The subject invention also pertains to a method for treating porphyria caused by Chiamydia in an individual in need thereof, comprising reducing the levels of active stage, latent stage and elementary bodies of the pathogen from the individual and administering one or more compounds which reduce adverse effects associated with secondary porphyria. In one embodiment, the method additionally comprises administering a compound which reduces the adverse effects of porphyrins associated with porphyria. In a particular embodiment, the compound is cimetidine. This method can also be valuably combined with additional steps, including at least one of administering antioxidants; orally administering activated charcoal; administering a ihigh carbohydrate diet regimen; administering hydroxychloroquine; administering benzodiazepine drugs; performing hemodialysis; performing plasmaphoresis; and adminstering chelating agents; and administering intravenous hematin.

The invention also pertains to a method of detecting elevated porphyrin levels in an individual by testing that individual for antibodies to porphyrins. The invention also pertains to diagnosing deficiency by detecting antibodies to B-12. Monoclonal and polyclonal antibodies to prophyrins and/or Vitamin B12 can be produced.

The invention further pertains to a method which can be automated using a computerized system, for example, to formulate a drug therapy for management of infection caused by Chlamydia. The method comprises determining targets within the chlamydial life cycle, for each determined target, identifying agents that are active against the target; and combining at least a subset of the identified agents to provide a combination therapy for management of infection caused by Chlamydia, the agents in said subset individually being active against different targets in the life cycle of Chlamydia. The targets include identifying phases of the chlamydial life cycle and for each identified life cycle phase, determining at least one vulnerable aspect of the organism during that life cycle phase, each said determined vulnerable aspect defining a target within the chlamydial life cycle. Agents identified by the method are then tested using the susceptability testing procedure described herein and initial dosages for combination agents are set based on pharmacokenetics and pharmacodynamics for the agents prescribed individually, said setting initial dosage including modifying the combination dosage according to results of the susceptability testing and in vivo efficacy.

The invention also relates to a method of purifying a blood sample, comprising subjecting the blood sample to hemodialysis or plasmaphoresis; in particular, the plasmaphoresis is carried out using a plasmaphoresis apparatus utilizing a sulfone-containing filter or a charcoal-containing filter. The blood sample can be obtained from a blood bank or repository.

BRIEF DESCRIPTION OF THE DRAWINGS

FIGS. 1A and 1B show a sequence alignment of various Chlamydia MOMPs.

FIG. 4 illustrates the peptide amino acid sequences employed for the construction of peptide based ELISAs with species specificity for VD1.

FIG. 5 illustrates the peptides for VD2 which are used similarly to the VD1 sequences.

DETAILED DESCRIPTION OF THE INVENTION

Figures 2, 3:
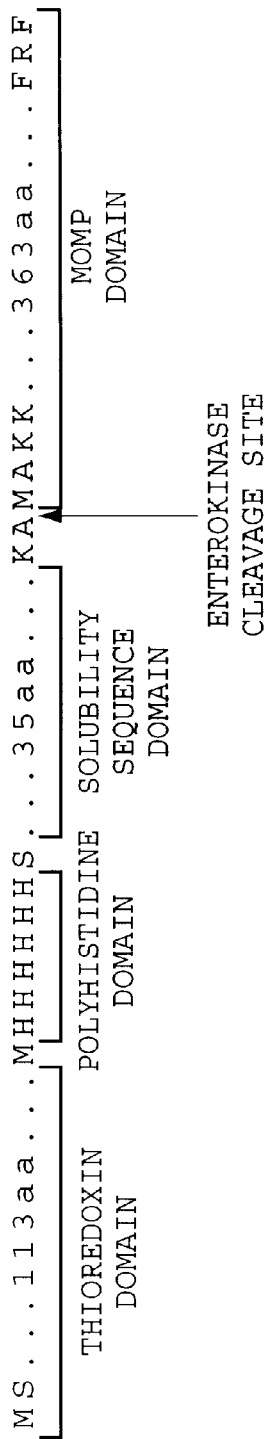
FIG. 2 shows the expressed thioredoxin fusion protein containing a polyhistidine affinity chromatography site, an enterokinase cleavage site, and the full length MOMP protein with an alanine insertion after aa1. Amino to carboxyl reads left to right. Total amino acid content in the expressed protein is 530 residues.
FIG. 3 illustrates the constant and variable domain (VD) of various Chlamydia species.

This invention describes specific antichlamydial agents that are used singly or in combination to eliminate or interfere with more than one of the distinct phases of the life cycle of Chlamydia species. These chlamydial phases include the intracellular metabolizing/replicating phase; the intracellular "cryptic" phases; and the extracellular EB phase. Current concepts of susceptibility testing for chlamydiae and antimicrobial therapy for their associated infections address only one phase, the replicating phase. Unless multiple phases of the life cycle are addressed by antichlamydial therapy, the pathogen is likely to escape the desired effects of the antimicrobial agent(s) used and cause recurrent infection after reactivation from latency. For the purposes of this invention, "cryptic phase" embraces any non-replicating, intracellular form, of which there are a number of distinct stages, including but not limited to intracellular EBs, EBs transforming into RBs and vice versa, miniature RBs, non-replicating RBs and the like.

Diagnostic and therapeutic methods for the management of Chiamydia infections are described in detail below. For the purposes of this invention, "management of Chlamydia infection" is defined as a substantial reduction in the presence of all phases/forms of Chlamydia in the infected host by treating the host in such a way as to minimize the sequellae of the infection. Chlamydia infections can thus be managed by a unique approach referred to herein as "combination therapy" which is defined for the purpose of this application as the administration of multiple agents which together are targeted at least two but preferably many of the multiple phases of the chlamydial life cycle, each agent taken separately, simultaneously or sequentially over the course of therapy. When used alone, these agents are unable to eliminate or manage chlamydial infection. The diagnostic methods and combination therapies described below are generally applicable for infection caused by any Chlamydia species, including but not limited to *C. pneumoniae, C. trachomatis, C. psittaci* and *C. pecorum*. Infections in which the causative agent is *C. pneumoniae* are emphasized.

Antichlamydial agents, which have been identified as effective against Chlamydia by the susceptibility testing methods described herein, can be used singly to affect Chlamydia in a single stage of its life cycle or as part of a combination therapy to manage Chlamydia infection. For example, compounds identified as anti-cryptic phase drugs, anti-EB phase drugs, anti-DNA-dependent RNA polymerase drugs and nicotinic acid cogener drugs can be used alone or in combination to eliminate, reduce or prevent one or more of the distinct phases of the chlamydial life cycle. Certain of these compounds have not heretofore been shown to have antichlamydial activity.

Diagnosis of Chlamydia Infection

The invention pertains to methods for diagnosing the presence of Chlamydia in a biological material, as well as to the use of these methods to evaluate the serological status of an individual undergoing antichlamydial combination therapy. For purposes of this application, "biological material" includes, but is not limited to, bodily secretions, bodily fluids and tissue specimens. Examples of bodily secretions include cervical secretions, trachial-bronchial secretions and pharyngeal secretions. Suitable bodily fluids include blood, sweat, tears, cerebral spinal system fluid, serum, sputum, ear wax, urine, snyovial fluid and saliva. Animals, cells and tissue specimens such as from a variety of biopsies are embraced by this term.

In one embodiment, peptide-based assays are disclosed for the detection of one or more immunoglobulins, such as IgG, IgM, IgA and IgE, against antigenic determinants within the full length recombinant MOMPs of various Chlamydia species. Detection of IgG and/or IgM against antigenic determinants within the full length recombinant MOMP of *C. pneumoniae* is preferred. IgA determinations are useful in the analysis of humoral responses to Chlamydia in secretions from mucosal surfaces (e.g., lung, GI tract, gerontourinary tract. etc.). Similarly, IgE determinations are useful in the analysis of allergic manifestatins of disease. Table 1 below provides the GenBank Accession numbers of various MOMPs for Chlamydia species.

TABLE 1

| Species | Strain | ID | GenBank Accession No. |
|---|---|---|---|
| C. trachomatis | A | CTL/A | M33636 |
| C. trachomatis | A | CTL/A | M58938 |
| | | | M33535 |
| C. trachomatis | A | CTL/A | J03813 |
| C. trachomatis | B | CTL/B | M33636 |
| C. trachomatis | C | CTL/L | M17343 |
| | | | M19128 |
| C. trachomatis | D | CTL/D | A27838 |
| C. trachomatis | E | CTL/E | X52557 |
| C. trachomatis | F | CTL/F | X52080 |
| | | | M30501 |
| C. trachomatis | H | CTL/H | X16007 |
| C. trachomatis | L1 | CTL/L1 | M36533 |
| C. trachomatis | L2 | CTL/L2 | M14738 |
| | | | M19126 |
| C. trachomatis | L3 | CTL/L3 | X55700 |
| C. trachomatis | Mouse Pneumo | CTL/MP | X60678 |
| C. pecorum | Ovine Polyarthritis | CPC/OP | Z18756 |
| C. psittaci | Strain 6BC | CPS/6B | X56980 |
| C. psittaci | Feline | CPS/F | X61096 |
| C. trachomatis | Da | CTL/DA | X62921 |
| | | | S45921 |
| C. pneumoniae | TWAR | CPN/HU1 | M64064 |
| | | | M34922 |
| | | | M64063 |
| C. pneumoniae (? C. pecorum) | Horse | CPN/EQ2 | L04982 |
| C. pneumoniae | TWAR | CPN/MS | not assigned |
| C. psittaci | Horse | CPS/EQ1 | L04982 |

For example, a biological material, such as a sample of tissue and/or fluid, can be obtained from an individual and a suitable assay can be used to assess the presence or amount of chlamydial nucleic acids or proteins encoded thereby. Suitable assays include immunological methods such as enzyme-linked immunosorbent assays (ELISA), including luminescence assays (e.g., fluorescence and chemiluminescence), radioimmunoassay, and immunohistology. Generally, a sample and antibody are combined under conditions suitable for the formation of an antibody-protein complex and the formation of antibody-protein complex is assessed (directly or indirectly). In all of the diagnostic methods described herein, the antibodies can be directly labeled with an enzyme, fluorophore, radioisotope or luminescer. Alternatively, antibodies can be covalently linked with a specific scavenger such as biotin. Subsequent detection is by binding avidin or strepavidin labeled with an indicator enzyme, flurophore, radioisotope, or luminescer. In this regard, the step of detection would be by enzyme reaction, fluorescence, radioactivity or luminescence emission, respectively.

The antibody can be a polyclonal or monoclonal antibody, such as anti-human monoclonal IgG or anti-human monoclonal IgM. Examples of useful antibodies include mouse anti-human monoclonal IgG that is not cross reactive to other immunoglobulins (Pharmagen; Clone G18-145, Catalog No. 34162D); mouse anti-human monoclonal IgM with no cross reactivity to other immunoglobulins (Pharmagen; Clone G20-127, Catalog No. 34152D). Peptide-based immunoassays can be developed which are Chlamydia specific or provide species specificity, but not necessarily strain specificity within a species, using monoclonal or polyclonal antibodies that are not cross-reactive to antigenic determinants on MOMP of a chlamydial species not of interest.

Recombinant-based immunological assays have been developed to quantitate the presence of immunoglobulins against the Chlamydia species. Full length recombinant Chlamydia MOMP can be synthesized using an appropriate expression system, such as in E. coli or Baculovirus. The expressed protein thus serves as the antigen for suitable immunological methods, as discussed above. Protein-based immunological techniques can be designed that are species- and strain-specific for various Chlamydia.

Diagnosis of chlamydial infection can now be made with an improved IgM/IgG C. pneumoniae method of quantitation using ELISA techniques, Western blot confirmation of ELISA specificity and the detection of the MOMP gene of C. pneumoniae in serum using specific amplification primers that allow isolation of the entire gene for analysis of expected strain-specific differences.

Any known techniques for nucleic acid (e.g., DNA and RNA) amplification can be used with the assays described herein. Preferred amplification techniques are the polymerase chain reaction (PCR) methodologies which comprise solution PCR and in situ PCR, to detect the presence or absence of unique genes of Chlamydia. Species-specific assays for detecting Charnydia can be designed based upon the primers selected. Examples of suitable PCR amplification primers are illustrated below in Table 2. Examples of preferred primers are illustrated in Table 3.

TABLE 2

Initial and Terminal Nucleotide Sequences of Chlamydial MOMP Genes in which entire sequence is known

| GenBank Accession No. | ID | Initial Fifty Nucleotides | SEQ ID NO. |
|---|---|---|---|
| M64064/M34922/M64063 | CPNHU1 | ATGAAAAAACTCTTAAAGTCGGCGTTATTATCCGCCGCATTTGCTGGTTC | 1 |
| None | CPNHU2[a] | ATGAAAAAACTCTTAAAGTCGGCGTTATTATCCGCCGCATTTGCTGGTTC | 2 |
| L04982 | CPNEQ1 | ATGAAAAAACTCTTGAAGTCGGCATTATTGTTTGCCGCTACGGGTTCCGC | 3 |
| L04982 | CPNEQ2 | ATGAAAAAACTCTTAAAGTCGGCGTTATTATCCGCCGCATTTGCTGGTTC | 4 |
| X56980 | CPS/6B | ATGAAAAAACTCTTGAAATCGGCATTATTGTTTGCCGCTACGGGTTCCGC | 5 |
| M36703 | CPS/AB1 | ATGAAAAAACTCTTGAAATCGGCATTATTGTTTGCCGCTACGGGTTCCGC | 6 |
| L39020 | CPS/AB2 | ATGAAAAAACTCTTGAAATCGGCATTATTGTTTGCCGCTACGGGTTCCGC | 7 |
| L25436 | CPS/AV/C | ATGAAAAAACTCTTGAAATCGGCATTATTATTTGCCGCTACGGGTTCCGC | 8 |
| X61096 | CPS/F | ATGAAAAAACTCTTAAAATCGGCATTATTATTTGCCGCTGCGGGTTCCGC | 9 |
| M33636/N58938/J03813 | CTL/A | ATGAAAAAACTCTTGAAATCGGTATTAGTATTTGCCGCTTTGAGTTCTGC | 10 |
| M17343/M19128 | CTL/C | ATGAAAAAACTCTTGAAATCGGTATTAGTATTTGCCGCTTTGAGTTCTGC | 11 |
| X62921/S45921 | CTL/DA | ATGAAAAAACTCTTGAAATCGGTATTAGTATTTGCCGCTTTGAGTTCTGC | 12 |
| X52557 | CTL/E | ATGAAAAAACTCTTGAAATCGGTATTAGTATTTGCCGCTTTGAGTTCTGC | 13 |
| X52080/M30501 | CTL/F | ATGAAAAAACTCTTGAAATCGGTATTAGTATTTGCCGCTTTGAGTTCTGC | 14 |
| X16007 | CTL/H | ATGAAAAAACTCTTGAAATCGGTATTAGTATTTGCCGCTTTGAGTTCTGC | 15 |

TABLE 2-continued

Initial and Terminal Nucleotide Sequences of Chlamydial MOMP Genes in which entire sequence is known

| | | | | |
|---|---|---|---|---|
| M36533 | | CTL/L1 | ATGAAAAAACTCTTGAAATCGGTATTAGTGTTTGCCGCTTTGAGTTCTGC | 16 |
| M14738/M19126 | | CTL/L2 | ATGAAAAAACTCTTGAAATCGGTATTAGTGTTTGCCGCTTTGAGTTCTGC | 17 |
| X55700 | | CTL/L3 | ATGAAAAAACTCTTGAAATCGGTATTAGTGTTTGCCGCTTTGAGTTCTGC | 18 |
| X60678 | | CTL/MP | ATGAAAAAACTCTTGAAATCGGTATTAGCATTTGCCGTTTTGGGTTCTGC | 19 |

| Chlamydial | | | | SEQ ID |
|---|---|---|---|---|
| Species | Strain | ID | Terminal Fifty Nucleotides | NO. |
| C. pneumoniae | TWAR | CPNHU1 | GTTTAATTAACGAGAGAGCTGCTCACGTATCTGGTCAGTTCAGATTCTAA | 20 |
| C. pneumoniae | MS | CPNHU2 | GTTTAATTAACGAGAGAGCTGCTCACGTATCTGGTCAGTTCAGATTCTAA | 21 |
| C. psittaci | Horse | CPNEQ1 | CAACGTTAATCGACGCTGACAAATGGTCAATCACTGGTGAAGCACGCTTA | 22 |
| C. pneumoniae | Horse | CPNEQ2 | GTTTAATTAACGAGAGAGCTGCTCACATATCTGGTCAGTTCAGATTCTAA | 23 |
| C. psittaci | SBE | CPS/6B | AACGTTAATCGACGCTGACAAATGGTCAATCACTGGTGAAGCACGCTTAA | 24 |
| C. psittaci | Ewe abortion | CPS/AB1 | AACGTTAATCGACGCTGACAAATGGTCAATCACTGGTGAAGCACGCTTAA | 25 |
| C. psittaci | Bovine abortion | CPS/AB2 | GCTTAATCAATGAAAGAGCCGCTCACATGAATGCTCAATTCAGATTCTAA | 26 |
| C. psittaci | Avian | CPS/AV/C | GCTTAATCAATGAAAGAGCTGCTCACATGAATGCTCAATTCAGATTCTAA | 27 |
| C. psittaci | Feline | CPS/F | GCTTAATCGACGAAAGAGCTGCTCACATTAATGCTCAATTCAGATTCTAA | 28 |
| C. trachomatis | Hu/A | CTL/A | CGCAGTTACAGTTGAGACTCGCTTGATCGATGAGAGAGCAGCTCACGTAA | 29 |
| C. trachomatis | Hu/C | CTL/C | GCTTGATCGATGAGAGAGCAGGTCACGTAAATGCACAATTCCGGTTCTAA | 30 |
| C. trachomatis | Hu/Da | CTL/DA | GCTTGATCGATGAGAGAGCAGCTCACGTAAATGCACAATTCCGCTTCTAA | 31 |
| C. trachomatis | HU/E | CTL/E | CGCTTGATCGATGAGAGACTGCTCACGTAAATGCACAATTCCGCTTCTAA | 32 |
| C. trachomatis | Hu/F | CTL/F | GCTTGATCGATGAGAGAGCTGCTCACGTAAATGCACAATTCCGCTTCTAA | 33 |
| C. trachomatis | Hu/H | CTL/H | GCTTGATCGATGAGAGAGCAGCTCACGTAAATGCACAATTCCGCTTCTAA | 34 |
| C. trachomatis | Hu/L1 | CTL/Li | GCTTGATCGATGAGAGAGCTGCTCACGTAAATGCACAATTCCGCTTCTAA | 35 |
| C. trachomatis | Hu/L2 | CTL/L2 | GCTTGATCGATGAGAGAGCTGCTCACGTAAATGCACAATTCCGCTTCTAA | 36 |
| C. trachomatis | Hu/L3 | CTL/L3 | GCTTGATCGATGAGAGAGCAGCTCACGTAAATGCACAATTCCGCTTCTAA | 37 |
| C. trachomatis | Mouse | CTL/MP | GCTTGATCGATGAAAGAGCAGCTCACGTAAATGCTCAGTTCCGTTTCTAA | 38 |

[a]Sequence from a cerebral spinal fluid of a patient with multiple sclerosis isolated by the inventors. Sequence is identical to TWAR C. pneumoniae with exception of a C/T mutation at NT 54 and a G/A mutation at NT 126.
[b]Terminator condon underlined

TABLE 3

Primers for PCR Amplification of Entire MOMP Gene[a]

| Chlamydia | | | | | SEQ ID |
|---|---|---|---|---|---|
| Species | Strain | ID | Sequence | $T_m$[b] | NO. |
| | | | Plus Strand Primer | | |
| C. pneumoniae | TWAR | CHLMOMP DB2 | ATGAAAAAAC TCTTAAAGTC GGCGTTATTA TCCGCCGC | 61.4° | 105 |
| C. trachomatis | L2 | CTMOMP L2DB | ATGAAAAAAC TCTTGAAATC GGTATTAGTG TTTGCCGCTT TGAG | 61.2° | 106 |
| C. psittaci | Feline | PSOMP FPN_D | ATGAAAAAAC TCTTAAAATC GGCATTATTA TTTGCCGCTG CGGG | 62.1° | 107 |
| C. psittaci | 6BC | PSOMP 6BC_b | ATGAAAAAAC TCTTGAAATC GGCATTATTG TTTGCCGCTA CGGG | 63.0° | 108 |
| C. trachomatis | Mouse | CTMU MOMP_D | ATGAAAAAAC TCTTGAAATC GGTATTAGCA TTTGCCGTTT TGGGTTCTGC | 63.5° | 109 |
| | | | Minus Strand Primer | | |
| C. pneumoniae | TWAR | CHLMOMP CB2 | TTAGAATCTG AACTGACCAG ATACGTGAGC AGCTCTCTCG | 64.4° | 110 |
| C. trachomatis | L2 | CTMOMP L2CB | TTAGAAGCGG AATTGTGCAT TTACGTGAGC AGCTC | 61.5° | 111 |
| C. psittaci | Feline | PSOMP FPN_C | TTAGAATCTG AATTGAGCAT TAATGTGAGC AGCTCTTTCG TCG | 62.2° | 112 |
| C. psittaci | 6BC | PSOMP GBC_C | TTAGAATCTG AATTGACCAT TCATGTGAGC AGCTCTTTCA TTGATTAAGC G | 63.4° | 113 |
| C. trachomatis | Mouse | CTMU MOMP_C | TTAGAAACGG AACTGAGCAT TTACGTGAGC TGCTCTTTCA TC | 63.2° | 114 |

[a]All primers amplify under identical amplification conditions: 94° C. for 1 min., 58° C. for 2 min., 74° C. for 3 min., for 35 cycles with 72° C. for 10 min. extension of last cycle.
[b]Melting temperature in degrees Celsius of a nucleic acid isomer based on the equation of Mermur and Doty (J. Mol. Biol. 5: 109–118, 1962) where $T_m = 81.5 + 16.6 \log_{10} (Na^+/K^+) + 41 (GC) - 600/L$ where $(Na^+/K^+)$ in the molar cation concentration, GC in the mole fraction of GC and L is the sequence fragment length. $(Na^+/K^+)$ used for computation was 0.05M.

Ligase chain reaction can also be carried out by the methods of this invention; primers/probes therefor can be constructed using ordinary skill. Amplification of the entire MOMP gene is useful for mutational analysis and the production of recombinant MOMP. Shorter primers can be used for specific amplification of most of the MOMP genome with a modification of amplification protocol. For example, a 22 bp negative strand primer of the sequence 5'-CAGATACGTG AGCAGCTCTC TC-3'(CPNMOMPC; SEQ ID NO. 39) with a computed $T_m=55°$ plus a 25 bp positive strand primer of the sequence 5'-CTCTTAAAGT CGGCGTTATT ATCCG-3'(CPNMOMPD; SEQ ID NO. 40) with a computed $T_m=53.9°$ can be used as a primer pair by adjusting the hybridization step in the amplification protocol (Table 2) from 58° C. to 50° C. Similarly, smaller regions of MOMP can be amplified by a large variety of primer pairs for diagnostic purposes although the utility of strain identification is reduced and amplification may be blocked if one or both primer pairs hybridize to a region that has been mutated. Extensive experience with the full length MOMP PCR amplification indicates that mutational events within the CHLMOMPDB2 and CHLMOMPCB2 hybridization sites are rare or non-existent.

The nucleic acid amplification techniques described above can be used to evaluate the course of antichlamydial therapy. The continued absence of detectable chlamydial DNA encoding MOMP as a function of antichlamydial therapy is indicative of clinical management of the chlamydial infection. Serological improvement can be based upon the current serological criteria for eradication of chronic Chlamydia reported below in Table 4.

TABLE 4

Serological Criteria for Eradication of Chronic *Chlamydia pneumoniae* Infection

| | |
|---|---|
| IgM | $\leq$1:25 |
| IgG | Stable titer 1:100 |
| PCR | Negative |

Preferred PCR techniques are discussed in detail below in the Example Section. In general, solution PCR is carried out on a biological material by first pre-incubating the material in an appropriate reducing agent that is capable of reducing the disulfide bonds which maintain the integrity of the MOMP and other surface proteins of the chlamydial elementary bodies, thereby compromising the outer protective shell of the EBs and allowing protease penetration. Suitable disulfide reducing agents include, but are not limited to, dithiothreitol, succimer, glutathione, DL-penicillamine, D-penicillamine disulfide, 2,2'-dimercaptoadipic acid, 2,3-dimercapto-1-propone-sulfide acid. Appropriate concentrations ofthese reducing agents can be readily determined by the skilled artisan without undue experimentation using a 10 $\mu$M concentration of dithiothreitol (the preferred reducing agent) as a guideline. Failure to include a reducing agent in the initial step may prevent DNA of EBs from being isolated in the subsequent step. Data presented in Example 1 shows the effects of various reducing agents on the susceptibility of EBs to proteinase K digestion. The in vitro data shows that dithiothreitol is most effective at opening EBs for protease digestion.

Once the outer shell of the EBs has been released, the pre-incubated material is subjected to protein digestion using a protease (e.g., proteinase K), or functionally equivalent enzyme. The DNA is extracted and subjected to a nucleic acid amplification technique, e.g., PCR. The entire gene or portion thereof containing unique antigenic determinant(s) encoding MOMP or other suitable gene can then be amplified using appropriate primers flanking the gene to be amplified. For example, the gene or portion thereof can be the gene encoding MOMP, OMP-B, GRO-ES, GRO-EL, DNAK, 16S RNA, 23S RNA, the gene encoding ribonuclease-P, a 76 kd attachment protein or a KDO-transferasc gene. In an alternative method, guanidine thiocyanate, at preferably a concentration of 4M, or functionally equivalent reducing denaturant may be substituted for the disulfide reduction/protease steps.

Figure 1A:
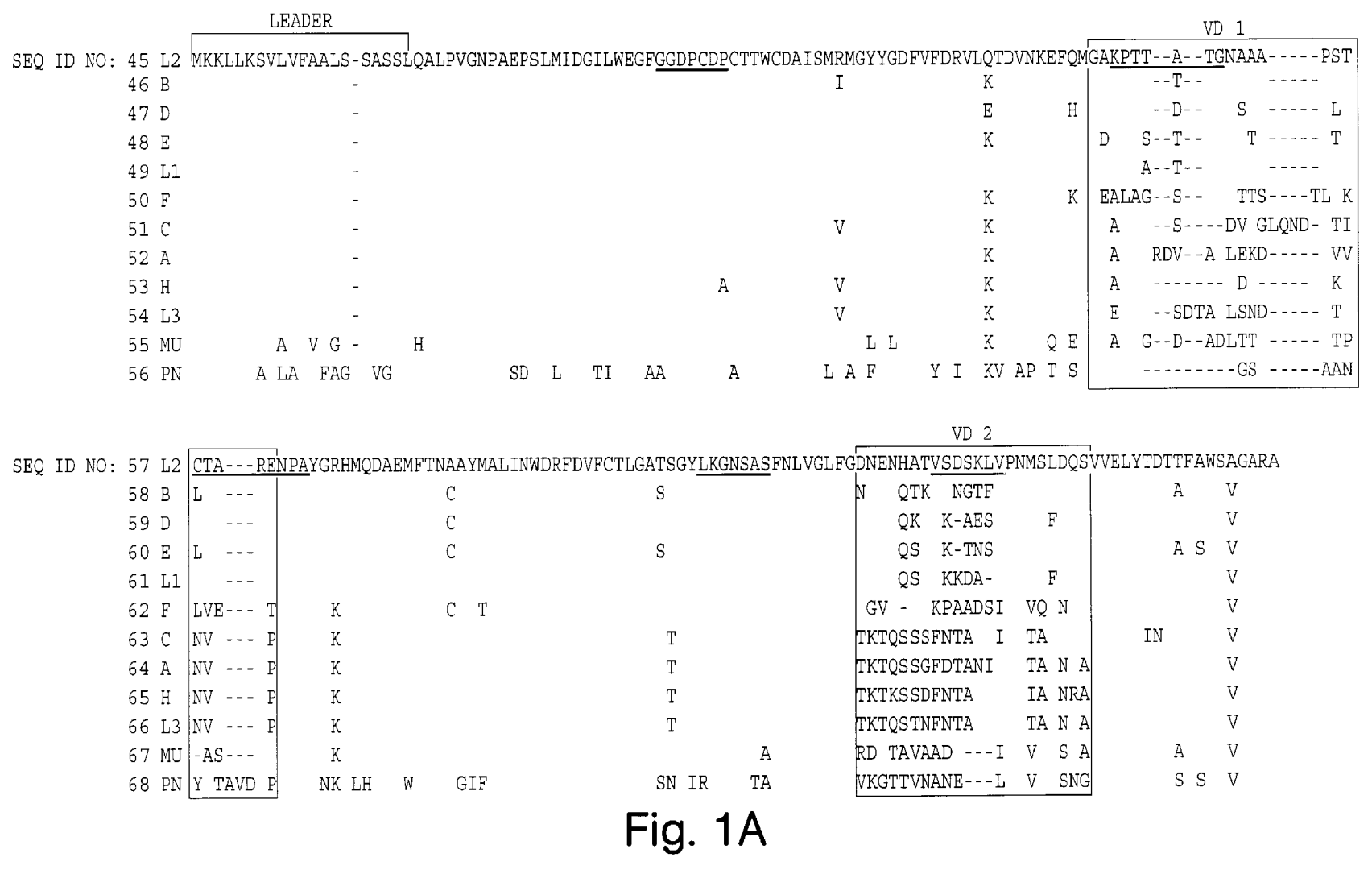

The amplified DNA is then separated and identified by standard electrophoretic techniques. DNA bands are identified using ethidium bromide staining and UV light detection. PCR primers can be designed to selectively amplify DNA encoding MOMP of a particular Chlamydia species, such as the MOMP of *C. pneumoniae, C. pecorum, C. trachomatis, C. psittaci* (See FIG. 1). Primers that are from about 15-mer to about 40-mer can be designed for this purpose.

For in situ PCR, the amplification primers are designed with a reporter molecule conjugated to the 5'-terminus. Suitable reporter molecules are well known and can be used herein. However, biotin-labeled primers are preferred. For the MOMP gene, the primers CHLMOMPDB2 and CHLMOMPCB2 have been engineered with a biotin at the 5'-terminus. For in situ PCR, using biotin labels incorporated at the 5'-terminus of the amplification primers, each DNA chain amplification results in each double strand DNA containing 2 molecules of biotin. Alternatively, other specific DNA sequences can be used, although the above-described sequence is the preferred embodiment since the large product produced (1.2 kb) prevents diffusion that may be encountered with smaller DNA amplifications. Similarly, other detection labels can be incorporated (i.e., fluorescein, for example) at the 5'-end or digoxigenin-dUTP (replacement for dTPP) can be incorporated within the amplified DNA. Alternatively to labeling the product, specific hybridization probes to constant regions of the amplified DNA can be used to identify an amplified product. This latter method has particular utility for the construction of automated laboratory equipment for solution-based PCR. For example, strepavidin-coated ELISA plates can be used to capture one or both strands of a biotin 5'-labeled DNA with detection by fluorescence of a fluorescein or other incorporated fluorophore detection probe.

Clearing and Maintaining Chlamydia-free Organisms

The present invention provides a unique approach for creating and maintaining animals and cell lines which are free of Chlamydia infection. Also described herein are methods for creating nutrients and culture media that are suitable for use with animals and cell lines that have been cleared of Chlamydia infection.

Attempts to culture isolates of *C. pneumoniae* from blood and cerebrospinal fluid (CSF) have resulted in the discovery that the continuous cell lines routinely used to cultivate *C. pneumoniae* are cryptically infected with *C. pneumoniae*. These include not only in house stocks of HeLa, HL, H-292, HuEVEC and McCoy cells, but also stocks obtained from the American Type Culture Collection (ATCC), The University of Washington Research Foundation for HL cells, as well as a commercial supplier (Bartells) of H-292 and McCoy cells for the clinical culture of Chlamydia. The presence of a cryptic form of *C. pneumoniae* in these cells has been repeatedly demonstrated by solution PCR amplifying the MOMP. In situ PCR in HeLa cells against the MOMP demonstrates the MOMP genes to be present in 100% of cells. Nevertheless, fluoroscenated mAb to LPS in McCoy cells does not yield any indication of Chlamydia (i.e., reactive against all Chiamydia) while fluoroscenated mAb to *C. pneumoniae* MOMP yields a generalized fluorescence throughout the cytoplasm that can be confused with non-specific autofluorescence. Infection with *Chlamydia trachomatis* (Bartells supply) yields the typical inclusion body staining with the LPS mab (i.e., cross reactive with all species of Chlamydia) with no change in cytoplasmic signal with anti-MOMP mAb against *C. pneumoniae*. These findings (solution PCR, in situ PCR, mAb reactivity) were interpreted as consistent with a cryptic (non-replicating) infection by *C. pneumoniae* of cells commonly used to culture the organism. Further, virtually all untreated rabbits and mice tested to date have PCR signals for the *C. pneumoniae* MOMP gene.

This creates a currently unrecognized problem of major significance for those clinical labs providing *C. pneumoniae* culture services as well as investigators who now do not know whether their results in animals or in cell culture will be affected by cryptic chlamydial contamination. Clinical and research laboratories currently have no way to determine whether an organism is, in fact, Chlamydia-free.

This invention pertains to a method for clearing cells and animals of *C. pneumoniae* and keeping them clear. Clearing them entails contacting the infected organism with agents used singly or in combination to eliminate or interfere with more than one of the distinct phases of the life cycle of Chlamydia species. Keeping them clear entails either maintaining them on antibiotics and/or treating their nutrients and environment to ensure they are Chlamydia-free. In a preferred embodiment, maintenance conditions comprise a combination of isoniazid (INH) (1 $\mu$g/ml), metronidazole (1 $\mu$g/ml), and dithiothreitol (10 $\mu$M) in the culture medium. Media changes are accomplished every 3 days or twice per week. The cells can be removed from the protective solution between 1 and 7 days before they are to be used for culture or other purpose.

These techniques have now made it possible to create a variety of Chlamydia-free (CF) organisms, including continuous cell lines called HeLa-CF, HL-CF, H-292-CF, HuEVEC-CF, McCoy-CF, African green monkey and other cell lines that are capable of supporting chlamydial growth. Various CF strains of mice, rabbits and other animal models for research use can be produced.

Because Chlamydia is highly infectious, organisms which have been cleared of extracellular, replicating and cryptic infections must be protected from exposure to viable EBs if the organisms are to remain clear. The inventors have discovered that many of the nutrients and other materials used to maintain continuous cell lines are contaminated with viable Chlamydia EBs. For example, every lot of fetal calf serum has tested positive for the Chlamydia MOMP gene by PCR. Since extensive digestion is required for isolation of the DNA, we have concluded it is bound in EBs. *C. pneumoniae* can also be cultured directly from fetal calf serum. Thus, it is necessary to inactivate EBs in these materials, such as culture media and nutrients, used to maintain the Chlamydia-free status of the organism. Collectively these materials are referred to herein as "maintenance materials"). In one embodiment, nutrients and culture media are subjected to gamma irradiation to inactivate Chlamydia therein. Preferably, the material should be irradiated for a period of time sufficient to expose the material to at least 10,000 rads of gamma radiation. It is important for the material to be contained in vessels that do not absorb high energy radiation. The preferred vessel is plastic. In another embodiment, the maintenance materials are treated with a disulfide reducing agent (e.g.,dithiothreitol (10 $\mu$M) for about 30 minutes) and then the treated maintenance materials are passed through a standard submicron (e.g., about 0.45 microns) filtration system. The reducing agent causes any EBs to expand to the size where a 0.45 micron filter will block their passage. Examples of suitable disulfide reducing agents include, but are not limited to, dithiothreitol, succimer, glutathione, DL-penicillamine, D-penicillamine disulfide, 2,2'-dimercaptoadipic acid, 2,3-dimercapto-1-propone-sulfide acid. In yet another embodiment, maintenance materials are treated with a disulfide reducing agent, preferably dithiothreitol (e.g., about 10 $\mu$M concentration), before the materials are passed through a filtration system to remove Chlamydia therefrom.

In order to insure that research tools, such as cell lines and animals, remain Chlamydia-free, an assay has been designed to evaluate whether an organism is Chlamydia-free. The method comprises obtaining a sample of cells or tissue culture; optionally culturing the cells in the presence or absence of cycloheximide; and determining the presence or absence of Chlamydia nucleic acid by a suitable amplification technique, such as PCR. The absence of nucleic acid amplification signal is indicative that the status of the organism is Chiamydia-free.

Susceptability Testing for Evaluating Active Agents Against Various Forms of Chlamydia This invention pertains to novel approaches for the susceptibility testing of Chlamydia species that are necessitated by the complex life cycle of the chlamydial pathogen as well as by its diverse, extensive, and heretofore unappreciated ability to cause chronic, cryptic and persistent systemic infections that are refractory to short duration therapy with conventional single agents. The inventors have discovered that successful management or eradication of chronic/systemic chlamydial infections can be predicted by using the described unique methods for in vitro and in vivo susceptibility testing.

The invention is based upon the discovery that current susceptibility testing methods for Chlamydiae do not accurately predict the ability of antimicrobial agents to successfully and totally eradicate chronic chlamydial infections. This is because the current susceptibility testing methods measure only replication of chlamydia and ignores the well-known "cryptic phase" in which intracellular Chlamydiae are not actively replicating. Moreover, it has also been discovered that the so-called "cryptic phase" of Chlamydiae includes multiple and different sub-phases. The following are some of the phases of the chlamydial life cycle in which the intracellular Chlamydiae are not replicating: an initial intranuclear phase in which elementary bodies (EBs) transition to reticulate bodies (RBs), an intracytoplasmic phase in which there is a transition of the RB phenotype to the EB phenotype, an intracytoplasmic phase with a nonreplicating, but metabolizing RB, and intracellular/extracellular EB phases, including endocytotic and exocytotic phases, in which there is neither replication nor metabolism. In order to assess the cumulative and long term effect of antimicrobial therapy on these multiple life phases, unique in vitro and in vivo susceptibility test methods have been developed and are described herein.

The term "susceptibility" as used herein is intended to mean a physiological response of an organism to an environmental or chemical stimuli. The desired physiological response to stimuli is one which adversely affects the pathogen's viability to replicate or reside within the host cell and, ideally, would result in the reduction or complete elimination (i.e., death) of that pathogen.

A. In Vitro Methodology

One aspect of the invention pertains to methods for evaluating the susceptibility of the distinct phases and stages of the life cycle of Chlamydia, particularly the cryptic phase to a particular agent(s), since prior techniques have failed, heretofore, to appreciate the need for drugs that can clear infected cells of cryptic Chlamydia. A preferred drug screening method which accomplished this objective utilizes tissue culture cells which are maintained, in the absence of cycloheximide in order to encourage cryptic infection. Cryptic infection is uncommon in cells used in standard cell culture susceptibility techniques because Chlamydia in cycloheximide-paralyzed cells need not compete with the host cell for metabolites and hence are encouraged to replicate.

The in vitro method uses standard tissue culture cells, but without the addition of cycloheximide. Moreover, the chlamydiae are allowed to replicate for several days prior to the addition of one or more test agents. A "test agent" can be any compound or combination of compounds to be evaluated as an antichlamydial agent for its ability to significantly reduce the presence of Chlamydia in living cells. For example, a test agent can include, but is not limited to, antibiotics, antimicrobial agents, antiparasitic agents, antimalarial agent, disulfide reducing agents and antimycobacterial agents. Antimicrobial agent(s) (test agent) is then added to the replicating cells. The antimicrobial agents/ growth medium are periodically replaced for the duration of the incubation time, which is preferably weeks rather than days. The test agent(s) is/are replaced when needed for the duration of the incubation time (days to weeks) to ensure that the test agent is present and has not been otherwise degraded. Finally, the end point after the prolonged incubation time is the complete absence of chlamydial DNA, as determined by a nucleic acid amplification technique, such as the polymerase chain reaction (PCR) methodology. Standard nucleic acid amplification techniques (such as PCR) are used to ascertain the presence or absence of signal for chlamydial DNA encoding MOMP or another unique Chlamydia gene to determine whether the test agent or combination of agents is/are effective in reducing Chlamydia infection. The loss of signal (i.e., below the detectable level of the nucleic acid amplification technique) in cells with antibiotic(s) versus its presence in controls is an indication of efficacy of the agent or combination of agents against Chlamydia.

Accordingly, the susceptibility test of this invention can be used to identify an agent or agents which are targeted against any particular species of Chlamydia and can be used to identify agent(s) targeted against the cryptic form of the pathogen, i.e., is capable of inhibiting or eliminating the cryptic form of the pathogen. In one embodiment, this is done by performing the susceptibility test while placing the cells under stringent environmental conditions known to induce Chlamydia to enter a cryptic phase. Agents that are effective against Chlamydia, as ascertained by the susceptibility testing protocols described herein, can be used as part of a therapy for the management of Chlamydia infections. Suitable therapeutic protocols are described in detail below, with a particular focus on targeting agents toward specific stages of the chlamydial life cycle.

The methods described herein are unique because they evaluate the activity of antimicrobial agents in the absence of cycloheximide which provides a more clinically relevant intracellular milieu. For example, any normally operating, energy-dependent host cell membrane pumps which might move antimicrobial agents in or out of the cell are inactivated by the use of cycloheximide. The methods described herein are unique because they utilize culture medium which has previously been inactivated. The methods are also unique because they measure the effect of a prolonged duration of exposure to the antimicrobial agent(s) after the intracellular infection by chlamydiae has become established. Finally, the method is unique because it measures the presence/absence of chlamydial DNA as the endpoint, for example by measuring PCR signal. By using complete eradication of chlamydial DNA as an endpoint, the susceptibility test confirms that all phases of Chlamydiae have been eradicated as opposed to there having been merely a temporary halt in replication.

When a nucleic acid amplification methodology, such as PCR, is used to evaluate assay endpoint, the nucleic acid assay (e.g., PCR) method can be enhanced by the unique application of a reducing agent, such as dithiothreitol (DTT), in order to perturb the coat of chlamydial EBs and hence allow exposure of the DNA by the action of a protein digestive compound, such as proteinase K. In other words, the reducing agent permits the EB coating to rupture. By using an assay for DNA in which EBs are specifically uncoated, the susceptibility test endpoint assesses the presence or absence of EBs as well as the presence or absence of both replicating and nonreplicating RBs. Thus, this approach for chlamydial susceptibility testing allows quantitative antimicrobial susceptibility assays of single and combination agents in which the cumulative effect of the agent(s) on the complete eradication of all life phases is measured. Examples of results obtained with this in vitro method are described below.

In one embodiment, a suitable nucleic acid assay for identifying agents effective against the cryptic form of Chlamydia comprises, in the presence of agent(s) to be tested, subjecting cultured cells to reducing agent (e.g., dithiothreitol) and protease digestion or guanidine isothiocyanate (also known as guanidine thiocyanate) for a prescribed period of time; extracting DNA from the treated solution; exposing DNA to appropriate polymerase, dNTPs and primers for DNA amplification of MOMP or other protein of the Chlamydia species; and determining the presence or absence of amplified DNA by visualizing the ethidium bromide treated DNA product by gel electrophoresis, for example, or alternatively by Southern Blot. In particular embodiments, the Chlamydia species is C. pneumoniae and the appropriate primers are CHLMOMPDB2 and CHLMOMPCB2.

The invention further relates to a method of identifying cells containing a non-EB cryptic form of a Chlamydia species by a nucleic acid amplification technique (e.g., PCR) comprising subjecting cultured cells to protease digestion; stopping protease activity; exposing cells to appropriate heat-stable DNA polymerase, dNTPs and labeled primers (e.g., 3'-biotin labeled, 5'-biotin labeled) for amplification of DNA encoding MOMP of the Chlamydia species; washing the cells; exposing the cells to a reporter molecule (e.g., strepavidin-conjugated signal enzyme); exposing the cells to an appropriate substrate for the reporter molecule (e.g., conjugated enzyme); and visualizing the amplified DNA encoding MOMP by visualizing the product of the reaction.

The invention pertains to a method of identifying cells containing a cryptic form of Chlamydia. The method comprises treating cultured cells, thought to be infected with Chlamydia, with a disulfide reducing agent; subjecting cultured cells to protease digestion; exposing cells to appropriate polymerase, dNTPs and primers for DNA amplification of nucleic acid encoding of a chlamydial protein; exposing the cells to a reporter molecule enzyme; exposing the cells to an appropriate substrate for the reporter enzyme; and determining the presence of a cryptic form of Chlamydia by visualizing the amplified DNA encoding a chlamydial protein. Preferably, the amplification technique is PCR and the primers are CHLMOMPDB2 and CHLMOMPCB2 of *Chlamydia pneumoniae*.

A similar method can be used as an assay for identifying an agent which is effective against a cryptic form of Chlamydia. Accordingly, the method comprises treating cultured cells grown in the absence of cycloheximide, thought to be infected with Chlamydia, with a disulfide reducing agent; allowing the Chlamydia to replicate; adding a test agent; subjecting cultured cells to protease digestion; exposing cells to appropriate polymerase, dNTPs and primers for DNA amplification of a gene encoding chlamydial protein; exposing the cells to a reporter molecule enzyme; exposing the cells to an appropriate substrate for the reporter enzyme; and determining the presence of cryptic form of Chlamydia by visualizing the amplified DNA encoding a chlamydial protein, such as MOMP.

B. In Vivo Methodology

In another aspect of the invention. the susceptibility test can be used to evaluate the status of a human or animal undergoing therapy for the management of Chlamydia infection. For example, a biological material is isolated from the human or animal to undergo combination therapy. The biological material is treated such that the Chlamydia is isolated therefrom. This chlamydial isolate is allowed to infect Chlamydia free cells. These infected cells are then exposed to the combination of agents being used in the individual undergoing combination therapy. Alternatively, the individual's serum containing the antimicrobial agents can be added to the infected cells as a "serum bactericidal test" for intracellular chlamydial infection. The presence of chlamydial DNA is then measured.

The in vivo method uses the murine model although other animals such as rats or rabbits can be used. In this method, mice (or any other animal) are inoculated intranasally with $2 \times 10^5$ chlamydial EBs per ml. The inventors have confirmed the work of Yang and colleagues (*J. Infect. Dis.*, 171:736–738 (1995)) in which intranasal inoculation of chlamydial EBs results in systemic dissemination and, in particular, causes infection of the spleen. The inventors have discovered that this systemic dissemination also results in the presence of EBs in the blood of the mice. Therefore, infectivity can be measured by blood culture or by serum/whole blood PCR for chlamydial DNA. Systemic infection is also confirmed and monitored by the presence of elevated IgM and IgG antibody titers. After the systemic murine infection has been established, antimicrobial agents are given to the mice. This is most easily done by adding the antibiotics to the drinking water. The effect of antichlamydial therapy is monitored by serum/whole blood PCR. When the serum/PCR assay suggests eradication of chlamydiae from the bloodstream, the mice are sacrificed and PCR for chlamydial DNA is done on lung, heart, liver, and spleen homogenates. This method is unique because it measures the complete eradication of all life forms of chlamydiae in known murine target organs for chlamydial infection. This in vivo susceptibility method has revealed, for example, that antimicrobial therapy with the triple agents, INH, metronidazole and penicillamine, can completely eradicate *C. pneumoniae* from infected mice in four months. Moreover, following complete eradication of chlamydiae, multiple attempts to reinfect these cured mice via intranasal inoculation have proven unsuccessful. This suggests that effective management and complete eradiaction results in the development of protective immunity, and that effective management is therefore a way to create effective immunity.

Performing PCR for chlamydial DNA on homogenates of other organ systems can be used to determine the effectiveness of particular antibiotic combinations in eradicating chlamydial infection in those organ systems. Establishment of prior chiamydial infection of those systems can be done by either biopsy or antibody-enhanced radiological imaging. Alternatively, prior infection can be determined statistically by performing PCR for chlamydial DNA on homogenates of the same organ systems in a similarly inoculated but untreated control population. Organ-specific susceptibility is determined by comparing rates of positive PCR assays in the control and treated populations.

An alternative or complementary method of determining the presence of cryptic chlamydial infections in an animal or cell culture is to expose the culture to chlamydia-stimulating compounds. Such compounds include (but are not limited to) cycloheximide, corticosteriods (such as prednisone) and other compounds which are known to stimulate reactivation of cryptic intracellular infections, and disulfide reducing agents (such as dithiotreitol) and other chemicals which cause EBs to turn into RBs. Once the cryptic forms have entered a more active phase, they can be detected using standard detection techniques such as visual detection of inclusion bodies, immunochemical detection of chlamydial antigen, or reverse transcriptase-PCR.

Antichlamydial Therapy Directed Toward the Initial Stage of Chlamydia Infection

A number of effective agents that are specifically directed toward the initial phase of chlamydial infection (i.e., transition of the chlamydial EB to an RB) have been identified. This "cryptic" growth phase, unlike that of the replicating chlamydial microorganism, which uses host cell energy, involves electrons and electron transfer proteins, as well as nitroreductases. Based upon this, it has been discovered that the initial phase of Chlamydia infection is susceptible to the antimicrobial effects of nitroimidazoles, nitrofurans and other agents directed against anaerobic metabolism in bacteria.

Nitroimidazoles and nitrofurans are synthetic antimicrobial agents that are grouped together because both are nitro ($NO_2$—) containing ringed structures and have similar antimicrobial effects. These effects require degradation of the agent within the microbial cell such that electrophilic radicals are formed. These reactive electophilic intermediates then damage nucleophilic protein sites including ribosomes, DNA and RNA. Nitroimidazoles and nitrofurans currently are not considered to possess antimicrobial activity against members of the Chlamydia species. This lack of antimicrobial activity, however, is due to the fact that conventional susceptibility testing methods only test for effect on the replicating form of Chlamydia species.

Examples of suitable nitroimidazoles include, but are not limited to, metronidazole, tinidazole, bamnidazole, benznidazole, flunidazole, ipronidazole, misonidazole, moxnidazole, ronidazole, sulnidazole, and their metabolites, analogs and derivatives thereof. Metronidazole is most preferred. Examples of nitrofurans that can be used include, but are not limited to, nitrofurantoin, nitrofurazone, nifuirtimox, nifuratel, nifuradene, nifurdazil, nifurpirinol, nifuratrone, furazolidone, and their metabolites, analogs and derivatives thereof. Nitrofurantoin is preferred within the class of nitrofurans.

Throughout this application and for purposes of this invention, "metabolites") are intended to embrace products of cellular metabolism of a drug in the host (e.g., human or animal) including, but not limited to, the activated forms of prodrugs. The terms "analogs" and "derivatives" are intended to embrace isomers, optically active compounds and any chemical or physical modification of an agent, such that the modification results in an agent having similar or increased, but not significantly decreased, effectiveness against Chlamydia, compared to the effectiveness of the parent agent from which the analog or derivative is obtained. This comparison can be ascertained using the susceptability tests described herein.

Cells to be treated can already be cryptically infected or they can be subjected to stringent metabolic or environmental conditions which cause or induce the replicating phase to enter the cryptic phase. Such stringent conditions can include changing environmental/culturing conditions in the instance where the infected cells are exposed to γ-interferon; or by exposing cells to conventional antimicrobial agents (such as macrolides and tetracyclines) which induce this cryptic phase of chlamydial infection in human host cells.

Novel Antichlamydial Therapy Directed Toward the Replicating and Cryptic Stationary Phases of Chlamydia Infection A unique class of antichlarnydial agents that is effective against the replicating and cryptic stationary phases of Chlamydia (and possibly against some other stages of the cryptic phase) have been identified using the susceptibility tests described herein. This novel class of agents comprises ethambutol and isonicotinic acid congeners which include isoniazid (INH), isonicotinic acid (also known as niacin), nicotinic acid, pyrazinamide, ethionamide, and aconiazide; where INH is most preferred. Although these are currently considered effective only for mycobacterial infections, due in part to currently available susceptability testing methodologies, it has been discovered that these agents, in combination with other antibiotics, are particularly effective against Chlamydia. It is believed that the isonicotinic acid congeners target the constitutive production of catalase and peroxidase, which is a characteristic of microorganisms, such as mycobacteria, that infect monocytes and macrophages. Chlamydia can also successfully infect monocytes and macrophages.

Using INH to eradicate Chlamydia from macrophages and monocytes subsequently assists these cells in their role of fighting infection. However, these agents appear to be less effective, in vitro, against the cryptic phase. Thus, ethambutol, INH and other isonicotinic acid congeners ideally should be used in combination with agents that target other phases of the chlamydial life cycle. These isonicotinic acid congeners are nevertheless excellent agents for the long term therapy of chronic/systemic chlamydial infection generally, and in particular to chiamydial infection of endothelial and smooth muscle cells in human blood vessels.

INH and its congeners can be used to clear infection from monocytes and/or macrophages. When monocytes and macrophages are infected by Chlamydia, they become debilitated and cannot properly or effectively fight infection. It is believed that, if the chlamydial infection, per se, is cleared from these cells, then the monocytes and macrophages can resume their critical roles fighting chlamydial or other infection(s). Thus, patient responsiveness to combination therapy can be optimized by the inclusion of isonicotinic acid congeners. Accordingly, one aspect of the invention provides a specific method for reempowering monocytes or macrophages that have been compromised by a Chlamydia infection and, in turn, comprise treating the infection in other sites. Such compromised macrophages or monocytes can be activated by treating the chlamydial infection by contacting the infected macrophages and/or monocytes with an antichlamydial agent.

Therapy Directed Toward Elementary Bodies of Chlamydia

As discussed above, it has been discovered that adverse conditions, such as limited nutrients, antimicrobial agents, and the host immune response, produce a stringent response in Chlamydia. Such adverse conditions are known to induce stringent responses in other microorganisms (C. W. Stratton, In: *Antibiotics in Laboratory Medicine*, Fourth Edition. Lorian V (ed) Williams & Wilkins, Baltimore, pp 579–603 (1996)) and not surprisingly induce a stringent response in Chlamydia. This stringent response in Chlamydia alters the morphological state of the intracellular microorganism and creates dormant forms, including the intracellular EB, which then can cryptically persist until its developmental cycle is reactivated. Conversely, the host cell may lyse and allow the EBs to reach the extracellular milieu. Thus, it is necessary to utilize a combination of agents directed toward the various life stages of Chlamydia and, in particular, against the elementary body for successful management of infection.

During the unique chlamydial life cycle, it is known that metabolically-inactive spore-like EBs are released into the extracellular milieu. Although these released EBs are infectious, they may not immediately infect nearby susceptible host cells until appropriate conditions for EB infectivity are present. The result of this delay in infection is the extracellular accumulation of metabolically-inactive, yet infectious, EBs. This produces a second type of chlamydial persistance referred to herein as EB "tissue/blood load"). This term is similar in concept to HIV load and is defined herein as the number of infectious EBs that reside in the extracellular milieu. Direct microscopic visualization techniques, tissue cell cultures, and polymerase chain reaction test methods have demonstrated that infectious EBs are frequently found in the blood of apparently healthy humans and animals. This phenomenon is clearly of great clinical importance in chlamydial infections as these metabolically-inactive EBs escape the action of current antichlamydial therapy which is directed only against the replicating intracellular forms of Chlamydia. The presence of infectious extracellular EBs after the completion of short term. anti-replicating phase therapy for chlamydial infections has been shown to result in intracellular infection relapse. Thus, the duration and nature of antichlamydial therapy required for management of chlamydial infections is, in part, dictated by the extracellular load of EBs. For purposes of this invention, short term therapy can be approximately two to three weeks; long term therapy in contrast is for multiple months.

As described in previous sections. it is also believed that persistance of chlamydial infections, in part, may be due to the presence of cryptic forms of Chlamydia within the cells. This cryptic intracellular chlamydial form apparently can be activated by certain host factors such as cortisone (Yang et al., Infection and Immunity, 39:655–658 (1983); and Malinverni et al., *The Journal of Infectious Diseases*, 172:593–594 (1995)). Antichlamydial therapy for chronic Chlamydia infections must be continued until any intracellular EBs or other intracellular cryptic forms have been activated and extracellular EBs have infected host cells. This reactivation/reinfection by chlamydial EBs clearly is undesirable as it prolongs the therapy of chlamydial infections, as well as increases the opportunity for antimicrobial resistance to occur.

Physiochemical agents have been identified that can inactivate chlamydial EBs in their respective hosts by reducing disulfide bonds which maintain the integrity of the outer membrane proteins of the EBs. For Chlamydia, disruption of the outer membrane proteins of EBs thereby initiates the transition of the EB form to the RB form. When this occurs in the acellular milieu where there is no available energy source, the nascent RB perishes or falls victim to the immune system. Thus, disulfide reducing agents that can interfere with this process are suitable as compounds for eliminating EBs.

One such class of disulfide reducing agents are thiol-disulfide exchange agents. Examples of these include, but are not limited to, 2,3-dimercaptosuccinic acid (DMSA; also referred to herein as "succimer"); D,L,-β,β-dimethylcysteine (also known as penicillamine); β-lactam agents (e.g., penicillins, penicillin G, ampicillin and amoxicillin, which produce penicillamine as a degradation product), cycloserine, dithiotreitol, mercaptoethylamine (e.g., mesna, cysteiamine, dimercaptol), N-acetylcysteine, tiopronin, and glutathione. A particularly effective extracellular antichlamydial agent within this class is DMSA which is a chelating agent having four ionizable hydrogens and two highly charged carboxyl groups which prevent its relative passage through human cell membranes. DMSA thus remains in the extracellular fluid where it can readily encounter extracellular EBs. The two thiol (sulfhydryl) groups on the succimer molecule (DMSA) are able to reduce disulfide bonds in the MOMP of EBs located in the extracellular milieu.

Penicillamine can also be used as a disulfide reducing agent to eliminate chlamydial EBs. However, the use of penicillamine may cause undesirable side effects. Thus, as an alternative, those β-lactam agents which are metabolized or otherwise converted to penicillamine-like agents in vivo (i.e., these agents possess a reducing group) can be orally administered to the human or animal as a means of providing a controlled release of derivative penicillamine, by non-enzymatic acid hydrolysis of the penicillin, under physiologic conditions. Clavulonic acid is not required for this hydrolysis or for using β-lactam agents to create penicillamine in vivo.

Currently Recognized Agents Active Against Chlamydia Replication

As chlamydial RBs transform into EBs, they begin to utilize active transcription of chlamydial DNA and translation of the resulting mRNA. As such, these forms of Chlamydia are susceptible to currently used antimicrobial agents. The antichlamydial effectiveness of these agents can be significantly improved by using them in combination with other agents directed at different stages of Chlamydia life cycle, as discussed herein.

Classes of suitable antimicrobial agents include, but are not limited to, rifamycins (also known as ansamacrolides), quinolones, fluoroquinolones, chloramphenicol, sulfonamides/sulfides, azalides, cycloserine, macrolides and tetracyclines. Examples of these agents which arc members of these classes, as well as those which are preferred, are illustrated below in Table 5.

TABLE 5

| Drug Class | Agents Effective Against the Replicating Phase of Chlamydia<br>Examples | Preferred |
|---|---|---|
| Quinolones/<br>Fluoroquinolones | Ofloxacin<br>Levofloxacin<br>Trovafloxacin<br>Sparfloxacin<br>Norfloxacin<br>Lomefloxacin<br>Cinoxacin<br>Enoxacin<br>Nalidixic Acid<br>Fleroxacin<br>Ciprofloxacin | Levofloxacin |
| Sulfonamides | Sulfamethoxazole | Sulfamethoxazole/<br>Trimethoprim |
| Azalides | Azithromycin | Azithromycin |
| Macrolides | Erythromycin<br>Clarithromycin | Clarithromycin |
| Lincosamides | Lincomycin<br>Clindamycin | |
| Tetracyclines | Tetracycline<br>Doxycycline<br>Minocycline<br>Methacycline<br>Oxytetracyline | Minocycline |
| Rifamycins<br>(Ansamacrolides) | Rifampin<br>Rifabutin | Rifampin |

All members of the Chlamydia species, including *C. pneumoniae*, are considered to be inhibited, and some killed, by the use of a single agent selected from currently used antimicrobial agents such as those described above. However, using the new susceptability test, the inventors have found complete eradication of Chlamydia cannot be achieved by the use of any one of these agents alone because none are efficacious against all phases of the Chlamydia life cycle and appear to induce a stringent response in Chlamydia causing the replicating phase to transform into cryptic forms. This results in a persistent infection in vivo or in vitro that can be demonstrated by PCR techniques which assess the presence or absence of chlamydial DNA. Nevertheless, one or more of these currently used agents, or a new agent directed against the replicating phase of Chlamydia, should be included as one of the chlamydial agents in a combination therapy in order to slow or halt the transition of the EB to the RB as well as to inhibit chlamydial replication.

Methodology for Selecting Potential Agent Combinations

In attempting to manage or eradicate a systemic infection, it is critical to target multiple phases in the life cycle of Chlamydia, otherwise viable Chlamydia in the untargeted phases will remain after therapy and result in continued, chronic infection. This fundamental insight is at the core of this invention.

A preferred method for selecting an appropriate combination of agents that satisfies the requirements of this strategy comprises a plurality of steps as follows:

1. Identify the phases of the chlamydial life cycle. For example, the following phases are currently known:
   - a. Elementary Body ("EB")—Extracellular or Intracellular. Intracellular EBs may represent a type of "cryptic phase".
   - b. EB to Reticulate Body ("RB") transition phase.
   - c. Stationary RB phase. This is what is traditionally thought of as the "cryptic phase".
   - d. Replicating RB phase.
   - e. RB to EB transition phase (also called "condensation").

2. Evaluate the relative importance of targeting each particular phase in eradicating reservoirs of Chlamydia from the host organism. For example, the life-cycle stages listed in step 1 can be prioritized based on the following assumptions:

a. In the host, Extracellular and intracellular EBs represent a very important reservoir of infectious agents that result in chronic and and persistent infection.

b. Most intracellular RBs in chronic infections are non-replicating. The 3–4 day reproduction cycle seen in cycloheximide-treated eukaryotic cells is an artifact of an atypical, cell culture environment designed primarily to propagate Chlamydia.

c. The transition phases represent only a small portion of Chlamydia in chronic infections.

3. Identify "targets" for each phase of the selected life cycle phases. A target is an attribute of Chlamydia which is vulnerable during a particular life cycle phase. For example, the disulfide bonds in MOMP are a target during the EB phase.

4. Identify agents with known or theoretical mechanism (s) of action against those targets.

5. Estimate whether those agents would be merely inhibitory or, preferably, cidal, through an understanding of their mechanism of action.

6. Confirm the estimate by using the following approaches:

a. In the case of anti-EB agents, treat EBs with the agent, then attempt to infect cells with the treated EBs. If the cells do not become infected, the agent is EB-cidal.

b. In the case of other agents, use the susceptibility tests disclosed elsewhere herein, to determine whether the agent, either alone or in combination with other agents, is chlamydicidal.

7. Select a combination of agents that, through their individual effects, provide activity against targets for the most important phases within the chlamydial life cycle. Preferably, a combination should target as many phases of the life cycle as possible, seeking to maximize the total of the relative important scores of the phases targeted while minimizing the number of drugs involved.

8. Test the combination using the susceptibility testing procedures described elsewhere. This step is necessary because the selected combination may or may not be chlamydicidal for various reasons such as intracellular penetration and/or efflux.

9. Set initial dosages based on clinical standards which consider the pharmacokenetics and pharmacodynamics for the drugs prescribed individually; modifications, if needed, are based on results of susceptibility testing and in vivo efficacy.

Table 6 provides an example of how the foregoing methodology can be used. The preferred embodiment includes agents which:

a) Target disulfide bonds in the EB and condensation phases;

b) Target non-oxidative metabolism in the stationary/cryptic phase;

c) Target constitutive production of peroxidases and catalyses in the stationary and replicative phases;

d) In the latter two cases, work through physio-chemical disruption of the organism through free radicals, which are very difficult for organism to develop resistance to; and e) Optionally adds an agent to target DNA-dependent RNA polymerase in the EB→RB phase.

The foregoing methodology for selecting combination therapies can be automated (e.g., by a computer system) at one or a combination of the steps described above. This methodology is applicable even after greater understanding of the chlamydial life cycle leads to a re-prioritization or even sub-division of the life-cycle phases, new theoretical targets within Chlarnydia are identified, or new drugs are developed which attack currently known or new targets within Chlamydia. For example, the phases of the life cycle could be further sub-classified based on the type of host cell the phase is in. Thus, stationary phase RBs in macrophages could be considered a separate phase than stationary phase RBs in hepatocytes. This allows the methodology to be used to design a single or multi-tissue specific combination of agents.

TABLE 6

Example of using Theoretical Effect on Various Targets within the Chlamydialc Life Cycle to Pick a Combination Therapy

| Potentially vulnerable attributes of Chlamydia: | Disulfide bonds | Non-oxidative metabolism | Constituitive production of peroxidases and catalyses | Topoisomerases | DNA-dependent RNA polymerase | Folic acid pathway | Ribosomes involved in protein synthesis | . . . |
|---|---|---|---|---|---|---|---|---|
| Phase in Chlamydial Life Cycle | Theoretical Targets | | | | | | | Relative Importance |
| EB (Extracellular or Intracellular) | X | | | | | | | 8 |
| EB->RB Transition | | p | | p | X | | | 6 |
| Stationary Phase RB ("Cryptic phase") | | X | X | p | p | p | p | 8 |
| Replicating RB | | p | X | X | p | X | X | 7 |
| RB->EB Transition ("Condensation") | X | p | | p | | | | 6 |
| Pharmaceutical Compounds | | | | | | | | |
| Non-Novel Classes | | | | Quinolones, Fluroquinolones | Rifamycins | Sulfonamides | Azalides, Macrolides, Lincosamides, Tetracyclines | |

TABLE 6-continued Example of using Theoretical Effect on Various Targets within the Chlamydiale Life Cycle to Pick a Combination Therapy

| Potentially vulnerable attributes of Chlamydia: | Disulfide bonds | Non-oxidative metabolism | Constituitive production of peroxidases and catalyses | Topoisomerases | DNA-dependent RNA polymerase | Folic acid pathway | Ribosomes involved in protein synthesis | ... |
|---|---|---|---|---|---|---|---|---|
| Novel Classes | Disulfide reducing agents | Agents that strip electrons from carrier proteins and become free-radicals | Agents activated by peroxidases and catalyses to become free-radicals | | | | | |
| Examples: | Thiol-disulfide reducing agents | Nitroimidazoles & Nitrofurans | Isonicotinic acid cogeners | | | | | |
| Drugs of Choice (based on effectiveness) | Penicillamine (from Amoxicillan) | Metronidazole or Nitrofurantoin | INH | Levofloxacin Trovafloxavin | Rifampin | Sulfa-methoxizole/ trimethoprim | Azythromycin Clarithromycin Minocycline | |
| Preferred Embodiment | Penicillamine (Amoxicillan) | Metronidazole | INH | | ±Rifampin | | | |

X = known target relevant to that life phase;
p = possible target relevant to that life phase

Diseases Associated with Chlamydial Infection

An association has been discovered between chronic Chlamydia infection of body fluids and/or tissues with several disease syndromes of previously unknown etiology in humans which respond to unique antichlamydial regimens described herein. To date, these diseases include Multiple Sclerosis (MS), Rheumatoid Arthritis (RA), Inflammatory Bowel Disease (IBD), Interstitial Cystitis (IC), Fibromyalgia (FM), Autonomic nervous dysfunction (AND, neural-mediated hypotension); Pyoderma Gangrenosum (PG), Chronic Fatigue (CF) and Chronic Fatigue Syndrome (CFS). Other diseases are under investigation. Correlation between Chlamydia infection and these diseases has only recently been established as a result of the diagnostic methodologies and combination therapies described herein.

Based on this evidence, published evidence of an association between atherosclerosis and Chlamydia (Grupta el al, *Circulation* 96:404–407 (1997)), and an understanding of the impact Chlamydia infections have on infected cells and the immune systems, the inventors have discovered a connection between Chlamydia and a broad set of inflammatory, autoimmune, and immune deficiency diseases. Thus, the invention describes methods for diagnosing and/or treating disease associated with Chlamydia infection, such as autoimmune diseases, inflammatory diseases and diseases that occur in immunocompromised individuals by diagnosing and/or treating the Chlamydia infection in an individual in need thereof, using any of the assays or therapies described herein. Progress of the treatment can be evaluated serologically, to determine the presence or absence of Chlamydia using for example the diagnostic methods provided herein. and this value can be compared to serological values taken earlier in the therapy. Physical improvement in the conditions and symptoms typically associated with the disease to be treated should also be evaluated. Based upon these evaluating factors, the physician can maintain or modify the antichlamydial therapy accordingly. For example, the physician may change an agent due to adverse side-effects caused by the agent, ineffectiveness of the agent, or for other reason. When antibody titers rise during treatment then alternate compounds should be substituted in order to achieve the lower antibody titers that demonstrate specific susceptability of the Chlamydia to the new regimen. A replacement or substitution of one agent with another agent that is effective against the same life stage of Chlamydia is desirable.

The therapies described herein can thus be used for the treatment of acute and chronic immune and autoimmune diseases when patients are demonstrated to have a Chlamydia load by the diagnostic procedures described herein which diseases include, but are not limited to, chronic hepatitis, systemic lupus erythematosus, arthritis, thyroidosis, scleroderma, diabetes mellitus, Graves' disease, Beschet's disease and graft versus host disease (graft rejection). The therapies of this invention can also be used to treat any disorders in which a chlamydial species is a factor or co-factor.

Thus, the present invention can be used to treat a range of disorders in addition to the above immune and autoimmune diseases when demonstrated to be associated with chlamydial infection by the diagnostic procedures described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated, as well as Wegners Granulomatosis.

Among the various inflammatory diseases, there are certain features of the inflammatory process that are generally agreed to be characteristic. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple sclerosis, peripheral neuropathy, chronic or recurrent sore throat, laryngitis, tracheobronchitis. chronic vascular headaches (including migraines, cluster headaches and tension headaches) and pneumonia when demonstrated to be pathogenically related to Chlamydia infection.

Treatable disorders when associated with Chlamydia infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo palsy; Cerebellar and Spinocerebellar Disorders, such as astructural lesions of the cerebellum; spinocerebellar degenerations (spinal ataxia, Friedreich's ataxia, cerebellar cortical degenerations. multiple systems degenerations (Mencel, Dejerine-Thomas, Shi-Drager, and Machado Joseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, or any subset thereof.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); carcinomas (such as colon carcinoma) and metastases thereof; cancer-related angiogenesis; infantile hemangiomas; alcohol-induced hepatitis. Ocular neovascularization, psoriasis, duodenal ulcers, angiogenesis of the female reproductive tract, can also be treated when demonstrated by the diagnostic procedures described herein to be associated with Chlamydial infection.

An immunocompromised individual is generally defined as a person who exhibits an attenuated or reduced ability to mount a normal cellular or humoral defense to challenge by infectious agents, e.g., viruses, bacterial, fungi and protozoa. Persons considered immunocompromised include malnourished patients, patients undergoing surgery and bone narrow transplants, patients underoing chemotherapy or radiotherapy, neutropenic patients, HIV-infected patients, trauma patients, burn patients, patients with chronic or resistant infections such as those resulting from myeloodysplastic syndrome, and the elderly, all of who may have weakened immune systems. A protein malnourished individual is generally defined as a person who has a serum albumin level of less than about 3.2 grams per deciliter (g/dl) and/or unintentional weight loss greater than 10% of usual body weight.

The course of therapy, serological results and clinical improvements from compassionate antichlamydial therapy in patients diagnosed with the diseases indicated were observed and are reported in Example 5. The data provides evidence to establish that treatment of Chlamydia infection results in the serological and physical improvement of a disease state in the patient undergoing combination therapy. These observations were consistent among a variety of different diseases which fall within a generalized disease class.

Figure 1B:
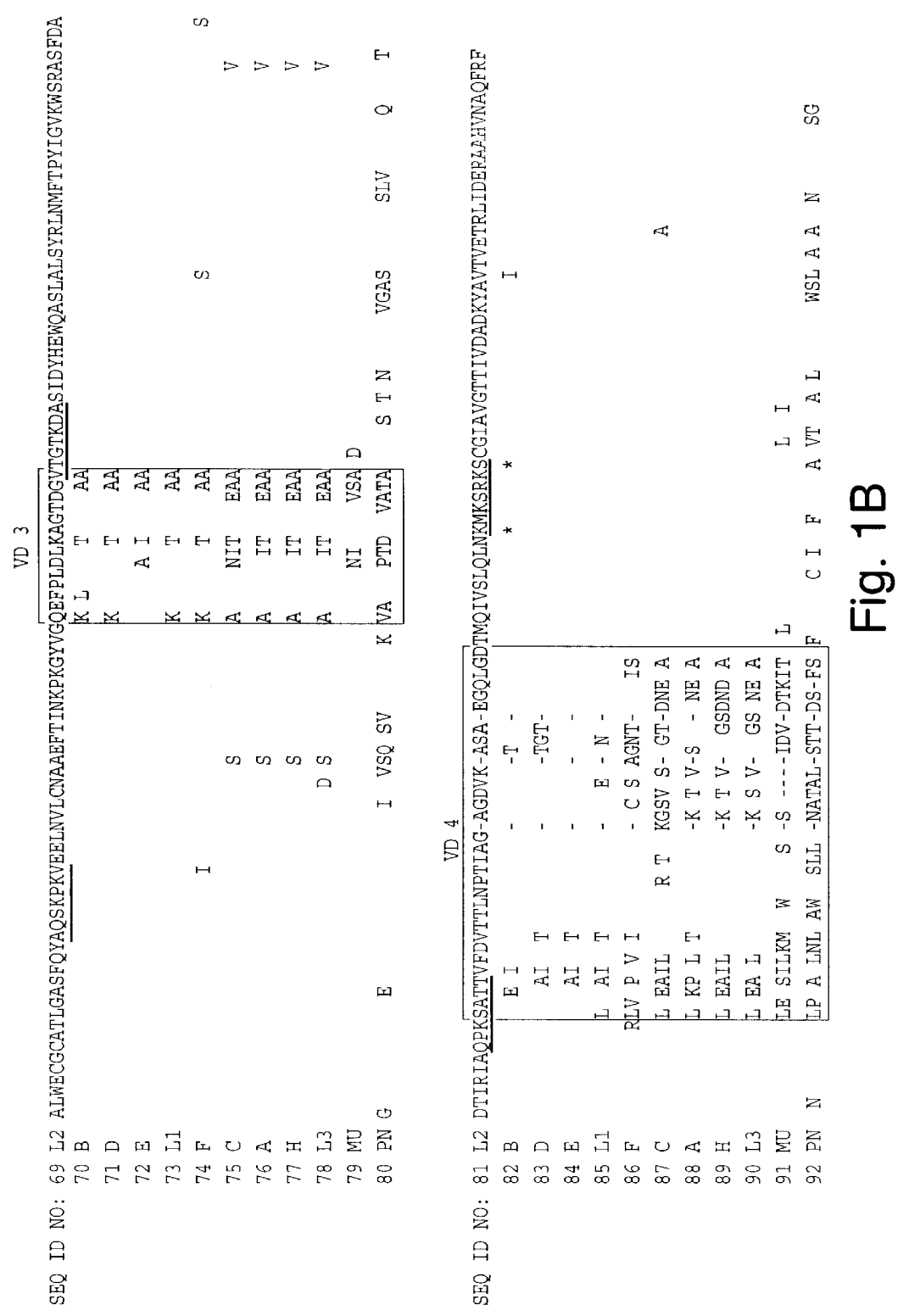

Other Diseases of Unknown Etiology with New Evidence for a Chlamydia Pneumoniae Etiology Both *C. trachomatis* and *C. psittaci* exhibit a protean disease complex dependent on different serovars. One known basis for this diversity to date is the amino acid sequence of the MOMP. FIG. 1 shows a sequence alignment of various Chlamydia MOMPs. Note that the size and sequence are relatively homologous except for the four variable regions that are responsible for the serovar (serotype) basis of classification. Further, it has been discovered that *C. pneumoniae* infects blood vessel endothelial cells from which EBs are released in the blood stream. In addition, macrophages are known targets for *C. pneumoniae* and may serve as reservoirs and provide an additional mechanism of transmission. *C. pneumoniae* is thus able to spread throughout the human body, establishing infection in multiple sites and in multiple organ systems. Infected sites may exist for an extended period without inducing symptoms that are noticed by the patient or by an examining physician. Sequence variability of MOMPs or other chlamydial antigens may provide a basis for organ specificity while other chlamydial proteins, such as the 60K and 70K heat shock proteins or LPS, may influence immune response.

*C. psittaci* and *C. pecorum* are known to cause a host of infections in economically significant animals. Thus, the teachings of this invention are relevant to animals. Throughout this application and for purposes of this invention, "patient" is intended to embrace both humans and animals. Virtually all rabbits and mice tested to date have PCR signals for *C. pneumoniae*. They can be used as appropriate animal models for treatment using specific combination antibiotics to improve therapy. (Banks et al., *Ameri. J. of Obstetrics and Gynecology* 138(7Pt2):952–956 (1980)); (Moazed et al., *Am. J. Pathol.* 148(2):667–676 (1996)); (Masson et al., *Antimicrob. Agents Chemother.* 39(9):1959–1964 (1995)); (Patton et al., *Antimicrob. Agents Chemother.* 37(1):8–13 (1993)); (Stephens et al., *Infect. Immun.* 35(2):680–684 (1982)); and (Fong et al., *J. Clin. Microbiol.* 35(1):48–52 (1997)).

Coupled with these developments are the recently developed rabbit models of coronary artery disease, where rabbits exposed to *C. pneumoniae* subsequently develop arterial plaques similar to humans (Fong et al., *J. Clin. Microbiol.* 35:48–52 (1997)). Most recently, a study at St. George's Hospital in London found that roughly ¾ of 213 heart attach victims have significant levels of antibodies to *C. pneumoniae* antibody and that those that have such antibodies achieve significantly lower rates of further adverse cardiac events when treated with antibiotics (Gupta et al., *Circulation* 95:404–407 (1997)). Taken together, these three pieces of evidence (the bacteria found in diseased tissue, inoculation with the bacteria causes diseases, and treating for the bacteria mitigates disease) make a case for a causal connection.

Adjunct Agents Used in Conjunction with the Combination Therapy

In addition to the combination therapies discussed above, other compounds can be co-administered to an individual undergoing antichiamydial therapy for the management of chronic/systemic infection. For example, it may be desirable to include one or a combination of anti-inflammatory agents and/or immunosuppressive agents to amelioriate side-effects that may arise in response to a particular antichlamydial agent, e.g., Herxheimer reactions. Initial loading with an anti-inflammatory steroid can be introduced to minimize side-effects of the antichlamydial therapy in those patients in which clinical judgment suggests the possibility of serious inflammatory sequelae.

Suitable anti-inflarnmatory agents (steroidal and nonsteroidal agents) include, but are not limited to, Prednisone, Cortisone. Hydrocortisone and Naproxin. Preferably the anti-inflammatory agent is a steroidal agent, such as Prednisone. The amount and frequency of administration of these adjunct compounds will depend upon patient health, age, clinical status and other factors readily apparent to the medical professional.

Vitamin C (2 gms bid) has also been introduced based on the report that Vitamin C (ascorbic acid) at moderate intracellular concentrations stimulates replication of *C. trachomatis* (Wang el al., *J. Clin. Micro.* 30:2551–2554 (1992)) as well as its potential effect on biofilm charge and infectivity of the bacterium and specifically the EB (Hancock, R. E. W., *Annual Review in Microbiology*, 38:237–264 (1984)).

Additionally, probenicid can optionally be added to the therapy as an enhancer. Probenecid is known to increase plasma levels of penicillins by blocking the uricosuric and renal tubular secretion of these drugs.

Diagnosis and Treatment of Secondary Porphyria

Chlamydia is a parasite of normal energy production in infected eukaryotic cells. As a result, host cells have insufficient energy available for their normal functioning. The energy shortage also causes the host cell mitochondria to attempt to synthesize certain critical enzymes involved in energy production in order to increase energy production. Because Chlamydia also prevents this synthesis from completing, these enzyme's precursors, called porphyrins, build up in cell and often escape into the intracellular mileau. Porphyrins readily form free-radicals. that, in turn, damage cells. Thus, there is an obligate secondary porphyria that accompanies many chiamydial infections. Therapy for this secondary porphyria, which is adjunct to antichlamydial therapy, involves at least three strategies: a) supplement the cellular energy supply to mitigate cell malfunction and the formation of porphyrins; b) reduce the levels of systemic porphyrins; and c) mitigate the harmful effects of the porphyrins.

The pathogenesis of chronic/systemic chlamydial infection is unique in that the intracellular infection by this parasite results in a number of heretofore unrecognized concomitant and obligatory metabolic/autoimmune disorders including secondary porphyria with associated autoantibodies against the porphyrins. Cross reaction with Vitamin B12 can result in a subclinical autoimmune-mediated Vitamin B12 deficiency. These associated disorders often require diagnosis and preventive and/or specific adjunctive therapy.

The first of these concomitant disorders is a porphyria which is a direct result of the chlamydial infection of host cells. This form of porphyria is a secondary porphyria as it is not the result of a genetic deficiency of the enzymes involved in the biosynthesis of heme. Based upon the discovery of this secondary form of porphyria, a unique approach for the diagnosis and treatment of obligatory and secondary disorders caused by Chlamydia infections has been developed. The adjunctive therapy described herein can be used in combination with the appropriate antimicrobial therapy required for eradication of the pathogen. This adjunctive therapy for secondary porphyria is particularly important for long-term antimicrobial therapy of chronic/systemic infections as such therapy often evokes symptoms of secondary porphyria.

The discussion below outlines the believed mechanism by which Chlamydiae induce these secondary metabolic disorders. The phrase "chlamydial-induced porphyria" is defined herein as an obligatory and secondary metabolic disorder which is the direct result of a chlamydial infection and which may find clincially relevant phenotypic expression requiring interventional therapy.

Chlamydiae are prokaryocytes that develop in eukaryotic cells and utilize part of the host cell metabolism (Becker, Y., *Microbiological Reviews*, 42:247–306 (1978); McClairty, G., *Microbiology*, 2:157–164(1994)). The transition of elementary bodies (EBs) to reticulate bodies (RBs) for Chlamydia species requires the presence of functioning mitochondria in the infected cell as well as the production by the host cell of nucleoside triphosphates which are needed for chlamydial biosynthesis of nucleic acids (Becker, Y., *Microbiological Reviews*, 42:247–306 (1978); McClairty, G., *Microbiology*, 2:157–164(1994); Ormsbee, R. A. and Weiss, E., *Science*, 2:1077 (1963); Weiss, E., *Jour. of Bacteriology*, 90:243–253 (1965); Weiss, E. and Kiesow, L. A., *Bacteriology Proceedings*, 85 (1966); Weiss, E. and Wilson, N. N., *Jour. of Bacteriology*, 97:719 (1969); Hatch et al., *Jour. of Bacteriology*, 150:662–670 (1985)). Chlamydiae are known to possess fragments of the glycolytic, pentose phosphate, and citric acid pathways and appear to be capable of converting glucose-6-phosphate (but not glucose) to pyruvate and pentose (Ormsbee, R. A. and Weiss, E., *Science*, 2:1077 (1963); Weiss, E. and Kiesow, L. A., *Bacteriology Proceedings*, 85 (1966)). However, Chlamydiae seem to lack enzymes needed for the net generation of adenosine triphosphate (ATP)(Weiss, E., *Jour. of Bacteriology*, 90:243–253 (1965)). Thus. chlamydial development is dependent on active mitochondrial and nuclear function of the host cell. For this reason, Chlamydiae are considered obligatory intracellular parasites (McClairty, G., *Microbiology*, 2:157–164(1994)). Chlamydial dependence on host cell energy must necessarily deplete the host cell's existing energy output at the net expense of depriving host cell biosynthetic pathways.

The requirement of an exogenous source of ATP and the presence of a specific ATP transport system in Chlamydiae have provided supporting evidence for the energy parasite concept (Hatch et al., *Jour. of Bacteriology*, 150:662–670 (1985)). This ATP transport system is an ATP-adenosine diphosphate (ADP) exchange mechanism (Peeling et al., *Infect. and Immun.*, 57:3334–3344 (1989)) similar to that found in mitochondria (Penefsky, H. S. and Cross, R. L., *Adv. Enzym. and Rel. Areas in Molec. Bio.*, 64:173–214 (1991)). Moreover, electron microscopic studies have shown that replicating Chlamydiae are always found in close proximity to mitochondria. Therefore, it has been suggested that Chlamydiae behave in the reverse manner of mitochondria in that mitochondria import ADP from the host cell cytoplasm and export ATP, while Chlamydiae import ATP and export ADP (Becker, Y., *Microbiological Reviews*, 42:247–306 (1978)).

The production of ATP within the mitochondria is powered by a mechanism called chemiosmotic coupling (Kalckar, H. M., *Annu. Review of Biochem.*, 60:1–37 (1991); Lehninger, A. L., *The Mitochondrion. Molecular Basis of Structure and Function*, The Benjamin Company, Incorporated, New York; Slater, E. C., *Europ. Journ. of Biochem.*, 166:489–504 (1987); Babcock, G. T. and Wickström, M., *Nature*, 356:301–309 (1992); Senior, A. E., *Physiology Review*, 68:177–231 (1988); Pedersen, P. I. and Carafoli, E., *Trends in Biochem. Sci.*, 12:145–150 (1987); Pedersen, P. I. and Carafoli, E., *Trends in Biochem. Sci.*, 12:145–150 (1987)). The citric acid cycle drives oxidation of NADH or FADH2, which, in turn, releases a hydride ion (H−), which is quickly converted to a proton (H+) and two high-energy electrons (2 e-). As the high-energy electron pair is transferred to each of these three multiprotein complexes, the protons produced pass freely from the mitochondria matrix to the intermembrane space via channels in complexes I, III and IV. Thus, the transfer of electrons from NADH down the electron transport chain causes protons to be pumped out of the mitochondrial matrix and into the intermembrane space. These protons then reenter the matrix through a specific channel in complex V. This proton gradient across the inner membrane results in the proton motive force which drives ATP synthesis.

Chlamydial ATPase in essence is competing for protons with host cell mitochondrial ATPase. This, of course, reduces the ATP produced by the mitochondria. A net reduction of ATP in the host cell mitochondria results in a concomitant lowering of the electron transfer in the host cell mitochondria because electron transfer and ATP synthesis are obligatorily coupled; neither reaction occurs without the other. The establishment of a large electrochemical proton gradient across the inner mitochondrial membrane halts normal electron transport and can even cause a reverse electron flow in some sections of the host cell respiratory chain. The reduction of electron transfer in the host cell mitochondria, in turn, lowers the translocation and reduction of extramatrix mitochondrial ferric iron to intramatrix ferrous iron. This energy depletion, in turn, interferes with the biosynthesis of heme.

A. Biosynthesis of Heme

Heme is a $Fe^{2+}$ complex in which the ferrous ion is held within the organic ligand, tetrapyrrolic macrocycle. The heme-containing tetrapyrrolic macrocyclic pigments are known as porphyrinogens and play a major role in cellular biochemistry. A number of critical cellular functions such as electron transport, reduction of oxygen, and hydroxylation are mediated by a family of heme-based cytochromes including catalase, peroxidase and superoxide dismutase. Moreover, the oxygen-carrying properties of hemoglobin and myoglobin are based on heme. Many cellular enzymes such as cytochrome P-450 and tryprophan pyrolase contain heme.

The biosynthesis of heme (Battersby et al., *Nature*, 285:17- (1980); Batterspy, A. R., *Proceedings of the Royal Society of London*, 225:1–26 (1985)) is an energy-dependent process which is adversely affected by depletion of host cell energy. The metabolic consequence of the interruption of heme biosynthesis is porphyria (Ellefson, R. D., *Mayo Clinic Proceedings*, 57:454–458 (1982); Hindmarsh, J. T., *Clin. Chem.*, 32:1255–1263 (1986); Meola, T. and Lim, H. W., *Bullous Diseases*, 11:583–596 (1993); Moore, M. R., *Int'l. Journ. of Biochem.*, 10:1353–1368 (1993)). Heme synthesis is a series of irreversible biochemical reactions of which some occur in the cell mitochondria and some in the cytoplasm. The intramitochondrial reactions are mainly oxidation-reduction while those in the cytosol are condensation and decarboxylation.

Porphyrinogens, porphyrins and porphyria are all related to heme synthesis. The biosynthesis of heme occurs in all human cells and involves a relatively small number of starting materials that are condensed to formn porphyrinogens; the porphyrins are formed from the porphyrinogens by non-enzymatic oxidation. As porphyrinogens progress through the heme biosynthesis pathway, the numbers of carboxyl side groups on the corresponding porphyrins decreases, as does the water solubility of the compounds.

The porphyrias are consequences of any impairment of the formation of porphyrinogens or in their transformation to heme. Porphyrins are formed from porphyrinogens by non-enzymatic oxidation. Each of the various genetic porphyrias is linked to an enzyme deficiency in the heme biosynthesis pathway. As a consequence of the enzyme defects, there is increased activity of the initial and rate-controlling enzyme of this biosynthesis pathway that results in overproduction and increased excretion of porphyrinogen precursors and porphyrinogens. The steps of heme biosynthesis are laid out in Table 7.

TABLE 7

Simplified outline of enzymes and precursors in the Biosynthesis of Heme

| Enzyme | Other precursor | Inhibitor | Result[b] |
|---|---|---|---|
| Δ-ALA synthase | pyridoxal 5'-phosphate | heme | glycine and succinyl coenzyme A delta-aminolevulinic acid (Δ-ALA) |
| Δ-ALA dehydratase* |  | lead and heme | porphobilinogen (PBG) |
| PBG deaminase* |  |  | tetrapyrrole hydroxy-methylbilane |
| uroporphyrinogen-III cosynthase* |  |  | uroporphyrinogen-III[a] |
| uroporphyrinogen decarboxylase* |  |  | 7,6,5-carboxyl porphyrinogen-III |
| coproporphyrinogen oxidase |  |  | coproporphyrino-gen-III |
| protoporphyrinogen oxidase |  |  | protoporphyrinogen |
| protoporphyrinogen oxidase |  |  | protoporphyrin |
| ferrochelatase | ferrous ion |  | heme |

[a]In absence of this step, the symmetric uroporphyrinogen-I is formed
[b]Becomes precursor of the next step
*Present in circulating red cells When porphyrinogens accumulate due to enzymatic defects in the heme biosynthesis pathway, they are oxidized to photosensitizing porphyrins. Porphyrins are classified as photodynamic agents because they generally require superoxide/oxygen/electrons to exert their damaging biologic effects. Porphyrins may be converted from ground state to excited state molecules after absorption of radiation. Excited state porphyrins transfer energy to oxygen molecules and produce reactive oxygen species such as singlet oxygen, superoxide anion, super oxide radical, hydroxyl radical and hydrogen peroxide. Reactive oxygen species have been noted to disrupt membrane lipids, cytochrome P-450 and DNA structure. If these reactive oxygen species are released into the extracellular space, as seen in acute porphyria, autooxidation of surrounding tissue may result. Thus, the accumulation of porphyrinogens/porphyrins in human tissues and body fluids produces a condition of chronic system overload of oxidative stress with long term effects particularly noted for neural, hepatic and renal tissue.

B. Chlamydia and Secondary Porphyria

As mentioned, ferric/ferrous translocation is a critical step in the biosynthesis of heme as it catalyses the oxidative entry of coproporphyrinogen into the mitochondria matrix as protoporphyrin; Chlamydia interfere with this step by reducing electron transfer in the host cell. When coproporhyrinogen is unable to return to the mitochondrial matrix, it accumulates first in the cytosol and then in the extracellular milieu. Within the mitochondrial matrix, the final steps in the biosynthesis of heme are halted. Because the accumulation of heme within the mitochondrial matrix normally exerts a negative feedback on heme biosynthesis, the reduction of heme caused by the inability of coproporphyrinogen to return to the mitochondrial matrix results in the increased production of heme precursors such as Δ-ALA and PBG, the first and second products in heme biosynthesis. Thus, porphyrin precursors such as Δ-ALA and PBG begin to accumulate in the mitochondrial matrix, then in the cytosol, and then in the extracellular milieu.

Depletion of host cell energy by the intracellular infection with Chlamydia species causes additional energy-related complications. As fewer electrons are available to move through the electron transport chain of the host cell mitochondrial matrix membrane, the citric acid cycle produces more succinyl-CoA which, in turn, promotes increased synthesis of Δ-ALA. The net result is an increased amount of heme precursors which become porphyrins. The presence of porphyrins in the mitochondrial matrix damages the cell as these molecules are unstable and form free radicals. The high energy electrons generated by these free radicals is "captured" by ubiquinone and cytochrome c which are present in the mitochondrial matrix membrane. This, of course, effectively uncouples electron transport from ATP synthesis and "short circuits" the proton-motice force: ATP synthesis is then reduced. Less ATP, in turn, means increased porphyrins and a destructive cycle is begun.

The clinical result of the intracellular and extracellular accumulation of porphyrins, if extensive, is a tissue/organ specific porphyria which produces many of the classical manifestations of hereditary porphyria. As the chlamydial-infected host cells lyse, as happens in the normal life cycle of Chlamydia, the intracellular porphyrins are released and result in a secondary porphyria. Moreover, when the chlamydial infection involves hepatic cells, the use of any pharmacologic agents that are metabolized by cytochrome P-450 in the liver will increase the need for cytochrome P-450, which is a heme-based enzyme. Hence, the biosynthesis of heme in the liver becomes increased. When hepatic cells are infected with Chlamydia species, the decreased energy in the host cell does not allow heme biosynthesis to go to completion and porphyrins in the liver/entero-hepatic circulation are increased. It also has been noted that any host cell infected with Chlamydia species has an increased amount of intracellular porphyrins that are released when antimicrobial agents kill the microorganism.

Although a number of investigators have reported enigmatic porphyria in patients who had no evidence of abnormal enzymes in the heme biosynthesis pathway (Yeung Laiwah et al., *Lancet*, i:790–792 (1983); Mustajoki, P. and Tenhunen, R., *Europ. Journ. of Clin. Invest.*, 15:281–284 (1985)), the intrinsic secondary, obligatory porphyria caused by chlamydial infection disclosed herein has neither been described nor hypothesized in the medical literature. This obligatory secondary porphyria clearly is of paramount importance in dealing with chronic systemic chlamydial infections as are seen with intravascular infections caused by *Chlamydia pneumoniae*.

The diagnosis of chlarnydial-associated secondary porphyria is important because of the well known neuropsychiatiric manifestations of porphyrias (Gibson et al., *Journal of Pathology and Bacteriology*, 71:495–509 (1956); Bonkowsky et al., *Seminars in Liver Diseases*, 2:108–124 (1982); Brennan et al., *International Journal of Biochemistry*, 833–835 (1980); Burgoyne et al., *Psychotherapy and Psychosomatics*, 64:121–131 (1995)). Moreover, chronic exposure to excess porphyrins has been associated with cancer (Kordac V., *Neoplasma*, 19:135–139 (1972); Lithner et al., *Acta Medica Scandanavia*, 215:271–274 (1984)). Of particular interest is that infection with *Chlamydia pneumoniae* has been associated with lung cancer (Cerutti P A., *Science*, 227:375–381 (1985)).

The diagnosis of genetic porphyria in patients with systemic chlamydial infections is important as these patients may precipitate a severe porphyric attack when they receive antimicrobial agents to treat their infection. Thus, in order to control the severe porphyria, these patients may require intravenous hematin and/or plasmapheresis in addition to the oral anti-porphyric agents. In contrast, the diagnosis of chlamydial-associated secondary porphyria may be difficult as the porphyria may be minimal and tissue-specific. The measurement of 24 hour urine porphyrins is not sensitive enough in every case of chlamydial infection to detect the secondary porphyria caused by chlamydial infection.

In view of the foregoing discussion of the etiology of porphyria, one aspect of the invention pertains to methods for differentiating porphyria caused by Chlamydia from that caused by a latent genetic disorder in an individual. The method comprises treating infection by Chlamydia at all stages of its life cycle, using the therapies described in detail elsewhere in this disclosure, and then assessing whether symptoms of porphyria have been reduced. A reduction in the symptoms of porphyria (e.g., biochemical, enzymatic or physical manifestation) are indicative that the porphyria is a secondary porphyria caused by Chlamydia.

The diagnosis of genetic porphyria is most easily done during an acute porphyric attack as there are porphyrinogen precursors and porphyrins in the blood, urine and stool (Kauppinen et al., *British Journal of Cancer*, 57:117–120 (1988)). The diagnosis of secondary porphyria is not as easy to do as there may not be an abnormal amount of porphyrinogen precursors and porphyrins in the blood, urine, or stool. However, several early enzymes in the pathway for heme biosynthesis can be readily measured in peripheral red blood cell (Percy et al., *South African Forensic Medicine Journal*, 52:219–222 (1977); Welland et al., *Metabolism*, 13:232–250 (1964); McColl et al., *Journal of Medical Genetics*, 19:271–276 (1982)). Specific hereditary porphyrias that can be diagnosed with the measurement of low levels of peripheral red blood cell enzymes are acute intermittent porphyria, congenital erythropoietic porphyria, Δ-aminolevulinic acid dehydratase deficiency porphyria, and porphyria cutanea tarda. Therefore, elevated porphyrin levels in patients who do not have low levels of these enzymes is suggestive of a non-genetic porphyria, such as chlamydially induced secondary porphyria. For example, in one embodiment, porphyria caused by Chlamydia in an individual having symptoms associated therewith can be diagnosed by determining the presence and/or amount of obligatory enzymes in heme biosynthesis in red blood cells of the individual. The presence or amount of the obligatory enzyme is compared to a normal patient who does not have porphyria or to an earlier test result in the patient to determine the patient's porphyria symptoms and/or whether therapy is effective. For example, the presence of ALA synthase and/or PBF deaminase or any of the other known enzymes involved in heme biosynthesis (see Table 7), in abnormal levels (i.e., significant deviation from normal levels in healthy patients who do not have genetic porphyria) is indicative of secondary porphyria.

The diagnosis of chlamydial-associated secondary porphyria may be difficult as the porphyria may be minimal and tissue-specific. The measurement of 24 hour urine or stool porphyrins may not be sensitive enough in many cases of chlamydial infection to detect the secondary porphyria. Here, the diagnosis depends on the fact that if excess porphyrins are reaching the circulation, the precursor red blood cells will absorb these and make heme. Thus, the enzymes for heme biosynthesis in the differentiated red blood cell become elevated and remain elevated for the life of the red cell. This allows the diagnosis of episodic low-level secondary porphyria as is seen with chlamydial infections. Thus, elevated heme synthesis levels can be used to diagnose intracellular porphyria. See Example 7.

As discussed above, some patients having a Chlamydia-induced porphyria do not have abnormal levels of heme precursors. For those patients it may be appropriate to determine the presence of Chlamydia as well as porphyrins in the individual. The presence of both the pathogen and porphyrins (e.g., determined by ELISA assay described below) is indicative of secondary chlamydial porphyria, rather than a genetic based porphyria. A proper diagnosis can thus determine the therapeutic regimen needed to treat infection and symptoms of secondary porphyria.

The inventors have discovered the existence of antibodies to the various metabolites of heme biosynthesis, as well as Vitamin B12 (cobalamin), which is molecularly similar to these metabolites, in patients with active systemic infection with *C. pneumoniae*. The antibodies are primarily IgM; this is similar to the antibody responses to the MOMP of *C. pneumoniae* in severely symptomatic patients. Example 8 illustrates titers in symptomatic patients with systemic *C. pneumoniae* infections. The presence of antibodies to Vitamin B12 may have functional significance by decreasing the amount of bioavilable Vitamin B12. Thus, a Chlamydia infection may cause a previously unrecognized secondary Vitamin B12 deficiency. Administration (e.g., intramuscular) of large quantities of Vitamin B12 (1000 to 5000 $\mu$g) (e.g., parenteral cobalamin therapy) creates large amounts of Vitamin B12 available for binding to the native receptors of antibodies with an affinity for Vitamin B12, thereby saturating these anti-Vitamin B12 antibodies and increasing the amount of bioavailable circulating Vitamin B12.

The previously unknown fact that the body produces antibodies to porphyrins makes it possible to diagnose the presence of porphyrins in a patient or animal by determining the presence of anti-porphyrin antibodies. The inventors have developed a method in which IgM and IgG antibodies to porphyrins can be measured with an ELISA method. This has been shown to be a much more accurate method to determine the chronic presence of porphyrins.

Porphyrins can also be used to create monoclonal and polyclonal antibodies using standard methods known to any one skilled in the field. These antibodies can be used in a variety of diagnostic assays and anti-porphyrin therapeutic strategies.

Treatment of Chlamydia infection may exaserbate secondary porphyria by increasing the metabolism of cryptic Chlamydia or by accelerating the death of infected cells with elevated intracellular porphyrin levels.

Once secondary porphyria is diagnosed, chlamydial infection and symptoms associated with porphyria can be treated. lThe following therapeutic regimen is aimed at controlling the chlamydial-associated secondary/obligatory porphyria, symptoms of which can actually increase during antimicrobial therapy of the chlamydial infection. This porphyric reaction to antimicrobial therapy should be recognized as such and differentiated from the expected cytokine-mediated immune response precipitated by antigen dump during anti-chlamydial therapy. These obligatory and secondary chlamydial metabolic disorders are treated by specific diets and a combination of pharmacological agents, each directed at different aspects of the metabolic disorders. For example, chlamydial-induced porphyria can be treated with a specific antiporphyric diet and a combination of antiporphyric agents, each directed at different aspects of porphyrins/porphyria. For purposes of this invention, the term "antiporphyric agent(s)" is intended to embrace any of the therapies described herein for management of porphyria. In addition to the antiporphyric diet and antiporphyric agents, the patient may require intravenous glucose and hematin, renal dialysis, and/or plasmaphoresis, particularly for those patients having both genetic porphyria and secondary porphyria induced by a chlamydial infection. Suitable diets and antiporphyric agents are described in detail below.

C. Therapies to Enhance Cellular Function

Glucose is an important source of cellular energy. Glucose levels can be enhanced by diet and through vitamin supplements as described below.

A high carbohydrate diet should be maintained to promote production of glucose (Pierach et al., *Journal of the American Medical Association*, 257:60–61 (1987)). Approximately 70% of the caloric intake should be in the form of complex carbohydrates such as bread, potato, rice and pasta. The remaining 30% of the daily diet should comprise protein and fat, which should ideally be in the form of fish or chicken. Red meats, including beef, dark turkey, tuna and salmon, contain tryprophan. Increased levels of tryptophan in the liver inhibit the activity of phosphoenol pyruvate carboxykinase with consequent disruption of gluconeogenesis. This accounts for the abnormal glucose tolerance seen in porphyria. Increased plasmic concentrations of tryptophan also enhances tryptophan transport into the brain. The concentration of tryptophan in the brain is the rate-limiting factor for the synthesis of the neurotransmitter 5-hydroxytryptariine (5-HT, serotonin). Serotonin is synthesized by the endothelium of brain capillaries for circulating tryptophan. Thus, increased concentrations of tryptophan in the brain would be expected to enhance production of serotonin and its metabolic, 5-hydroxyindole-acetic acid (5HIAA). Acute increases in serotonin turnover in the brain are followed by vascular and metabolic changes which include decreases in glucose consumption, disturbances in EEG tracings, and decreases in the postischemic neurological score. In addition, while serotonin increases brain perfusion on a single injection, repetitive administration initially opens the blood-brain barrier and subsequently induces vasoconstriction. It is likely that any transient opening of the blood-brain barrier by serotonin could allow circulating substrates such as ALA and PBG, if present, to enter the central nervous system. As would be expected from the location of serotonin receptors and from the barrier function of the endothelium of cerebral arteries, the constricting effect of serotonin is amplified in cerebral arteries where endothelium is damage or removed. Damaged endothelial cells, as would be expected with chlamydial infection, would no longer have operational catabolic processes for serotonin. This would be particularly true in the event of depleted ATP as caused by chlamydial infection. This means that increased concentrations of serotonin will reach the smooth muscle layer of the cerebral vessels and cause more constriction. Finally, serotonin is also stored in blood platelets. Because blood platelets do not adhere and aggregate under normal conditions, they do not release serotonin when the vessel lumen is intact. However. if the vessel lumen is altered by chlamydial infection, platelet deposition and release of serotonin can occur.

Another adverse effect of increased serotonin levels due to porphyria is seen with nervous tissues. Sympathetic nerve endings store serotonin taken up from the circulation. These serotonergic neurons form plexuses around brain vessels where they are likely to liberate their serotonin contents when subjected to cellular lysis from any cause including, ischemia, fiee-radical ionizing damage to cell membranes, and/or chlamydial infection.

In rats, elevated circulating tryptophan has been shown to produce structural alteration of brain astrocytes, oligodendroglia, and neurons, as well as degeneration of Purkinje cells and wasting of axons. Similar neurohistological alterations have been reported in patients with acute porphyria. Elevated tryptophan levels in plasma and brain have been associated with human encephalopathy. Finally, serotonin is also recognized as an active neurotransmitter in the gastrointestinal tract. The pharmacologic effects of serotonin in the central nervous system and gastrointestinal tract resemble the neurological manifestations of acute porphyric attacks. In fact, administration of either tryptophan or serotonin to humans have been reported to cause severe abdominal pain, psychomotor disturbances, nausea, and dysuria; all of which are symptoms of acute porphyria.

Sucrose and fructose should be avoided (Bottomly et al., *American Journal of Clinical Pathology*, 76:133–139 (1981)) because the ingestion of large amounts of fructose trigger hepatic gluconeogenesis which then decreases the available glucose which is derived from glycogen breakdown within the liver. It is recommended that sport drinks which contain glucose be consumed.

It is recommended that a patient suffering from porphyria avoid milk products. Milk products contain lactose and lactoferrin, and have been empirically shown to make symptoms of porphyria worse.

Multivitamins containing the B complex vitamins should be administered daily (e.g., one or multiple times), preferably in excess of RDA, to enhance glucose availability. Hepatic breakdown of glycogen with generation of glucose is assisted by taking these multivitamins that contain the B complex vitamins. Pyridoxine minimizes the porphyrin related porphyrial neuropathy. B complex vitamins include folic acid (e.g., 400 µg per dosage; 1200 µg daily maximum); vitamin B-1 (thiamin; e.g., 10 mg per dosage; 30 mg daily maximum); B-2 (riboflavin; e.g., 10 mg per dosage; 30 mg daily maximum); B-5 (panothenate; e.g., 100 mg per dosage; 300 mg daily maximum); B-6 (pyridoxine; e.g., 100 mg per dosage; 300 mg daily maximum) or pyridoxal-5-phosphate (e.g., 25 mg per dosage; 100 mg daily maximum) and B-12 (e.g., 500 µg per dosage; 10,000 µg daily maximum). The preferred method of administration is oral for the majority of these vitamins (twice daily), except for B-12 for which sublingual administration (three-times daily) is preferred. It has been discovered that one important effect of this secondary porphyria in some patients is the production of IgM and IgG antibodies against coproporphyrinogen-III. These antibodies cross-react with Vitamin B12 (cobalamin) and can thus cause a deficiency. Vitamin B12 supplementation (e.g., parenteral cobalamin therapy) can remedy the deficiency.

D. Reducing Porphyrin Levels

Dietary and pharmaceutical methods can be used to reduce systemic porphyrin levels (both water-soluble and fat-soluble).

Plenty of oral fluids in the form of bicarbonated water or "sports drinks" (i.e., water with glucose and salts) should be incorporated into the regimen. This flushes water-soluble porphyrins from the patient's system. Drinking seltzer water is the easiest way to achieve this goal. The color of the urine should always be almost clear instead of yellow. It is noted that dehydration concentrates prophyrins and makes patients more symptomatic.

Activated charcoal can be daily administered in an amount sufficient to absorb fat-soluble porphyrins from the enterohepatic circulation. Treatment with activated oral charcoal, which is nonabsorbable and binds porphyrins in the gastrointestinal tract and hence interrupts their enterohepatic circulation, has been associated with a decrease of plasma and skin porphyrin levels. Charcoal should be taken between meals and without any other oral drugs or.the charcoal will absorb the food or drugs rather than the porphyrins. For those who have difficulty taking the charcoal due to other medications being taken during the day, the charcoal can be taken all at one time before bed. Taking between 2 and 20 grams, preferably at least 6 grams (24×250 mg capsules) of activated charcoal per day (Perlroth et al., *Metabolism*, 17:571–581 (1968)) is recommended. Much more charcoal can be safely taken; up to 20 grams six times a day for nine months has been taken without any side effects.

For severe porphyria, chelating and other agents may be administered, singularly or in combination, to reduce levels of porphyrins in the blood. Examples of chelating agents include but are not limited to Kemet (succimer; from about 10 mg/kg to about 30 mg/kg); ethylene diamine tetracetic acid (EDTA); BAL (dimercaprol; e.g., 5 mg/kg maximum tolerated dosage every four hours), edetate calcium disodium (e.g., from about 1000 mg/m$^2$ to about 5000 mg/m$^2$ per day; can be used in combination with BAL); deferoxamine mesylate (e.g., from about 500 mg to about 6000 mg per day); trientine hydrochloride (e.g., from about 500 mg to about 3g per day); panhematin (e.g., from about 1 mg/kg to about 6 mg/kg per day), penacillamine. Intravenous hematin may also be administered. Quinine derivatives, such as but limited to hydroxychloroquine, chloroquine and quinacrine, should be administered to the patient daily at a dosage of from about 100 mg to about 400 mg per day, preferably about 200 mg once or twice per day with a maximum daily dose of 1 g. Hydrochloroquine is most preferred. The mechanism of action of hydroxychloroquine is thought to involve the formation of a water-soluble drug-porphyria complex which is removed from the liver and excreted in the urine (Tschudy et al., *Metabolism*, 13:396–406 (1964); Primstone et al., *The New England Journal of Medicine*, 316:390–393 (1987)).

To reduce severe porphyric attacks during therapy for chronic Chlamydia infections, the use of hemodialysis. plasmapheresis, chelating agents and/or intravenous hematin may be needed. Any one of these or a combination thereof can be used to treat the patient and is well within the knowledge of the skilled artisan how to carry out these adjunct therapies.

E. Mitigating the Effects of Porphyrins

Antioxidants at high dosages (preferably taken twice per day) help to mitigate the effects of free radicals produced by porphyrins. Examples of suitable antioxidants include but are not limited to Vitamin C (e.g., 1 gram per dosage; 10 g daily maximum); Vitamin E (e.g., 400 units per dosage; 3000 daily maximum); L-Carnitine (e.g., 500 mg per dosage; 3 g daily maximum); coenzyme Q-10 (uniquinone (e.g., 30 mg per dosage; 200 mg daily maximum); biotin (e.g., 5 mg per dosage; 20 mg daily maximum); lipoic acid (e.g., 400 mg per dosage; 1 g daily maximum); selenium (e.g., 100 μg per dosage; 300 μg daily maximum); gultamine (e.g., from 2 to about 4 g per dosage); glucosamine (e.g., from about 750 to about 1000 mg per dosage); and chondroitin sulfate (e.g., from about 250 to about 500 mg per dosage).

The above-mentioned therapeutic diets can be combined with traditional or currently recognized drug therapies for porphyria. In one embodiment, benzodiazapine drugs, such as but not limited to valium, klonafin, flurazepam hydrochloride (e.g., Dalmane™, Roche) and alprazolam (e.g., Xanax), can be administered. Preferably, sedatives, such as alprazolam (e.g., Xanax; 0.5 mg per dosage for 3 to 4 times daily), can be prescribed for panic attacks and flurazepam hydrochloride (e.g., Dalmane™, Roche or Restoril™ (e.g., 30 mg per dosage)) can be prescribed for sleeping. The rationale is based upon the presence of peripheral benzodiazepine receptors in high quantities in phagocytic cells known to produce high levels of radical oxygen species. A protective role against hydrogen peroxide has been demonstrated for peripheral benzodiazipine receptors. This suggests that these receptors may prevent mitochondria from radical damages and thereby regulate apoptosis in the hematopoietic system. Benzodiazepines have also been shown to interfere with the intracellular circulation of heme and porphyrinogens (Scholnick et al., *Journal of Investigative Dermatology*, 1973, 61:226–232). This is likely to decrease porphyrins and their adverse effects. The specific benzodiazipine will depend on the porphyrin-related symptoms.

Cimetidine can also be administered separately or in combination with benzodiazepine drugs. Cimetidine has been shown to effectively scavenge hydroxyl radicals although it is an ineffective scavenger for superoxide anion and hydrogen peroxide. Cimetidine appears to be able to bind and inactivate iron, which further emphasizes its antioxidant capacity. Cimetidine also is an effective scavenger for hypochlorous acid and monochloramine, which are cytotoxic oxidants arising from inflammatory cells, such as neutrophils. Cimetidine thus would be expected to be useful for the therapy of free-radical-mediated oxidative damage caused by chlamydial porphyria. Recent studies in Japan have found that cimetadine is effective for treating porphyria. The recommended amount of cimetadine is about 400 mg once or twice per day.

The complexity of the chlamydial life cycle. the host response to infection as well as to therapy, the high frequency of untoward side effects of antimicrobial therapy, the obligatory metabolic disorders. and the need for prolonged therapy make patient education, monitoring and support a necessary and key factor in the successful erradication of chronic/systemic chlamydial infections. When the presence of chlamydial in the blood is detected by culture and/or PCR and the IgM and IgG antibody titers are elevated, a presumptive diagnosis of chronic/systemic chlamydial infection is made. The potential for secondary effects such as porphyria should then be screened. For example, this can be evaluated by performing one or a combination of the following tests: 1) complete blood count (CBC); 2) Liver function tests; 3) Uric acid; 4) Serum iron studies; 5) IgM and IgG antibodies to coproporpyrinogen-III and Vitamin B12; and, 6) ALA dehydratase and PBG deaminase. Urine and stool samples should also be tested for presence of porphyrins, preferably using 24 hour samples. In a preferred embodiment of the therapeutic regimen, the patient is placed on the antiporphyric regimen, preferably for at least two weeks before any antibiotics are started. Following this, a reducing agent is started. These include amoxicillin (500 mg every 12 hours), penicillamine (250 mg every 12 hours), and cycloserine (250 mg every 12 hours). The patient is closely monitored for at least two weeks on this regimen to determine if any side effects occur. This regimen is continued for the entire course of therapy and is critical as it decreases the EB load. After the patient has adjusted to the amoxicillin or penicillamine, a combination of antimicrobial agents is added. The patient is closely monitored to determine tolerance to the antimicrobial agents.

Vitamins, antioxidants and other antiporphyric agents can be incorporated, in the amounts described herein, into nutraceuticals, medical foods, dietary supplements and dietary nutritional formulations including beverages and foods such as nutritional bar, for the management of non-genetic, secondary porphyria caused by a Chlamydia infection. Alternatively, a combination of vitamins and antioxidants can be co-packed in a pack or kit as described elsewhere herein and/or co-formulated into a composition in amounts suitable for administration to an individual having non-genetic, secondary prophyria.

Modes of Administration

Based upon the ability of the combination therapy of this invention to improve both the serological and physical status of a patient undergoing treatment, pharmaceutical compositions or preparations can be made comprising at least two different agents chosen from the following groups: a) at least one agent targeted against elementary body phase of chlamydial life cycle (e.g., disulfide reducing agents); b) at least one agent targeted against replicating phase of chlamydial life cycle (e.g., antimycobacterial agents); and c) at least one agent targeted against cryptic phase of chlamydial life cycle (e.g. anerobic bactericidal agents). As discussed in greater detail below, the agents can be formulated in a physiologically acceptable vehicle in a form which will be dependent upon the method in which it is administered.

In another aspect, the invention pertains to a combination of agents comprising at least two agents, each of which is targeted against a different phase of the chlamydial life cycle, as previously discussed. The combination of antichlamydial agents can be used in the management of chlamydial infection or prophylaxis thereof to prevent recurrent infection. The combination of agents can be in the form of an admixture, as a pack (discussed in detail below) or individually, and/or by virtue of the instruction to produce such a combination. It should be understood that combination therapy can comprise multiple agents that are effective within a particular phase of the chlamydial life cycle. The combination of antichlamydial agents can further comprise immunosuppressants, anti-inflammatory agents, vitamin C and combinations thereof.

In a preferred embodiment. if only one antichlamydial agent is elected to be used in an asymptomatic patient to reduce/prevent chronic infection, this agent is a reducing agent, such as penicillamine.

The novel therapeutic methods described herein can be used to ameliorate conditions/symptoms associated with the disease states described above, when the disease is onset or aggravated by infection by Chlamydia. The agents of this invention can be administered to animals including, but not limited to, fish, amphibians, reptiles, avians and mammals including humans. Compounds and agents described herein can be administered to an individual using standard methods and modes which are typically routine for the disease state.

Combination(s) of antichiamydial agents of this invention can be used for the manufacture of a medicament for simultaneous, separate or sequential use in managing chlamydial infection or prophylaxis thereof. The agents can also be used for the manufacture of a medicament for therapy of a disease associated with chlamydia infection, such as autoimmune disease, inflammatory disease, immunodeficiency disease.

The agents can be administered subcutaneously, intravenously, parenterally, intraperitoneally, intradermally, intramuscularly, topically, enteral (e.g., orally), sublingually, rectally, nasally, buccally, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, via nose drops, aerosols, inhalants, nebulizers, eye drops or suppositories can be used. The compounds and agents of this invention can be administered together with other biologically active agents.

In a specific embodiment, it may be desirable to administer the agents of the invention locally to a localized area in need of treatment; this may be achieved by, for example, and not by way of limitation, local infusion during surgery, topical application (e.g., for skin conditions such as psoriasis), transdermal patches, by injection, by means of a catheter, by means of a suppository, or by means of an implant, said implant being of a porous, non-porous, or gelatinous material, including membranes, such as sialastic membranes or fibers. For example, the agent can be injected into the joints.

In a specific embodiment when it is desirable to direct the drug to the central nervous system, techniques which can opportunistically open the blood brain barrier for a time adequate to deliver the drug there through can be used. For example, a composition of 5% mannitose and water can be used. In another embodiment, the agents can be delivered to a fetus through the placenta since many of the agents are small enough to pass through the placental barrier.

The present invention also provides pharmaceutical compositions. Such compositions comprise a therapeutically (or prophylactically) effective amount of the agent, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, enemas, lotions, sols, liniments, salves. aerosols, etc., which are, if desired, sterilized or mixed with auxiliary agents, e.g., preservatives, stabilizers, wetting agents, buffers or salts for influencing osmotic pressure, etc. The drug may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammoniun, calcium, ferric hydroxides. isopropylamine, triethylamine, 2-ethylamino ethanol, histidine, procaine, etc.

The amount of agents which will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions and/or adjunct therapies of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

Diagnostic Reagents

The invention also provides a diagnostic reagent pack or kit comprising one or more containers filled with one or more of the ingredients used in the assays of the invention. Optionally associated with such container(s) can be a notice in the form prescribed by a governmental agency regulating the manufacture, use or sale of diagnostic products, which notice reflects approval by the aggency of manufacture, use of sale for human administration. The pack or kit can be labeled with information regarding mode of administration, sequence of execution (e.g., separately, sequentially or concurrently), or the like. The pack or kit can be a single unit assay or it can be a plurality of unit assays. In particular, the agents can be separated, mixed together in any combination, present in a single vial or tablet. For the purpose of this invention, unit assays is intended to mean materials sufficient to perform only a single assay.

The invention will be further illustrated by the following non-limiting examples of diagnostic and therapeutic methods. All percentages are by weight unless otherwise specified.

EXAMPLES

Example 1

Polymerase Chain Reaction (PCR) for the Full Length MOMP Gene of C. Pneumoniae and other Species of Chlamydia (Diagnostic)

a. Solution PCR

Serum, blood or tissue samples were pre-incubated in the presence of 10 μM dithiothreitol at room temperature for 2 hours to reduce the disulfide bonds and facilitate release of the outer shell of the elementary bodies. CSF and other body fluids are also suitable for use as described. Other suitable reducing agents for use in this step include, but are not limited to, succimer and glutathione (e.g., including, but not limited to, glutathione esters, other analogs and deriviatives). The failure to include a reducing agent initially may result in a negative PCR signal following the protease digestion step. Appropriate concentrations of these reducing agents can be readily determined by the skilled artisan without undue experimentation using the 10 μM concentration of dithiothreitol as a guideline. Alternatively, guanidine isothiocyanate may be substituted for the disulfide reduction/protease step. Table 8 shows the effect of various reducing agents on susceptibility of EBs to proteinase K digestion in order to allow DNA extraction for PCR amplification.

TABLE 8

Effect of various reducing agents on susceptibility of EBs to proteinase K digestion in order to allow DNA extraction for PCR amplification.

| Reducing Agent | Concentration | PCR Signal[a] |
|---|---|---|
| Dithiothreitol | 10 mM | + |
| | 1 mM | + |
| | 100 μM | + |
| | 10 μM | + |
| | 1 μM | + |
| Succimer | 10 mM | – |
| | 1 mM | + |
| | 100 μM | + |
| | 10 μM | + |
| | 1 μM | – |
| DL-Penicillamine | 10 mM | – |
| | 1 mM | – |
| | 100 μM | + |
| | 10 μM | – |
| | 1 μM | – |
| D-Penicillamine disulfide | 10 mM | + |
| | 1 mM | – |
| | 100 μM | – |
| | 10 μM | – |
| | 1 μM | – |
| 2,3-Dimercapto-1-Propone-sulfide acid | 10 mM | – |
| | 1 mM | – |
| | 100 μM | + |
| | 10 μM | – |
| | 1 μM | – |
| Meso-2,2'-Dimercapto adipic acid | 10 mM | + |
| | 1 mM | + |
| | 100 μM | + |
| | 10 μM | + |
| | 1 μM | – |
| Glutathione | 10 mM | – |
| | 1 mM | wk+ |
| | 100 μM | – |
| | 10 μM | +/– |
| | 1 μM | +/– |
| Control | 0 | – |

[a]All assays performed on control serum #1154, which on repeated assay without reducing agents, yields a negative PCR signal for the 1.2 kB MOMP gene of *C. pneumoniae*. Analysis on agarose gel with ethidium bromide visualization under UV light.

Serum, blood, or tissue samples are lysed overnight at 37° C. in the presence of SDS which inhibits DNAses and proteinase K which digests protein (i.e., 2×cell lysis buffer: 1% SDS, 0.2 M NaCl, 10 mM EDTA, 20 mM Tris-KCl, pH 7.5 plus proteinase K to a final concentration of 20 mg/ml). Following digestion, the lysate is extracted×1 with phenol-followed by chloroform extraction×2. DNA is precipitated from the final aqueous phase by the addition of 1/10 volume Na acetate (3 M) and 2–2.5 volume of cold ethanol. The DNA is pelleted by centrifugation and the DNA is resuspended in 10–20 μl water with PCR amplification performed in the same microtube. The entire gene of MOMP (1.2 kb) is amplified using the CHLMOMPDB2 coding strand primer (5'-ATGAAAAAAC TCTTAAAGTC GGCGTTATTA TCCGCCGC; SEQ ID NO. 41) and the CHLMOMPCB2 complimentary strand primer (5'-TTAGAATCTG AACTGACCAG ATACGTGAGC AGCTCTCTCG; SEQ ID NO. 42). Alternatively, shortened primers can be used by making suitable modifications in the primer:DNA hybridization temperature for PCR detection only. The appropriate primer selection, however, may result in the absence of signal if an unknown strain with mutations in one or both primer binding regions is present. The frequency of positive signals using the preferred primers which amplify the full length MOMP gene suggests that mutations in these regions of *C. pneumoniae* is rare. Standard conditions for this gene product in a 50-μl volume is 35 cycles with 1 second ramp times between steps of 94° C. for 1 minute, 58° C. for 2 minutes and 74° C. for 3 minutes. The PCR reaction used 0.1 mM of each primer in Deep Vent buffer with 200 mM of each dNTP, and 1.0 U Deep Vent DNA polymerase. Amplified DNA is separated and identified by electrophoresis in 1.2% agarose or 6% polyacrylamide gels run in the TBE buffer (88 mM Tris-borate, 89 mM boric acid, 2 mM EDTA) at 120 volts for 1 hour. DNA bands are identified by ethidium bromide staining and UV light detection. Product specificity has been verified by restriction enzyme analysis of cleavage products as well as DNA sequence analysis. Negative controls consist of amplification of lysis buffer extracts. Extreme care must be exercised to screen all components of the cell lysis and amplification buffer components to exclude contaminant MOMP DNA which are common contaminants in such lab and molecular biology grade chemicals.

b. In situ PCR

This procedure identifies individual cells containing RB and cryptic forms of C. pneumoniae. Cultured cells are adhered to glass slides with formalin, or formalin fixed tissue sections embedded in paraffin are adhered to glass slides and subjected to protease digestion (i.e., pepsin, trypsin, chymotrypsin, or other specific proteases). Each digestion time and pH (i.e., pepsin at pH 2.5 or trypsin at pH 7–8, etc.) with a standard concentration of each protease must be evaluated for each tissue type for optimal digestion times. Protease activity is stopped by washing and/or pH change and the target cells exposed to Taq polymerase, dNTPs, and primers. For the MOMP gene the primers CHLMOMPDB2 and CHLMOMPCB2 have been engineered with a biotin at the 5'-terminus. For in situ PCR, using biotin labels incorporated at the 5'-terminus of the amplification primers, each DNA chain amplification results in each double strand DNA containing 2 molecules of biotin. Standard conditions of amplification are identical to solution PCR described above. Following the end of the PCR cycle, the slides are washed and exposed to strepavidin-P-galactosidase (or other strepavidin conjugated signal enzyme). Visualization of the amplified MOMP gene is accomplished by bound enzyme hydrolysis of soluble substrate yielding an insoluble product which can then be visualized by standard light microscopy.

Alternatively, other specific DNA sequences, including subsections of the full MOMP gene (e.g., subsections including gene sequences for the peptides in FIG. 4) can be used, although the above-described sequence is the preferred embodiment since the large product produced (1.2 kb) prevents diffusion that may be encountered with smaller DNA amplifications. Similarly, other detection labels can be incorporated (i.e., fluorescein, for example) at the 5'-end or dixoxigenin & UTP can be incorporated within the amplified DNA. Alternatively to labeling the product, specific hybridization probes to constant regions of the amplified DNA can be used to identify an amplified product. This latter method has particular utility for the construction of automated laboratory equipment for solution-based PCR. For example, strepavidin-coated ELISA plates can be used to capture one or both strands of a biotin 5'-labeled DNA with detection by fluorescence of a fluorescen or other incorporated fluorophore detection probe.

Example 2

Enzyme Linked Immuno Sorbent Assay (ELISA; Diagnostic)

a. Recombinant MOMP-based ELISA

The full length MOMP gene of C. pneumoniae was directionally cloned into the pET expression plasmid at the NCOI and NOTI restriction sites using primers to introduce these unique restriction sites into the MOMP ends. Primer sequences are as follows:

CPOMPDNCO (Coding strand): 5'-AGCTTACCAT GGCTAAAAAA CTCTTAAAGT CGGCGTTATT ATCCG-3'(SEQ ID NO. 43)

CPOMP_CNOT (complimentary strand): 5'-ATATGCGGCC GCTCATAGAA TCTGAACTGA CCAGATACG-3'(SEQ ID NO. 43)

The construction of the MOMP insert into the pET expression vector (Novagen, Inc.) yields, on transformation of permissive E. coli, an amino terminal thioredoxin fusion domain, a polyhistidine for $Ni^+$-affinity chromatography, a solubility sequence of approximately 5 kD, and an endopeptidase cleavage site which yields a full length MOMP with a modified amino terminal (as illustrated in FIG. 2) containing an alanine insert between the amino terminal methionine and the adjacent lysine. Either the full length expressed recombinant fusion protein or the modified MOMP following endopeptidase cleavage can be used as the antigen for a Chlamydia species ELISA. Other expression systems in E. coli or Baculovirus can be used for synthesis of the MOMP protein as the antigen in ELISA. The process is performed by non-covalent attachment of 50 ng recombinant MOMP in each well (rows 1–11) of a 96 well microtiter plate (Immulon 4) in carbonate buffer at pH 9.5 with an overnight incubation at 4° C. The plate is washed with PBS, 0.15% Tween20×3 and is then blocked with PBS, 1% BSA, 0.15% Tween, 20 at 300 ml per well for 1 hour at RT and then washed×3 with PBS, 0.15% Tween20. Serum is serially diluted in PBS in triplicate in a separate plate and 50 μl of each well transferred to corresponding wells of a MOMP ligand plate, and the following sequence is followed: incubate at 37° C. for 1 hour using a parafilm or other suitable cover to prevent non-uniform evaporation. Wash with PBS, 1% FCS, 0.05% $NaN_3$×5. Incubate each well with a predetermined dilution of biotin conjugated anti-human monoclonal IgG or monoclonal IgM. Incubate at 37° C. for 1 hour with cover. Wash (×3) with PBS, 1% FCS, 0.05% $NaN_3$. Follow with 50 μl strepavidin-alkaline phosphatase conjugate (1:200 in PBS, 1% BSA, 0.15% Tween20) for 1 hour at 37° C. with cover. Wash×3 with PBS, 1% CS (calf serum), 0.05% $NaN_3$. Color is developed with p-nitrophenyl phosphate in glycine buffer at pH 9.6. The color yield is measured on a microtiter calorimeter using a 405 nm filter. The end point titer is the highest dilution of serum or secretion yielding a color yield >3 SD over background (n=8). Analysis is simplified by computer-generated end point antibody titer or other antibody level measure identification and/or quantity of specific antibody (IgG, IgM, or total Ig) in the test sample using appropriate controls. Other strepavidin or avidin enzyme conjugates can be substituted such as strepavidin peroxidase or strepavidin-galactosidase with an approximate substitute yielding a detectable color for quantitation.

b. Peptide-based ELISA

The recombinant MOMP-based ELISA described above provides a sensitive method for the quantitation of immunoglobulins against the Chlamydia genus in serum, plasma, CSF, and other body fluids. In order to provide ELISA assays that are species- and potentially strain-specific for the various Chlamydia, two regions in the MOMP have been identified which show minimal amino acid sequence homologies and which are predicted by computer analysis (Intelligenetics) to be excellent antigenic domains by virtue of hydrophilicity and mobility on the solvent-accessible surface of MOMP. FIG. 3 illustrates the constant and variable domain (VD) of the various chiamydial species. The identified species-specific antigenic domains are located in VD1 and VD2. FIG. 4 illustrates the peptide amino acid sequences employed for the construction of peptide based ELISAs with species specificity for VD1. FIG. 5 illustrates the peptides for VD2 which are used similarly to the VD1 sequences. ELISA methodology parallels that described above for the recombinant MOMP-based ELISA. In addition, a highly antigenic domain (FIG. 6) common to all Chlamydia has been identified and was developed as an alternative genus-specific ELISA for the Chiamydia. Immunization of rabbits has verified the antigenicity of each peptide to each peptide (Table 9). Monoclonal antibodies have fuirther verified the specificities and antigenicity of each peptide (Table 8) as predicted by computer analysis of the nucleotide-generated amino acid sequence of each species-specific MOMP.

TABLE 9

Antigenic Responses To Peptides From 4 Species of Chlamydia Identified By Hydrophilicity And Peptide Movement As Highly Antigenic

| Chlamydia | | Titer[a] | |
|---|---|---|---|
| Species | Peptide[b] | Pre | Post |
| *C. pneumoniae* | 90–105 | 100 | >3200 |
| *C. trachomatis L2* | 91–106 | 800 | >3200 |
| *C. psittaci* | 92–106 | 400 | >3200 |
| *C. trachomatis* (mouse) | 89–105 | 0 | >3200 |
| *C. pneumoniae* | 158–171 | 25 | >3200 |
| *C. trachomatis L2* | 159–175 | 200 | >3200 |
| *C. psittaci* | 160–172 | 100 | >3200 |
| *C. trachomatis* (mouse) | 158–171 | 800 | >3200 |
| *C. pneumoniae* | 342–354 | 200 | >3200 |
| *C. trachomatis L2* | 342–354 | 100 | >3200 |
| *C. psittaci* | ND[c] | | |
| *C. trachomatis* (mouse) | ND[c] | | |

[a]Reciprocal titer
[b]Immunogenic peptide and ELISA antigen of specific amino acid sequence against the indicated pre-immunization and post-immunization rabbit serum
[c]ND, not done Table 10 illustrates reciprocal titers of a polyclonal and monoclonal antibody against *C. trachomatis* cross-reactive against *C. pneumoniae* peptide encompassing amino acids 342–354 and a recombinant full length MOMP from *C. pneumoniae.*

TABLE 10

Reciprocal titers of a polyclonal and a monoclonal antibody against *C. trachomatis* cross-reactive against *C. pneumoniae* peptide encompassing amino acids 342–354 and a recombinant full length MOMP from *C. pneumoniae*

| | Titer[a] | |
|---|---|---|
| Antigen | Polyclonal Ab[b] | Monoclonal Ab[c] |
| CPN Momp[d] | 400 | 0 |
| CPN 90–105[e] | 50 | 0 |
| CPN 158–171[f] | 50 | 0 |
| CPN 342–354[g] | >3200 | 1600 |

[a]Reciprocal titer
[b]Polyclonal goat Ab from Chemicon Inc. against MOMP of *C. trachomatis*
[c]Monoclonal Ab (ICN, Inc.) against MOMP of *C. trachomatis*
[d]*C. pneumoniae* recombinant MOMP
[e]Amino acid peptide 90–105 of *C. pneumoniae*
[f]Amino acid peptide 158–171 of *C. pneumoniae*
[g]Amino acid peptide 342–354 of *C. pneumoniae*

Example 3

Detection Assay Methods (Diagnostic)

a. Imrnunoglobulin (Ig) Assay

*C. pneumoniae* EBs were grown in primary human umbilical vein endothelial cells (HuEVEC; early passage), HeLa 199, or a suitable alternative in the presence of 1 μg/ml cycloheximide at 35° C. under 5% $CO_2$. Permissive cells were lysed by sonication at 3 days, thereby liberating EBs. The latter were harvested from infection flasks, sonicated, and cellular debris were removed after sonication by a low speed centrifugation (~600×g) for 5 minutes. EBs were pelleted by high speed centrifugation (30,000×g) for 30 minutes at 4° C. The EB pellet was washed with PBS×1 and was reconstituted in 2 ml PBS per four 25-$cm^2$ culture flask and sonicated at maximum power for 20 seconds and a 0.5 cycle time using a Braun-Sonic U sonicator. EB protein concentration was determined by the Bradford method and the sonicated infectious EB suspension was rendered non-infectious by the addition of 37% formaldehyde to a final 10% formaldehyde concentration with constant agitation during addition. Formalin-treated EBs were added to 96-well plates at 50 μl per well containing 50 ng EB (total of 5 μg/plate) and air dried. The plate was washed with PBS-0.15% Tween20×3 and was then blocked with PBS-1% BSA-0.15% Tween20 at 300 μl per well for 1 hour at room temperature and then washed×3 with PBS-0.15% Tween20. Serum was serially diluted in PBS in duplicate in a separate plate and 50 μl of each well transferred to corresponding wells of a MOMP ligand plate and the following sequence was followed: incubate at 37° C. for 1 hour using a parafilm cover; wash with PBS-1% FCS-0.05% NaN3×5; incubate each well with a predetermined dilution of biotin-conjugated, antihuman monoclonal IgG or monoclonal IgM; incubate at 37° C. for 1 hour with cover; wash (×3) with PBS, 1% FCS, 0.05% NaN3; follow with 50 μl strepavidin-alkaline phosphatase conjugate (1:200 in PBS-1% BSA-0.15% Tween20) for 1 hour at 37° C. with cover; and wash×3 with PBS, 1% CS, 0.05% NaN3. Color was developed with p-nitrophenyl phosphate in glycine buffer at pH 9.6. The color yield was measured on a Flow microtiter colorimeter using a 405 nm filter. End point titer was the highest dilution of serum or secretion yielding a color yield >3 SD over background (n=8).

b. Western Blot

Western blots were prepared by SDS-PAGE of *C. pneumoniae* EBs (non-formalin fixed) harvested from infected HuEVEC or HeLa cell lysates, electrophoresed under standard SDS-PAGE conditions, and transferred to nitrocellulose achieved with an active diffusion transfer. Albumin-blocked strips were prepared from nitrocellulose sheets and incubated 1 hour with 1.2 ml of a 1:40 dilution of test serum. Detection was achieved with an alkaline phosphatase-conjugated, mouse anti-human antibody, and developed with 5-bromo-4-chloro-3'-indolyphosphate p-toluidine/nitro-blue tetrazolium chloride (BCIP/NBT, Pierce Chemical Company). Polyclonal animal anti-human antibodies can alternatively be used.

c. Antigen Capture Assay for Chlamydial MOMP

The peptides described in FIGS. 3–5 were conjugated via disulfide bonding to keyhole limpet hemocyanin (KLH) by standard methods (Bernatowicz et al., *Anal. Biochem.* 155 (1):95–102 (1986)). The peptide conjugates in alum were used to generate polyclonal and/or monoclonal antibodies to the species-specific domains of MOMP which is used as a capture antibody in 96 well microtiter plates. Final configuration can follow a number of alternative routes to yield quantitation of MOMP in body fluids. The favored configuration utilizes biotin labeled recombinant MOMP in a competition assay with strepavidin/alkaline phosphatase generated color development based on the quantity of biotinylated recombinant MOMP displaced by unlabeled MOMP in body fluids.

Example 4

In Vitro Antimicrobial Susceptibility Testing for *C. Pneumoniae*

Tissue culture cells containing cryptic phase *C. pneumoniae* (H-292, HeLa, HEL, HuEVEC, McCoy, etc.) are plated at subconfluency in a 96-well microtiter plate (flasks or plates or other configurations can be alternatively used) and cultured in the presence of various antibiotics (singly and in combination) with the medium changed daily. Analysis of chlamydiacidal activity is carried out by assessing loss of solution PCR signal, or relative activity can be quantified by dilution titer of the starting material using the absence of PCR signal as the endpoint titer (i.e., last dilution to yield specific PCR signal).

Two week exposure of single agents including the fluoroquinolone, ofloxacin, and the macrolide, clarithromycin, at 1 μg/ml failed to clear HeLa cells in culture of a detectable PCR signal for the MOMP gene of Chlamydia pneumoniae. In contrast, triple agents consisting of isoniazid (INH), metronidazole, and penicillamine (1 μg/ml each) resulted in no detectable PCR signal (Table 11). None of these agents, effective in the triple combination, is currently recognized as an anti-chlamydial agent.

Table 12 provides the results of an expanded study of antimicrobial susceptibilities at two different concentrations of antimicrobial agents, used alone and in combination, when exposed to the antimicrobial agents for two weeks. In addition to the agents already mentioned, minocycline, doxycycline, rifampin and sulfamethoxizole/trimethoprim, at all concentrations tested, failed to clear the PCR signal for chlamydial MOMP. Only the triple combination of isoniazid, metronidazole and penicillamine cleared the PCR signal in two weeks. The triple combination was effective at both low and high concentrations. Table 12 also demonstrates the effect of a 4 week exposure with the same expanded series of antimicrobial agents alone and in combination. A number of triple combinations of antimicrobial agents resulted in cell cultures in which the PCR signal for the chlamydial MOMP gene could not be detected at four weeks. The most effective combinations to have the greatest impact on the important life cycle phases are those predicted according to the methodology described in the section above entitled "Methodology for Selecting Potential Agent Combinations").

TABLE 11

Susceptibility to Antibiotics for Cryptic *C. pneumoniae* Cultured in HeLa Cells[a]

| Antibiotic | Conc (μg/ml) | PCR[b] |
|---|---|---|
| Ofloxacin | 1 | positive |
| Clarithromycin | 1 | positive |
| INH | 1 | positive |
| Metronidazole | 1 | positive |
| Penicillamine | 1/1 | positive |
| INH + Metronidazole + Penicillamine | 1/1/4 | negative |
| Control | 0 | positive |

[a]Cultured in the presence of the indicated antibiotic(s), but with no cycloheximide. Media changes at 48–72 hours.
[b]Analysis following 2 weeks exposure to antimicrobioal agents.

TABLE 12

Susceptibility to Antibiotics by PCR for Cryptic *Chlamydia pneumoniae* Cultured in HeLa Cells[1]

| Phase of the Chlamydial Life Cycle | | | | | | | | |
|---|---|---|---|---|---|---|---|---|
| EB (Extracellular or Intracellular) | EB->RB Transition | Stationary Phase RB ("Cryptic phase") | Replicating RB | RB->EB Transition ("Condensation") | Concentration (μg/ml) | PCR 2 week | PCR 4 week | Comment |
| | | | | | 0 | + | + | Control |
| | | | Minocycline | | 0.25 | + | + | One drug |
| | | | Minocycline | | 1 | + | + | One drug |
| | | | Doxycycline | | 0.25 | + | + | One drug |
| | | | Doxycycline | | 1 | + | + | One drug |
| | | | TMP/SMZ[2] | | 25 | + | + | One drug |
| | | | TMP/SMZ[2] | | 100 | + | + | One drug |
| | | | Clarithromycin | | 0.25 | + | + | One drug |
| | | | Ofloxacin | | 0.25 | + | + | One drug |
| | | Metronidazole | | | 0.25 | + | + | One drug |
| | Rifampin | | | | 0.25 | + | + | One drug |
| | | Isoniazide | Isoniazide | | 1 | + | + | Misses EB phase |
| | | Metronidazole | TMP/SMZ[1] | | 25/0.25 | + | + | Misses EB phase |
| | | Metronidazole | Ofloxacin | | 0.25/0.25 | + | + | Misses EB phase |
| | Rifampin | Metronidazole | | | 0.25/0.25 | + | + | Misses EB phase |
| penicillamine | Rifampin | Metronidazole | | penicillamine | 4/.25/.25 | + | + | Misses replicating phase |
| | Rifampin | Metronidazole | Ofloxacin | | .25/.25/.25 | + | + | Misses EB phase |
| penicillamine | | Metronidazole | Doxycyclin | penicillamine | 1/.25/.25 | + | + | Concentration too low |
| penicillamine | | Metronidazole | Doxycyclin | penicillamine | 4/1/1 | + | − | Covers key phases |

TABLE 12-continued Susceptibility to Antibiotics by PCR for
Cryptic *Chlamydia pneumoniae* Cultured in HeLa Cells[1]

| Phase of the Chlamydial Life Cycle | | | | Concentration ($\mu$g/ml) | PCR 2 week

TABLE 13a-continued

Serological and PCR Responses to Combination Antibiotic Therapy

| Patient | Diagnosis[a] | Titer IgM | IgG | Time on Therapy | PCR | Status |
|---|---|---|---|---|---|---|
| HS | MS | 2000 | 400 | 5 months | + | |
|  |  | 3200 | 800 |  | + | |
|  |  | 50 | 200 |  | – | Improvement |
| ST | CFS/FM | >1000 | 100 | 7 months | wk+ | |
|  |  | 1000 | 100 |  | wk+ | |
|  |  | 400 | 100 |  | + | |
|  |  | 800 | 3200 |  | + | |
|  |  | 100 | 100 |  | + | Asymptomatic |
| RV | CF | 1000 | 100 | 10 months | + | |
|  |  | 400 | 1600 |  | + | |
|  |  | 400 | 400 |  | – | Asymptomatic |

[a] CF = Chronic Fatigue < 6 months, CFS = Chronic Fatigue Syndrome, FM = Fibromyalgia, IBD = Inflammatory Bowel Disease, MS = Multiple Sclerosis, AND = Autonomic nervous dysfunction (neural-mediated hypotension), RA = Rheumatoid Arthritis
IgM >> IgG: immune tolerance to the antigen; IgG >> IgM: successful immune control of the antigen

TABLE 13b

Treatment Regimens

| Patient | Sex | Diag | EB (Extra- or Intracellular) | EB–>RB Transition | Stationary Phase RB | Replicating RB | RB–>EB Transition | Enhancer | Duration (months) | Comments |
|---|---|---|---|---|---|---|---|---|---|---|
| BL | M | MS |  |  | Rifampin | Flagyl | Floxin |  | 2 | |
|  |  |  |  |  |  | Flagyl | Bactrim, Levaquin |  | 5 | |
|  |  |  | — | — | — | — | — | — | 3 | Took a break, had relapse |
|  |  |  |  |  |  | Flagyl | Bactrim, Levaquin |  | 2 | |
|  |  |  | Penicillimine |  |  | Flagyl | Bactrim, Levaquin | Penicillimine | 7 | |
|  |  |  | Penicillimine | Rifampin | INH | INH | Penicillimine | Probenicid | 3 | |
| MC | M | MS |  | Rifampin | INH | INH |  |  | 9 | |
|  |  |  |  |  | Flagyl |  |  |  |  | |
|  |  |  |  |  |  | Levaquin Minocycline |  |  | 6 | Probably not compliant |
|  |  |  | — | — | — | — | — | — |  | Discontinued |
| JM | M | MS |  |  | Flagyl | Floxin Bactrim Minocycline |  |  | 7 | |
|  |  |  | Amoxicillin |  |  | Levaquin Bactrim | Amoxicillin |  | 4 | |
|  |  |  | Amoxicillin |  |  | Levaquin Bactrim | Amoxicillin | Probenicid | 3 | |
| LL | F | MS |  |  | Flagyl | Levaquin Minocycline |  |  | 15 | |
|  |  |  | Penicillimine |  |  | Levaquin Minocycline | Penicillimine | Probenicid | 1 | |
| AN | F | MS |  |  | Tenitizole | Floxin |  |  | ? | She was given a copy of the protocol, but ran her own therapy |
| FO | M | MS |  |  |  |  |  | Prednizone | 0.25 | Phased in over several days to mitigate effect of therapy |
|  |  |  |  |  | Flagyl | Biaxin |  |  | 2 | |
|  |  |  |  |  |  | Biaxin |  |  | 1 | Stopped flagyl due to persistance of side effects |
|  |  |  | Kemet |  |  | Biaxin | Kemet |  | 0.5 | |
|  |  |  | Kemet |  | Flagyl | Biaxin | Kemet |  | 6 | Began phasing Flagyl back in over a month |
|  |  |  | Kemet Amoxicillin |  | Flagyl | Biaxin | Kemet Amoxicillin |  | 1 | Began 2 week switchover to Amoxicillin |
|  |  |  | Amoxicillin |  | Flagyl | Biaxin | Amoxicillin |  | 2 | |
|  |  |  | Amoxicillin |  | Flagyl | Biaxin | Amoxicillin | Probenicid | 6 | Began 6 week phase in of probenicid |
| JC | F | MS | Amoxicillin |  |  |  | Amoxicillin |  | 1 | Phased in over 7 months . . . |
|  |  |  | Amoxicillin |  |  |  | Amoxicillin | Probenicid | 1 | |
|  |  |  | Amoxicillin |  |  | Bactrim | Amoxicillin | Probenicid | 1 | |
|  |  |  | Amoxicillin |  | INH | Bactrim | Amoxicillin | Probenicid | 7 | |

TABLE 13b-continued

Treatment Regimens

| | | | Treatment Regimen ||||||| |
|---|---|---|---|---|---|---|---|---|---|
| | | | Phase of Chlamydial Life Cycle ||||| | | |
| Patient | Sex | Diag | EB (Extra- or Intracellular) | EB->RB Transition | Stationary Phase RB | Replicating RB | RB->EB Transition | Enhancer | Duration (months) | Comments |
| FW | M | MS | Penicillimine | | Flagyl | Doxycycline | Penicillimine | | 7 | |
| | | | Penicillimine | | INH | INH Bactrim | Penicillimine | Probenicid | 5 | |
| | | | — | — | — | — | — | — | | Stopped treatment |
| LH | F | RA | Penicillimine | | Flagyl | Minocycline | Penicillimine | | 11 | |
| | | | Penicillimine | | Flagyl | Minocycline | Penicillimine | Probenicid | 3 | |
| | | | — | — | — | — | — | — | 3 | PCR negative, symptom free, but titer @ 1:800. Decided to stop. |
| | | | Penicillimine | | Flagyl | Minocycline | Penicillimine | Probenicid | 2 | After symptoms flared, PCR went positive, and titer to 1:1600, restarted therapy |
| XX | F | IC | Amoxicillin | | INH | INH Bactrim | Amixicillan | Probenicid | 4 | Symptoms gone after 4 months of treatment |
| NC | F | PG | Amox | | INH | INH Bactrim | Amoxicillin | | 7 | Continued improvement |
| CH | M | PG | Amoxicillin | | INH | IHN Levaquin | Amoxicillin | | 3 | |
| | | | Amoxicillin | | INH | IHN Bactrim | Amoxicillin | | 2 | |
| | | | — | — | — | — | — | — | | Discontinued after all ulcers cleared up except for those in poorly blood-supplied leg |
| RI | M | PG | | | | | | | | Missing patient chart |
| PL | M | PG | Amoxicillin | | INH | IHN Bactrim | Amoxicillin | | 2 | Non-compliant because could not afford medicines |
| | | | — | — | — | — | — | — | 1 | |
| | | | Amoxicillin | | INH | IHN Bactrim | Amoxicillin | | 0.5 | Would often only take what he had left. |
| | | | — | — | — | — | — | — | 2 | Off for 2 months, then flared |
| | | | Amoxicillin | | INH | IHN Zithromax | Amoxicillin | | 1 | No subsequent follow-up |
| TW | M | PG | | | Flagyl | Minocycline | | | 4 | |
| | | | Amoxicillin | | INH | INH Levaquin | Amoxicillin | | 2 | |
| | | | — | — | — | — | — | — | 1 | |
| | | | Amoxicillin | | | Levaquin | | | 4 | No improvement |
| | | | — | — | — | — | — | | | Moved to topical antibiotics |
| AM | M | UC | | | Flagyl | Biaxin | | | 11 | |
| | | | Amoxicillan | | Flagyl | Biaxin INH | Amoxicillan INH | | 2 | |
| | | | Amoxicillan | | Flagyl INH | Bactrim INH | Amoxicillan | Probenicid | 5 | Now doing very well |
| AG | F | UC | | | Flagyl | Doxycycline | | | 6 | |
| | | | — | — | — | — | — | | | Discontinued after symptoms resolved. |
| DM | F | IBD | | | Flagyl | Doxycycline | | | 7 | |
| | | | Cupramine[1] | | Flagyl | Doxycycline | Cupramine | Probenicid | 5 | |
| | | | — | — | — | — | — | — | | Discontinued after doing well clinically; wanted to start a family. |
| RP | F | UC | | | Flagyl | Biaxin | | | 5 | |
| | | | — | — | — | — | — | | | Discontinued after impvt |
| AB | F | CD | | | Flagyl | Doxycycline | | | 7 | |
| | | | — | — | — | — | — | | | Non-compliant |
| EU | F | UC | | | Flagyl | Doxycycline | | | 9 | |
| | | | — | — | — | — | — | | 1 | Stopped |
| | | | Amoxicillin | | Flagyl | Doxycycline | Amoxicillan | Probenicid | 2 | Restarted after symptoms flared. Now doing well again |
| RR | | CD | | | Flagyl | Doxycycline | | | 2 | Colectomy 2 months prior |
| | | | Amoxicillan | | Flagyl | Doxycycline | Amoxicillan | Probenicid | 6 | Now doing well; no evidence of active disease |

[1]125 mg BID

TABLE 13c

Detailed Case Histories

| Patient | Diag | Test data[1] | Case History |
|---|---|---|---|
| BL | MS | Row 2 | First symptoms began with numbness of the left arm and leg which rapidly progressed to a partial Brown-Sequard syndrome (i.e. -cord myelitis) with an associated urinary retention. Despite therapy with corticosteroids, and Beta interferon he rapidly progressed over the next three months with an EDSS = 8.0 (triplegic plus speech and swallowing impairments). A positive CSF PCR and culture for *C. pneumoniae* led to treatment with combination antibiotics. The patient improved on all spheres of neurologic function over the following six months. His EDSS score 9 months later was 3.0 with return to work and routine athletic activities (e.g. -jogging). His neurological status remains stable and he continues on an anti-chlamydial combination regimen. |
| MC | MS | | This patient had a ten year history of MS with evidence of progressive ataxia and weakness in the legs. Over 5 months his EDSS score worsened from 7.0 to 8.0. His CSF was positive by PCR for *C. pneumoniae* and he was placed on combination antibiotics. Over the next six months he gradually improved in his balance, coordination and lower extremity strength. His most recent EDSS score was 6.5. |
| JM | MS | | Initially seen with rapidly progressive paraparesis secondary to MS. He failed to response to corticosteroids on two successive occasions. Five months later, his EDSS score was 7.5. Following a positive *C. pneumoniae* PCR he was placed on combination antibiotics. He has gradually gained strength in his lower extremities and five months later was able to walk with a walker (EDSS = 6.5) while being maintained on combination antibiotics. |
| LL | MS | | Patient with a long history (14 years) of secondary progressive MS with recent progressive bulbar symptoms, axtaxia, and paraplegia (EDSS = 8.5). PCR for the MOMP gene of *C. pneumoniae* in the CSF was positive. She was placed on combination antibiotics with no further progression of symptoms for the last six months. |
| AN | MS | Row 10 | Long history of MS and wheel chair bound for approximately ten years. She has received continuous physical therapy to retain leg muscle tone. Following approximately 6 months of combination antibiotics, she was able to stand unaided and take several unaided steps. She reports a significant decrease in fatigue and cognitive dysfunction. She remains on combination antibiotics and other supportive medications. |
| FO | MS | Row 6 | Wheel chair bound with a long history of MS with a 2–3 year progression of severe dysarthriae and incontinence. On combination antibiotics (14 months) he has had improvement of speech and incontinence. Speech, ability to open mouth for dentist, stamina all improved. Can stand better on his own mid-transfer. He remains wheel chair bound. |
| JC | MS | | Diagnosis of MS with development of a foot drop approximately one year prior to therapy requiring the use of a cane in walking. Approximately four months after initiation of combination antibiotic therapy, patient reports reversal of foot drop and no longer requires a cane. She continues on antibiotic therapy. |
| FW | MS | | Male executive in late 50s with a 15 year history of MS. Used a cane for a rolling, unstable gait. Easily fatigued. After 12 months of combination antibiotics, was able to walk without cane or excessive fatigue, although his gait can still wander. Can easily make it across the parking lot, which had previously been a challenge. Stopped antibiotics even though was still PCR positive; plans to restart therapy if he has another flare-up. |
| LH | RA | Row 14 | Patient LH had an active case of RA which was moderately debilitating. Following two months of combination antibiotic therapy, her RA is in complete remission. |
| XX | IC | | She responded to combination antibiotics with complete remission of symptoms after one month. Cessation of antibiotics resulted in a return of IC symptoms |
| NC | PG | PCR + | 61 year old male who had had lesions for several years. Large ulcerated lesions on feet that resolved on combination antibiotic therapy. Only residual hypertrophic scars remain. |
| CH | PG | PCR + | 75-year-old male diabetic with multiple, large, severe lesions on both legs, abdomen, and arms. Lesions first formed in 1993. Severity of process required chronic nursing home care at an estimated cost of $300–400 per day. All lesions above the knee have resolved on combination antibiotic therapy: lesions only remain on right lower leg, where inadequate blood supply offers poor prognosis. The patient no longer requires nursing home care. |
| RI | PG | PCR + | Original severe PG lesions on legs required bilateral amputation. Lesions now occurring on arms. Treatment with combination antibiotics has resulted in resolution of lesions although not complete to date. [No update - chart missing] |
| PL | PG | PCR + | 18 year old female with history of leg ulcers. Multiple PG lesions completely healed on combination antibiotic therapy. Patient then lost his job and could not afford to maintain drug regimen. Upon re-flaring of ulcers, re-started therapy and ulcers improved again. |
| TW | PG | | Severe PG, initiated after a chemical burn in 1991, but with PCR negative serology for *C. pneumoniae*. Patient did not initially respond to combination antibiotic therapy. A positive biopsy culture for *C. pneumoniae* resulted in the recent re-institution of combination antibiotics. However, after no improvement, patient went off therapy. |

TABLE 13c-continued

Detailed Case Histories

| Patient | Diag | Test data[1] | Case History |
|---|---|---|---|
| AM | IBD | Row 5 | This is a 35 year old male who first presented as a prostititis ten years ago at the age of 25. This progressed to acute ulcerative colitis, involving the entire colon, which was associated with severe arthritis, iritis, and weight loss. Diagnosis was biopsy confirmed. Control required high doses of corticosteroids and azacol. Attempts to reduce steroids resulted in partial control of symptoms. Six months prior to initiation of combination antibiotic therapy, patient was experiencing frequency (20–25 times per day), frank bleeding, and mucus in the stool. Patient on combination antibiotics for one year. Following significant stress, patient had significant increase in symptoms. Alteration of antibiotic combination has resulted in normal bowel habits with no mucus and minimal blood. Associated neuropsychiatric manifestations of cognitive dysfunction and depression have resolved. Steroids have been discontinued. |
| AG | IBD | Row 12 | This is a 27 year old white female with a two month history of fulminate, progressive ulcerative colitis which had not responded to the usual medical therapy. A total abdominal colectomy with ileostomy and rectal pouch was done. The microscopic appearance confirmed ulcerative colitis. Following the colectomy, the patient experienced neurologic symptoms, fatigue, myalgias, arthralgias, and an acneoform skin rash. Serology was performed for *C. pneumoniae* and was positive with an IgM of 1:3200, IgG 1:400 and PCR positive. Therapy with combination antibiotics was initiated. After six months of antimicrobial therapy, her serology was IgM 1:800, IgG 1:400, and PCR positive. The neurological symptoms, fatigue, myalgias, arthralgias, and acneoform rash resolved completely. There was not further evidence of inflammatory bowel disease, and the ileostomy was successfully anastomised to the rectal stump. The patient has felt more energetic. Serology after 1 year was PCR negative. |
| DM | IBD | | This 37 year old female had a six year history of inflammatory bowel disease (uncertain CD or UC) associated with painless rectal bleeding, arthritis, myalgias, skin ulceration, abdominal cramping/diarrhea, and rectal fistulas. She had increasing fatigue which caused her to frequently miss work as a minor executive. On combination antibiotic therapy, all symptoms resolved but recurred with cessation of antibiotics while on vacation. Reinstitution of combination antibiotics resulted in a second remission of symptoms. Prior to combination antibiotic therapy, she had not gone longer than 3 months without an anal manifestation of IBD. She has been symptom free of IBD for over a year. |
| RP | IBD | | Patient presented with proctocolectomy and ileostomy due to UC. Following a flu-like illness in 1993, she became fatigued and anemic with blood-tinged diarrhea: Examination of her ileostomy pouch revealed inflammation and ulcerations. Upper GI series/small bowel series revealed no abnormalities and no cause of her anemia was diagnosed. On combination antibiotics her ileostomy activity was more regular and less spastic. She claimed to feel better with higher energy levels and ceased antibiotic therapy. Six months post-antibiotic therapy she remained asymptomatic other than a moderate anemia. |
| AB | IBD | | Patient with long history of CD involving small bowel, large bowel, and anus. She had been treated with a small bowel resection and fissurectomy. She continued to suffer from numerous rectal fistulas. On combination antibiotics she experience some symptomatic improvement but failed to completely resolve her IBD symptoms. She discontinued antibiotics due to a probable chronic Herxheimer reaction. Currently she is lost to follow-up. |
| EU | IBD | | Colitis with inflamed distal sigmoid colon and proctitis associated with frequent loose stools with significant mucus. Following six weeks of combination antibiotic therapy with a significant reduction in symptoms. Shortly after cessation of antibiotics her symptoms return. Reinstitution of antibiotics resulted in a second remission of the majority of her symptoms with resolution of her proctitis on visual exam. |
| NM | CFS | | Vanderbilt University initial patient that resulted in our first association of *C. pneumoniae*, initially complained of the insidious onset of debilitating fatigue. This was associated with a severe cognitive dysfunction that disrupted his ability to function as the supervisor of a clinical diagnostic laboratory. Despite six months of intensive diagnostic efforts by the Infectious Disease Clinic at Vanderbilt no definitive or presumptive diagnosis could be made. A subsequent high antibody titer against *C. pneumoniae* led to standard anti-chlamydial antibiotic therapy over a three month period with gradual disappearance of fatigue and cognition symptoms. On cessation of a fluroquinolone antibiotic, symptoms returned within two weeks. He was placed on combination antibiotics with complete reversal of symptoms after six months. He remains asymptomatic. |
| JS | CFS | Row 11 | Academic physician with a greater than 10 year history of CFS. Cognition problems resulted in his grounding himself as a private pilot. Initial treatment with combination antibiotics results in an apparent Herxheimer reaction with resolution over a two week period with gradual improvement in symptoms. After three months therapy, he piloted a light aircraft under instruments from Florida to North Carolina. He remains on combination antibiotics for over a year and is asymptomatic. |

TABLE 13c-continued

Detailed Case Histories

| Patient | Diag | Test data[1] | Case History |
|---|---|---|---|
| PM | CFS | Row 4 | Physician with long-standing CFS. Treated with combination antibiotics with gradual resolution of symptoms. During course of treatment developed cardiac myopathy. Currently asymptomatic from CFS. Cardiac myopathy resolved over six month period on combination antibiotics. |
| MM | CFS | Row 2 | CFS and AD. Resolution of postural tachycardia over 1 month combination antibiotic therapy. Partial reversal of fatigue during this period. Patient non-compliant after one month and lost to follow-up. |
| PH | FM | Row 1 | Three year history of debilitating FM following the stress of being a stalking victim. Patient relatively asymptomatic after nine months combination antibiotic therapy. |
| CN | CFS | Row 9 | Five year history of severe CFS with debilitating cognitive dysfunction and depression. Gradual improvement on combination antibiotics for approximately nine months. Estimated 75% of normal function. |
| PG | CFS | | Ten year history CFS with cognitive dysfunction. Complete response to combination antibiotics over a course of one year. |
| AT | CF | Row 13 | Moderate fatigue and cognitive dysfunction following acute infectious illness. Depression was major problem. During one year course of combination antibiotics fatigue and cognitive dysfunction largely reversed. During mid-course of therapy patient developed acute anxiety attacks relieved by anti-porphyrin therapy. |
| WM | CF | Row 7 | CF following acute stress. Pre-illness serum negative for anti-*Chlamydia pneumoniae* antibodies which peaked six weeks following stress. Pre-illness PCR was weak positive that became strongly positive. On combination antibiotic therapy at 3 months became asymptomatic. Cessation of antibiotics resulted in symptomatic relapse. Currently asymptomatic with low serum antibodies and negative PCR. |
| HM | CF | Row 8 | Medical student with short history of CF and cognitive dysfunction affecting studies. Combination antibiotics over a multi-month course resulted in complete reversal of symptoms. |
| ST | CFS | Row 17 | Mother of Patient AT. Three year history of CFS with FM. Combination antibiotic therapy has resulted in partial reversal of symptoms allowing her to retain a job in jeopardy. Estimated 80–90% normal function currently. |
| RV | CF | | History of fatigue although non-incapacitating. Combination antibiotic therapy has resulted in 100% return to normal function. |
| EB | CFS | | Teen-ager with long history of CFS resulting in home-bound schooling. On combination antibiotic therapy returned to school and recently graduated. Recovery has not been complete probably secondary to non-compliance in therapy. |

[1]Refers to row in Table 13b which has ELISA and PCR histories for these patients.

TABLE 13d

Drugs and Standard Dosages

| Drug | Generic | Unit dosage | Daily dosage |
|---|---|---|---|
| Cupramine | Penicillimine | 250 mg | 2× |
| Amoxicillin | | 500 mg | 2× |
| Flagyl | Metronidazole | 500 mg | 2× |
| INH | | 300 mg | 1× |
| Rifampin | | 300 mg | 2× |
| Floxin | Ofloxacin | 400 mg | 2× |
| Levaquin | | 500 mg | 1× |
| Bactrim | SMZ/TMP | Double Strength | 2× |
| Biaxin | Clarythromycin | 500 mg | 2× |
| Minocycline | | 100 mg | 2× |
| Doxycycline | | 100 mg | 2× |
| Probenicid | | 500 mg | 2× |

TABLE 14

Examples of Secondary Porphyria in Patients with Systemic infections caused by *C. pneumoniae*[a]

| Patient ID | Enzymes of Heme biosynthesis[b] | | Elevated Fecal Porphyrins (24 hr) | | | Elevated Urinary Porphyrins (24 hr) | | |
|---|---|---|---|---|---|---|---|---|
| | ALA synthase | PBG deaminase | Porphyrin | Level | Normal | Porphyrin | Level | Normal |
| KRH | 6.0 | 11.7 | Protoporphyrin | 913 | <500 | Coproporphryn | 115 | <60 |
| | | | Dicarboxyl porphyrin | 596 | <150 | (tetracarboxyl) | | |
| KB | 1.8 | 7.8 | None | | | Coproporphryn III | 248 | <45 |
| | | | | | | Isocoproporphryn | 142 | <10 |
| MB | Not done | Not done | Tetracarboxyl | 287 | <200 | Not done | | |
| | | | Coproporphryn | 177 | <150 | | | |
| | | | Coproporyn III | 396 | <200 | | | |
| | | | Tricarboxly porphryn III | 71 | <50 | | | |
| | | | Uroporphryn III | | | | | |
| SE | 6.6 | 9.7 | Isocoproporphyrin | 446 | <200 | Coproporphyrin | 89 | <60 |
| | | | Protoporphyrin | 3512 | <1500 | | | |
| | | | Semi-protoporphyrin | 2951 | <1500 | | | |
| | | | Total dicarboxyl porphyrins | 3390 | <1500 | | | |
| PE | 6.4 | 10.0 | None | | | Porphyrobelinigen | 2.5 | <1.5 |
| TE | 5.9 | 9.4 | Protoporphyrin | 2633 | <1500 | None | | |
| RH | 7.2 | 9.7 | Corproporphyrin I | 913 | <500 | None | | |
| | | | Corproporphyrin III | 596 | <150 | | | |
| | | | Protoporphyrin | 2884 | <1500 | | | |
| | | | Semiprotoporphyrin | 2305 | <1500 | | | |
| | | | Total dicaboxyl porphyrins | 3706 | <1500 | | | |
| NH | 7.9 | 11.5 | Uroporphyrin I | 241 | <120 | Pentacarboxyl porphyrin | 4 | <3 |
| | | | Uroporphyrin III | 125 | <50 | | | |
| | | | Semirprotoporphyrin | 3470 | <1500 | | | |

Example 6

Example of Clearing Mice

A set of mice were tested for infection with *C.pneumoniae*. Of 10 mice tested, 8 (80%) were PCR positive for *C.pneumoniae*. The mice were then placed on triple-antibiotic therapy: Amoxicillin, Metronidazole and fNH at 50 µg/ml each in their water. Based on their water consumption of 6.8 to 7 ml per day, the mice were effectively receiving approximately 350 µg of each drug each day.

The mice were tested again, by PCR, on the first generation of pups once they were old enough. They still tested positive by PCR. The mouse colony was then maintained on the combination therapy in water for several months. Approximately seven months after the start of this study, probenicid was added to the water as well. Roughly 2 to 3 weeks after the probenicid was added, the then third or fourth generation of mice was again tested. All 22 mice tested were then PCR negative.

Example 7

Determination of Secondary Porphyria

Patents with systemic infections caused by *C.pneumoniae* were evaluated for secondary porphyria. The presence of enzymes (i.e., Δ-ALA synthase and PBG deaminase) for heme biosynthesis were determined using known methods. Elevated fecal and urinary prophyrins were measured at 24 hours. The results are reported in Table 14.

TABLE 14-continued

Examples of Secondary Porphyria in Patients with Systemic infections caused by C.pneumoniae[a]

| Patient ID | Enzymes of Heme biosynthesis[b] | | Elevated Fecal Porphyrins (24 hr) | | | Elevated Urinary Porphyrins (24 hr) | | |
|---|---|---|---|---|---|---|---|---|
| | ALA synthase | PBG deaminase | Porphyrin | Level | Normal | Porphyrin | Level | Normal |
| SE | 6.6 | 9.7 | Isocoproporphyrin | 446 | <200 | Coproporphyrin | 89 | <60 |
|  |  |  | Protoporphyrin | 3512 | <1500 |  |  |  |
|  |  |  | Semi-protoporphyrin | 2951 | <500 |  |  |  |
|  |  |  | Total dicarboxyl porphyrins | 3390 | <1500 |  |  |  |
| PE | 6.4 | 10.0 | None |  |  | Porphyrobelinigen | 2.5 | <1.5 |
| TE | 5.9 | 9.4 | Protoporphyrin | 2633 | <1500 | None |  |  |
| RH | 7.2 | 9.7 | Corproporphyrin I | 913 | <500 | None |  |  |
|  |  |  | Corproporphyrin III | 596 | <150 |  |  |  |
|  |  |  | Protoporphyrin | 2884 | <1500 |  |  |  |
|  |  |  | Semiprotoporphyrin | 2305 | <1500 |  |  |  |
|  |  |  | Total dicaboxyl porphyrins | 3706 | <1500 |  |  |  |
| NH | 7.9 | 11.5 | Uroporphyrin I | 241 | <120 | Pentacarboxyl porphyrin | 4 | <3 |
|  |  |  | Uroporphyrin III | 125 | <50 |  |  |  |
|  |  |  | Semirprotoporphyrin | 3470 | <1500 |  |  |  |
| GK | Not done | Not done | Coproporphyrin III | 175 | <50 | Not done |  |  |
|  |  |  | Total dicarboxyl porphyrins | 1635 | <1500 |  |  |  |
| AL | Not done | Not done | Uroporphyrin I | 237 | <50 | Not done |  |  |
|  |  |  | Coproporphyrin I | 601 | <500 |  |  |  |
|  |  |  | Coproporphyrin III | 476 | <150 |  |  |  |
|  |  |  | Protoporphyrin | 1865 | <1500 |  |  |  |
| JW | 6.7 | 11.5 | Hectacarboxyl porphyrin I | 13 | <10 | None |  |  |
|  |  |  | Hectacarboxyl porphyrin III | 18 | <10 |  |  |  |
|  |  |  | Dicarboxyl porphyrin | 107 | <100 |  |  |  |
| HW | 7.2 | 11.2 | Isohexycarboxyl porphyrin | 19 | <10 | None |  |  |
|  |  |  | Coproporphyrin I | 573 | <500 |  |  |  |
|  |  |  | Semiprotoporphyrin | 1712 | <1500 |  |  |  |
|  |  |  | Dicarboxyl porphyrin | 2769 | <1500 |  |  |  |

[b]Reported as mmol/sec/l.

|  | ALA synathase | PGB deaminase |
|---|---|---|
| High levels | >4.0 | >7.0 |
| Low levels | <3.5 | <6.0 |

[a]All assays performed at the Mayo Clinic, which established the normal reference values.
Levels above normal justify a diagnosis of porphyria.

Example 8

Presence of Autoantibodies to Porphyrin Ring Structures

Patients with systemic infections caused by *C.pneumoniae* were tested for the presence of antibodies to porphyrin ring structures (i.e., vitamin B12, coproporphyrinogen-III, protoporphyrin, porphyrobelinigen and Δ-ALA). IgM and IgG antibody titers were determined using an ELISA assay, for which the protocol is described below.

ELISA Assay Protocol

1. Plate Preparation: Coproporphyrin III is used as an example but the procedure is also preformed by coating plates with one of the following other ring structures at the same concentration: vitamin B12, protoporphyrin IX, porphobilinogen and Δ-aminolevulinic acid. Add 50 ng. of Coproporphyrin III in 50 μl of carbonate coating buffer to each well in columns 1–11 of a 96 well Immulon 4 microtiter plate. Cover with plastic wrap and incubate overnight at 4° C.

2. Block step: Wash plates three times with Tween 20 wash buffer. (0.1M Tris; 0.15% Tween 20; 0.05% NaN$_3$) Block plates by adding 200 μl of Tris block buffer (Tris 0.1M; 1% bovine serum albumin; 0.15% Tween 20) to each well of columns 1–11. Leave the wells of column 12 dry. Wrap plates with plastic wrap and incubate at room temperature for 1 hour.

3. Sample preparation: While plates are blocking prepare samples and controls. Dilute patients sera 1:10 in block and vortex well.

4. Plate preparation: Wash plates with Tween 20 wash buffer three times and add 50 μl block in each well in each row except row A and every column except column 12. Leave row A and column 12 empty.

5. Plate configuration: Place 100 μl of patient dilutions in duplicate in row A. Prepare plates in duplicate and label one plate for IgG and one for IgM detection. Use the Cetus Propet apparatus to twofold serially dilute (1:10 to 1:1280) the samples in column 1–10. The following loading configuration is used for patient samples and controls:

Sample 1—columns 1 and 2
Sample 2—columns 3 and 4
Sample 3—columns 5 and 6
Sample 4—columns 7 and 8
High positive control—column 9
Low positive or negative control—column 10
Block only—column 11
Column 12 dry—air blank Wrap with plastic wrap and incubate at 37° C. for 1 hour.

6. Detection antibodies: Prepare five minutes before incubation is up separate 1:2000 dilutions in Tris block buffer of mouse monoclonal biotin labeled anti-human IgG and IgM. Wash the plates in FCS wash (0.1M Tris; 0.05% $NaN_3$; 0.15% Tween 20; 1% FCS) four times and place 50 μl of the anti-human IgG dilution in each well of columns 1–11 of the plates labeled IgG. Repeat using anti-human IgM in plates labeled IgM. Wrap with plastic wrap and incubate for one hour at 37° C.

7. Ligand: Prepare five minutes before the incubation is up a 1:1000 dilution of streptavidin-alkaline phosphatase conjugate in Tris block buffer. Wash the plates with FCS wash four times and place 50 μl of the streptavidin dilution in each well of columns 1–11. Wrap with plastic wrap and incubate one hour at 37° C.

8. Prepare P-Nitrophenlphosphate (PNPP) 30 minutes before incubation is complete by dissolving Immunopure PNPP tablets in diethanolamine substrate buffer. Prepare one tablet in five ml 1×DEA substrate buffer for each plate.

9. When incubation is complete wash plates in FCS wash four times and add 50 μl of PNPP to each well of columns 1–11. Wrap with plastic film and allow color to develop by incubating one hour at room temperature. It is best to protect from light during the incubation period. At the end of the incubation period stop the color development by adding 50 μl of 3N NaOH to each well of columns 1–11.

10. Read the plates at a wavelength 404 nM using a Titertek plate reader.

The results are reported below in Table 15.

TABLE 15

Examples of Antibody Titers[a] to Porphyrin Ring Structures in Patients with Systemic infections caused by C. pneumoniae

| Patient | B12 | | Copro III | | Protoporphyrin | | Porphyrobelinigen | | —ALA | |
| --- | --- | --- | --- | --- | --- | --- | --- | --- | --- | --- |
| ID | IgM | IgG | IgM | IgG | IgM | IgG | IgM | IgG | IgM | IgG |
| KRH | 1:640 | 1:160 | 1:640 | 1:160 | 1:1280 | 1:640 | 1:1280 | 1:80 | 1:640 | 1:640 |
| KB | 1:640 | 1:80 | 1:320 | 1:40 | 1:1280 | 1:1280 | 1:160 | 1:40 | 1:160 | 1:320 |
| MB | 1:160 | 1:160 | 1:160 | 1:80 | 1:160 | 1:60 | 1:160 | 1:160 | 1:320 | 1:640 |
| SE | 1:1280 | 1:160 | 1:1280 | 1:80 | 1:1280 | 1:1280 | 1:640 | 1:640 | 1:640 | 1:1280 |
| AEM | 1:1280 | 1:320 | 1:1280 | 1:160 | — | — | — | — | — | — |
| GK | 1:640 | 1:20 | 1:320 | 1:20 | 1:1280 | 1:80 | 1:1280 | 1:40 | 1:1280 | 1:40 |
| AL | 1:1280 | 1:20 | 1:1280 | 1:10 | 1:1280 | 1:80 | 1:1280 | 1:40 | 1:1280 | 1:40 |
| PE | — | — | 1:640 | 1:20 | 1:640 | 1:640 | 1:320 | 1:20 | 1:320 | 1:640 |
| RH | — | — | 1:160 | 1:80 | 1:40 | 1:640 | 1:160 | 1:160 | 1:40 | 1:320 |
| NH | — | — | 1:320 | 1:160 | 1:320 | 1:1280 | 1:640 | 1:320 | 1:160 | 1:320 |
| JW | — | — | 1:320 | 1:80 | 1:640 | 1:640 | 1:160 | 1:80 | 1:320 | 1:320 |
| SW-H | — | — | 1:640 | 1:40 | 1:640 | 1:320 | 1:640 | 1:40 | 1:320 | 1:160 |
| Cord 1 | 0 | 0 | 1:10 | 1:80 | 0 | 1:80 | — | — | 1:10 | 1:10 |
| Cord 2 | 0 | 1:20 | 1:10 | 1:80 | 1:10 | 1:160 | 0 | 1:80 | 0 | 1:20 |
| Cord 3 | 0 | 1:20 | 1:20 | 1:80 | 0 | 1:20 | 0 | 1:10 | 0 | 0 |

[a]Antibodies are quantitated in an ELISA format

Equivalents

While this invention has been particularly shown and described with references to preferred embodiments thereof. it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A combination of antichlamydial agents comprising (i) a rifamycin; (ii) an azalide or a macrolide; and (iii) penicillamine in amounts effective for the treatment of a chlamydial infection, said combination further comprising an anti-inflammatory agent or an immunosuppressive agent.

2. The combination of antichlamydial agents of claim 1, wherein said rifamycin is rifampin.

3. The combination of antichlamydial agents of claim 1, wherein said azalide is azithromycin.

4. A combination of antichlamydial agents comprising at least two antichlamydial agents at unit dosages and in amounts sufficient for treating a patient having a chlamydial infection for at least forty-five days, wherein said antichlamydial agents are selected from the group consisting of a rifamycin, ampicillin, amoxicillin, an azalide, a macrolide, a nitroimidazole, a quinolone, a fluoroquinolone, a tetracycline, and a sulfonamide, said combination further comprising an anti-inflammatory agent or an immunosuppressive agent.

5. The combination of antichlamydial agents of claim 4, said combination comprising at least three antichlamydial agents at unit dosages and in amounts sufficient for treating the patient for at least forty-five days, wherein said antichlamydial agents are selected from the group consisting of a rifamycin, ampicillin, amoxicillin, an azalide, a macrolide, a nitroimidazole, a quinolone, a fluoroquinolone, a tetracycline, and a sulfonamide.

6. A combination of antichlamydial agents comprising at least two antichlamydial antibiotics at unit dosages and in amounts sufficient for treating a patient having a chlamydial infection for at least forty-five days, wherein said antichlamydial antibiotics are effective against at least two phases of the chlamydial life cycle selected from the elementary body phase, the replicating phase, and the cryptic phase, said combination further comprising an anti-inflammatory agent or an immunosuppressive agent.

7. The combination of antichlamydial agents of claim 6, wherein said antichlamydial antibiotics are in an amount sufficient for treating the patient for at least sixty days.

8. The combination of antichlamydial agents of claim 6, wherein said antichlamydial antibiotics are in an amount sufficient for treating the patient for at least ninety days.

9. The combination of antichlamydial agents of claim 6, said combination comprising at least three antichlamydial antibiotics at unit dosages and in amounts sufficient for treating said patient for at least forty-five days, wherein said antichlamydial antibiotics are effective against at least two phases of the chlamydial life cycle selected from the elementary body phase, the replicating phase, and the cryptic phase.

* * * * *

UNITED STATES PATENT AND TRADEMARK OFFICE
CERTIFICATE OF CORRECTION

PATENT NO. : 6,579,854 B1
DATED : June 17, 2003
INVENTOR(S) : William M. Mitchell and Charles W. Stratton It is certified that error appears in the above-identified patent and that said Letters Patent is hereby corrected as shown below:

Title page,
Item [56], References Cited, FOREIGN PATENT DOCUMENTS,
"EP 0 192 033 A2" reference, replace "8/1996" with -- 8/1986 --.
OTHER PUBLICATIONS,
"Orfila, J. and Haider, F." reference, replace "Amoxicilli" with -- Amoxicillin --.
"Schachter" reference, replace "5;S" with -- 5:S --.

Column 5,
Line 13, replace "Chlaniy-" with -- Chlamy- --.

Column 6,
Line 4, replace "plished.by" with -- plished by --;
Line 49, replace "Chiamydia" with -- Chlamydia --; and
Line 60, replace "ihigh" with -- high --.

Column 8,
Line 8, replace "Chiamydia" with -- Chlamydia --.

Column 10,
Line 43, replace "Chlarnydia" with -- Chlamydia --.

Column 15,
Line 5, replace "Chiamydia" with -- Chlamydia --;
Line 10, replace "mab" with -- mAb --; and
Line 63, replace "materials")" with -- materials" --.

Column 16,
Line 27, replace "Chiamydia" with -- Chlamydia --.

Column 19,
Line 26, replace "invention." with -- invention, --.

Column 20,
Line 11, replace "chiamydial" with -- chlamydial --; and
Line 63, replace "nifuirtimox" with -- nifurtimox --.

Column 21,
Line 2, replace ""metabolites")" with -- "metabolites" --;
Line 28, replace "antichlarnydial" with -- antichlamydial --; and
Line 56, replace "chiamydial" with -- chlamydial --.

UNITED STATES PATENT AND TRADEMARK OFFICE
CERTIFICATE OF CORRECTION

PATENT NO.     : 6,579,854 B1
DATED          : June 17, 2003
INVENTOR(S)    : William M. Mitchell and Charles W. Stratton It is certified that error appears in the above-identified patent and that said Letters Patent is hereby corrected as shown below:

Column 22,
Line 35, replace "load")" with -- load" --;
Line 48, replace "term." with -- term," --; and
Line 56, replace "sections." with -- sections," --.

Column 23,
Line 65, replace "arc" with -- are --.

Column 26,
Line 34, replace "Chlarnydia" with -- Chlamydia --; and
Line 45, Table 6, title, replace "Chlamydialc" with -- Chlamydial --.

Column 27,
Line 39, replace "(Grupta el" with -- (Grupta et --; and
Line 53, replace "herein." with -- herein, --.

Column 28,
Line 2, Table 6, title, replace "Chlamydialc" with -- Chlamydial --; and
Line 67, replace "tracheobronchitis." with -- tracheobronchitis, --.

Column 29,
Line 18, replace "degenerations." with -- degenerations, --.

Column 30,
Line 67, replace "antichlarnydial" with -- antichlamydial --.

Column 31,
Line 12, replace "Cortisone." with -- Cortisone, --;
Line 21, replace "Wang el al." with -- Wang et al. --;
Line 41, replace "free-radicals." with -- free-radicals, --; and
Line 43, replace "chiamydial" with -- chlamydial --.

Column 34,
Line 1, replace "formn" with -- form --.

Column 35,
Line 63, replace "chlarnydial" with -- chlamydial --.

Column 37,
Line 64, replace "lThe" with -- The --.

UNITED STATES PATENT AND TRADEMARK OFFICE
CERTIFICATE OF CORRECTION

PATENT NO. : 6,579,854 B1
DATED : June 17, 2003
INVENTOR(S) : William M. Mitchell and Charles W. Stratton It is certified that error appears in the above-identified patent and that said Letters Patent is hereby corrected as shown below:

Column 38,
Line 40, replace "5-hydroxytryptariine" with -- 5-hydroxytryptamine --.

Column 39,
Line 2, replace "However." with -- However, --; and
Line 11, replace "fiee-radicaI" with -- free-radical--.

Column 40,
Line 15, replace "lcvels" with -- levels --; and
Line 16, replace "or.the" with -- or the --.

Column 41,
Line 46, replace "cycle." with -- cycle, --; and
Line 49, replace "disorders." with -- disorders, --.

Column 42,
Line 53, replace "embodiment." with -- embodiment, --.

Column 44,
Line 31, replace "salves." with -- salves, --; and
Line 48, replace "hydroxides." with -- hydroxides, --.

Column 46,
Line 48, replace "phenol-" with -- phenol --.

Column 49,
Line 1, replace "chiamydial" with -- chlamydial --;
Line 11, replace "Chiamydia" with -- Chlamydia --; and
Line 14, replace "fuirther" with -- further --.

Column 52,
Line 16, replace "Combinations")" with -- Combinations" --.

Column 65,
Line 36, replace "fNH" with -- INH --.

UNITED STATES PATENT AND TRADEMARK OFFICE
CERTIFICATE OF CORRECTION

PATENT NO. : 6,579,854 B1
DATED : June 17, 2003
INVENTOR(S) : William M. Mitchell and Charles W. Stratton It is certified that error appears in the above-identified patent and that said Letters Patent is hereby corrected as shown below:

Column 70,
Line 58, replace "thereof." with -- thereof, --.

Signed and Sealed this

Sixteenth Day of August, 2005

JON W. DUDAS
*Director of the United States Patent and Trademark Office*